US011085084B2

(12) United States Patent
Diehn et al.

(10) Patent No.: US 11,085,084 B2
(45) Date of Patent: Aug. 10, 2021

(54) IDENTIFICATION AND USE OF CIRCULATING NUCLEIC ACIDS

(71) Applicant: The Board of Trustees of the Leland Stanford Junior University, Stanford, CA (US)

(72) Inventors: Maximilian Diehn, San Carlos, CA (US); Arash A. Alizadeh, San Mateo, CA (US); Aaron M. Newman, Palo Alto, CA (US); Daniel M. Klass, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 624 days.

(21) Appl. No.: 15/509,709

(22) PCT Filed: Sep. 11, 2015

(86) PCT No.: PCT/US2015/049838
§ 371 (c)(1),
(2) Date: Mar. 8, 2017

(87) PCT Pub. No.: WO2016/040901
PCT Pub. Date: Mar. 17, 2016

(65) Prior Publication Data
US 2018/0251848 A1 Sep. 6, 2018

Related U.S. Application Data

(60) Provisional application No. 62/049,959, filed on Sep. 12, 2014.

(51) Int. Cl.
| | | |
|---|---|---|
| *C12Q 1/6886* | (2018.01) | |
| *C12Q 1/6855* | (2018.01) | |
| *C12N 15/11* | (2006.01) | |
| *C40B 40/06* | (2006.01) | |
| *C12Q 1/6806* | (2018.01) | |
| *C12N 15/10* | (2006.01) | |
| *C12Q 1/6874* | (2018.01) | |
| *C40B 20/04* | (2006.01) | |
| *G16B 20/20* | (2019.01) | |

(52) U.S. Cl.
CPC ....... *C12Q 1/6886* (2013.01); *C12N 15/1065* (2013.01); *C12N 15/11* (2013.01); *C12Q 1/6806* (2013.01); *C12Q 1/6855* (2013.01); *C12Q 1/6874* (2013.01); *C40B 40/06* (2013.01); *G16B 20/20* (2019.02); *C12Q 2600/156* (2013.01); *C40B 20/04* (2013.01)

(58) Field of Classification Search
None
See application file for complete search history.

(56) References Cited

U.S. PATENT DOCUMENTS

| | | |
|---|---|---|
| 2003/0211504 A1 | 11/2003 | Fechtel et al. |
| 2006/0040282 A1 | 2/2006 | Monforte et al. |
| 2010/0029498 A1 | 2/2010 | Gnirke et al. |
| 2010/0041048 A1 | 2/2010 | Diehl et al. |
| 2012/0122701 A1 | 5/2012 | Ryan et al. |
| 2013/0231253 A1 | 9/2013 | Amorese et al. |
| 2014/0066317 A1 | 3/2014 | Talasaz |
| 2014/0235506 A1 | 8/2014 | Hindson et al. |

FOREIGN PATENT DOCUMENTS

| | | |
|---|---|---|
| CN | 102586420 A | 7/2012 |
| WO | WO2006047787 | 5/2006 |
| WO | 2013/142389 A1 | 9/2013 |
| WO | 2013/181170 A1 | 12/2013 |
| WO | WO2013190441 | 12/2013 |
| WO | 2014151117 A1 | 9/2014 |
| WO | 2015/100427 A1 | 7/2015 |

OTHER PUBLICATIONS

Bosch et al. Keeping Up With the Next Generation Massively Parallel Sequencing in Clinical Diagnostics Journal of Molecular Diagnostics vol. 10, pp. 484-492 (Year: 2008).*
Van Dijk et al. Ten years of next-generation sequencing technology Trends in Genetics vol. 30, pp. 418-426 (Year: 2014).*
Craig et al. Identification of genetic variants using bar-coded multiplexed sequencing Nature Methods vol. 5, pp. 887-893 (Year: 2008).*
Venter et al., "The Sequence of the Human Genome", Science, Feb. 16, 2001, pp. 1305-1351, vol. 291, Issue 5507, American Association for the Advancement of Science, Washington, D.C.
Baudet et al. "Cassis: detection of genomic rearrangement breakpoints", Bioinformatics, Aug. 1, 2010, pp. 1897-1898, vol. 26, No. 15, Oxford University Press, Oxford, United Kingdom.
Jiang et al., "PRISM: Pair-read informed split-read mapping for base-pair level detection of insertion, deletion and structural variants", Bioinformatics, Oct. 15, 2012, pp. 2576-2583, vol. 28, Issue 20, Oxford University Press, Oxford, United Kingdom.
Qu et al., "Efficient frequency-based de novo short-read clustering for error trimming in next generation sequencing"; Genome Res., May 13, 2009, pp. 1309-1315, 19, Cold Spring Harbor, Cold Spring Harbor, NY.
Suzuki et al., "ClipCrop: a tool for detecting structural variations with single-base resolution using soft-clipping information", BMC Bioinformatics, 2011, pp. 1-9, vol. 12, Supplement 14, BioMed Central, London, United Kingdom.
Luo et al., "Diagnostic value of circulating free DNA for the detection of EGFR mutation status in NSCLC: a systematic review and meta-analysis," Scientific Reports, Sep. 9, 2014, pp. 1-7, 4(1), Macmillan Publishers Limited, Basingstoke, United Kingdom.

(Continued)

Primary Examiner — John S Brusca
(74) Attorney, Agent, or Firm — Pamela J. Sherwood; Bozicevic, Field & Francis LLP

(57) ABSTRACT

Disclosed herein are polynucleotide adaptors and methods of use thereof for identifying and analyzing nucleic acids, including cell-free nucleic acids from a patient sample. Also disclosed herein are methods of using the adaptors to detect, diagnose, or determine prognosis of cancers.

1 Claim, 47 Drawing Sheets

(56) References Cited

OTHER PUBLICATIONS

Fu et al., "Molecular indexing enables quantitative targeted RNA sequencing and reveals poor efficiencies in standard library preparations", Proc Nat Acad Sci, Feb. 4, 2014, pp. 1891-1896, vol. 111 No. 5, PNAS, Washington, DC.

Johansson et al., "Targeted resequencing of candidate genes using selector probes," Nucleic Acids Research, Nov. 8, 2010, pp. 1-13, vol. 39, No. 2, Oxford University Press, Oxford, United Kingdom.

Newman et al., "An ultrasensitive method for quantitating circulating tumor DNA with broad patient coverage," Nature Medicine, Apr. 6, 2014, pp. 548-556 and Online supplementary material, Nature Medicine, Apr. 6, 2014, pp. 1-22, Macmillan Publishers Limited, Basingstoke, United Kingdom.

Diehl et al., "Circulating mutant DNA to assess tumor dynamics", Nature Medicine, Sep. 1, 2008, pp. 985-990, vol. 14, No. 9, Nature Medicine, New York, NY.

Duncavage et al., "Targeted next generation sequencing of clinically significant gene mutations and translocations in leukemia", Modern Pathology, Mar. 16, 2012, pp. 795-804, vol. 25, No. 6, Springer Nature Limited, New York City, NY.

Teer et al., "Systematic comparison of three genomic enrichment methods for massively parallel DNA sequencing", Genome Research, Sep. 1, 2010, pp. 1420-1431, vol. 20, No. 10, Cold Spring Harbor Press, Cold Spring Harbor, NY.

Mardis et al. (2011) "A decades perspective on DNA sequencing technology"; Nature; vol. 470; Feb. 10, 2011; p. 198-203.

Rausch et al. (2012) "DELLY: structural variant discovery by integrated paired-end and split-read analysis"; Bioinformatics, vol. 28, Issue 18, Sep. 15, 2012, pp. i333-i339.

Sboner, A. et al (2010) "FusionSeq: a modular a modular framework for finding gene fusions by analyzing paired-end RNA-sequencing data"; Genome Biology, 11:R104, p. 1-9.

Forshew et al (2012) "Noninvasive Identification and Monitoring of Cancer Mutations by Targeted Deep Sequencing of Plasma DNA", Science Translational Medicine, vol. 4, No. 136, pp. 136ra68-136ra68.

Gnirke et al. (2009) "Solution hybrid selection with ultra-long oligonucleotides for massively parallel targeted sequencing", Nature Biotechnology, Feb. 1, 2009, pp. 182-189, 27(2), Macmillan Publishers Limited, Basingstoke, United Kingdom.

Leary et al. (2010) "Development of Personalized Tumor Biomarkers Using Massively Parallel Sequencing", Science Translational Medicine, Feb. 24, 2010, pp. 1-7, 2(20), American Association for the Advancement of Science, Washington, D.C.

Martinez et al. (2013) "Computational optimisation of targeted DNA sequencing for cancer detection", Scientific Reports, Dec. 3, 2013, pp. 1-8, vol. 3, article No. 3309, Nature Publishing Group, London, United Kingdom.

McBride et al. (2010) "Use of Cancer-Specific Genomic Rearrangements to Quantify Disease Burden in Plasma from Patients with Solid Tumors", Genes, Chromosomes, & Cancer, Nov. 2010, pp. 1062-1069, vol. 49, Issue 11, Wiley, Hoboken, NJ.

Mertes et al (2011) "Targeted enrichment of genomic DNA regions for next-generation sequencing", A Briefings in Functional Genomics, vol. 10, No. 6, pp. 374-386.

Narayan et al. (2012) "Ultrasensitive Measurement of Hotspot Mutations in Tumor DNA in Blood Using Error-Suppressed Multiplexed Deep Sequencing", Cancer Research, pp. 3492-3498, vol. 72, No. 14, American Association for Cancer Research, Philadelphia, PA.

Pao et al. (2011) "New driver mutations in non-small-cell lung cancer", The Lancet, Feb. 2011, pp. 175-180, vol. 12, Issue 2, Elsevier, Amsterdam, Netherlands.

Wagle et al. (2012) "High-Throughput Detection of Actionable Genomic Alterations in Clinical Tumor Samples by Targeted, Massively Parallel Sequencing", Cancer Discovery, Jan. 2012, pp. 82-93, 2(1), American Association for Cancer Research, Philadelphia, PA.

Blumenstie et al. (2010) "Targeted Exon Sequencing by In-Solution Hybrid Selection". Current Protocols in Human Genetics, 66: 18.4.1-18.4.24.

Campbell et al. (2008) "Identification of somatically acquired rearrangements in cancer using genome-wide massively parallel paired-end sequencing"; Nature Genetics, vol. 40, No. 6; pp. 722-729.

Mcpherson et al. (2012) "nFuse: Discovery of complex genomic rearrangements in cancer using high-throughput sequencing", Genome Research, 22; pp. 2250-2261.

Bratman et al. (2013) Abstract 223: "Noninvasive and Ultrasensitive Quantitation of Circulating Tumor DNA by Hybrid Capture and Deep Sequencing", International Journal of Radiation Oncolo.av, 87(25):S92.

He et al. (2011) "IgH gene rearrangements as plasma biomarkers in Non-Hodgkin's Lymphoma patients" Oncotarget, 2(3): 178-185.

He et al. "Supplemental Table 4", pp. 1-2.

Heitzer et al. (2013) "Tumor-associated copy number changes in 06 the circulation of patients with prostate cancer identified through whole genome sequencing"; Genome Medicine, 1-16.

Herman et at (2009) "Filter-based hybridization capture of sub genomes enables resequencing and copy-number detection"; Nat Methods, 6(7): 507-510.

Mamanova et al. (2010) "Target-enrichment strategies for next generation sequencing", Nature Methods, 7(2):111-118.

Murtaza et al. (2013) "Non-invasive analysis of acquired resistance to cancer therapy by sequencing of plasma DNA"; Nature, vol. I 497, pp. 108-112.

Schwarzenbach et al. (2011) "Cell-free nucleic acids as biomarkers in cancer patients", Nature Reviews Cancer, 11 :426-37.

* cited by examiner

Ligation of sequencing adapters to cfDNA

Nucleic acid 
Endogenous barcode 1 
Endogenous barcode 2 
FIG. 3A
FIG. 3B
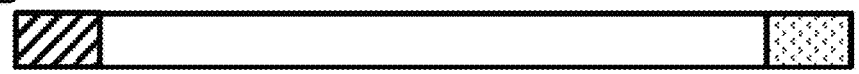
FIG. 3C
FIG. 3D
FIG. 3E
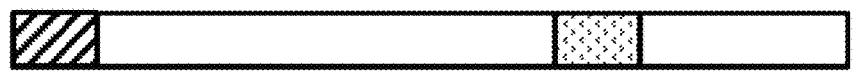

FIG. 5A

NSCLC

| Feature | n |
|---|---|
| Total size (kb) | 203 |
| No. regions (all) | 211 |
| No. unique genes | 134 |
| No. exonic regions | 207 |
| No. breakpoint hotspots | 2 |
| No. TKI exons | 4 |
| No. intergenic regions | 2 |
| Median mutations (top 10 regions) | 1 |
| Median mutations (all regions) | 8 |

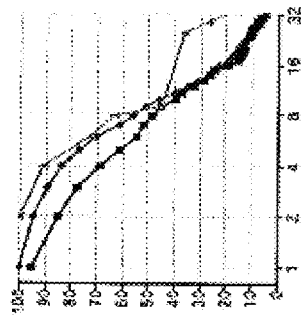

EAC/ESCC

| Feature | n |
|---|---|
| Total size (kb) | 180 |
| No. regions (all) | 765 |
| No. unique genes | 611 |
| No. exonic regions | 765 |
| Median mutations (top 10 regions) | 1 |
| Median mutations (all regions) | 7-8 |

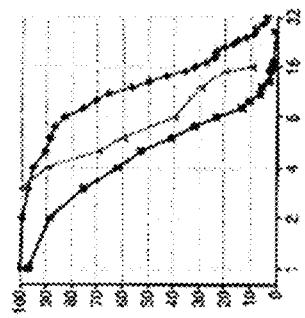

PAAD

| Feature | n |
|---|---|
| Total size (kb) | 185 |
| No. regions (all) | 979 |
| No. unique genes | 889 |
| No. exonic regions | 979 |
| Median mutations (top 10 regions) | 1 |
| Median mutations (all regions) | 8-11 |

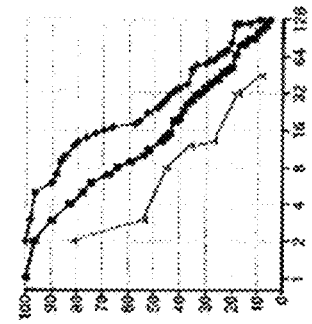

♦ - Training set
■ - Validation sets

Lane balancing algorithm
Maximize sensitivity while minimizing sequencing cost

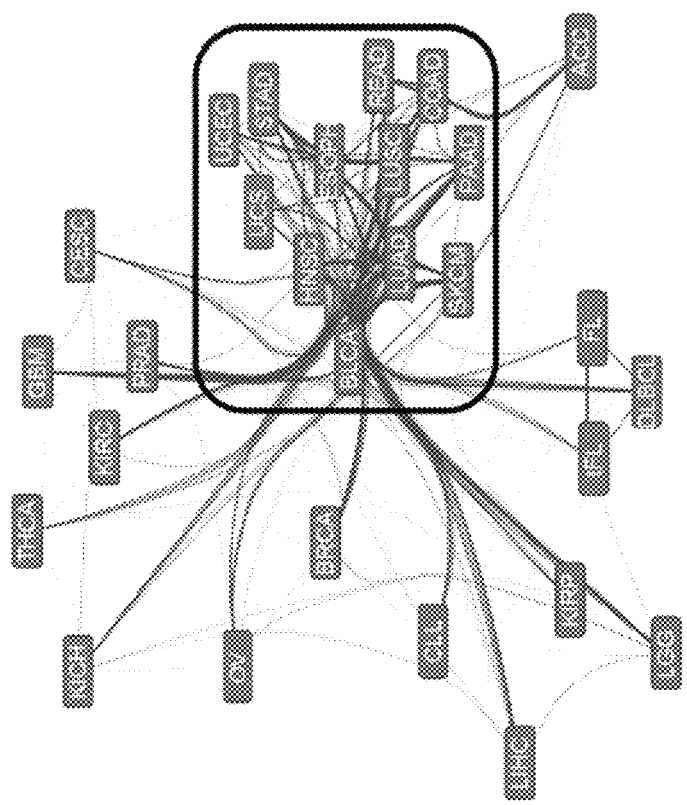
FIG. 8B
FIG. 8C
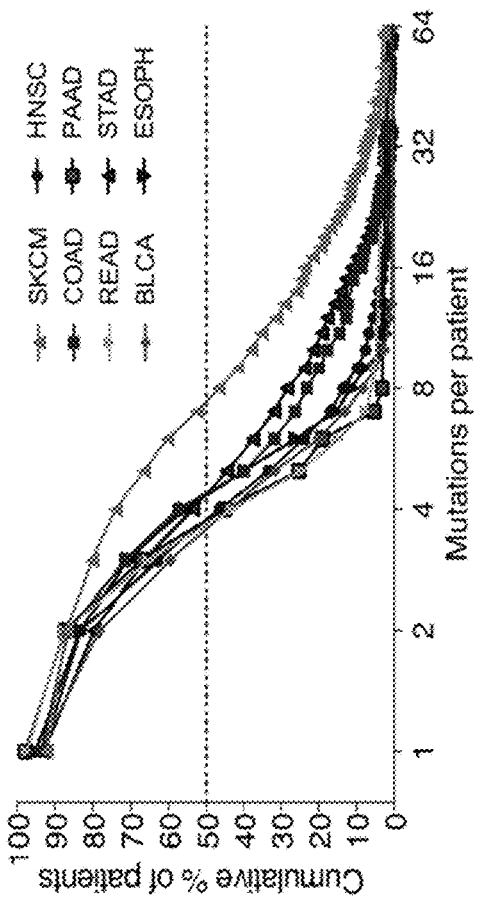
FIG. 8A

FIG. 11D  Ratio of G>T:C>A in Positions with Duplex Support

FIG. 15C
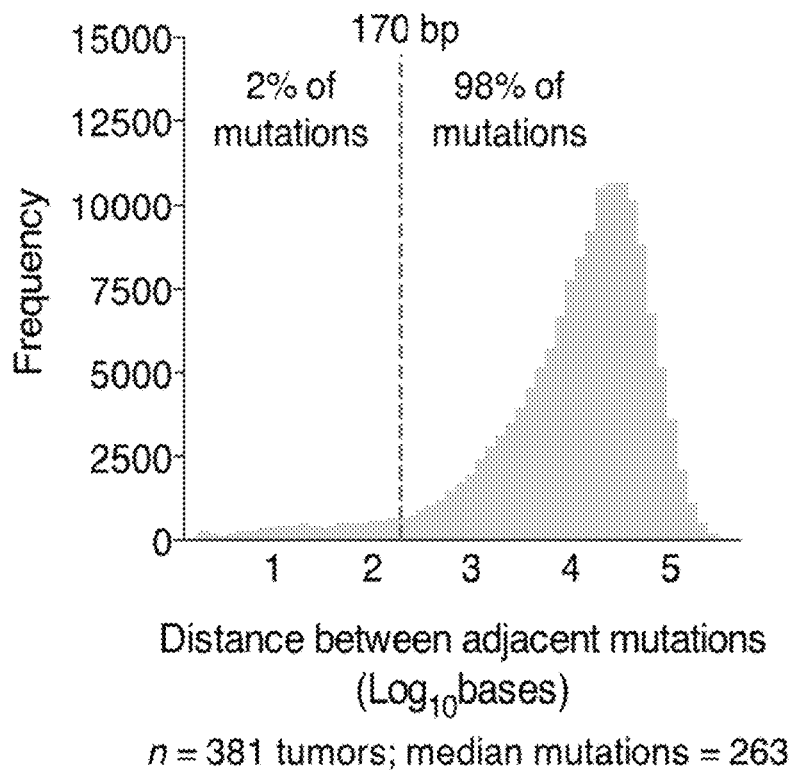
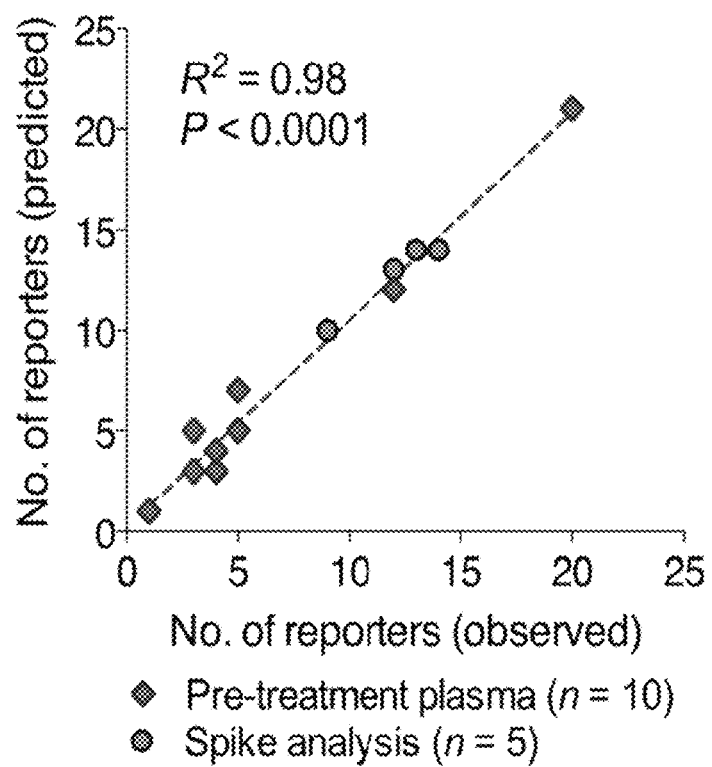
FIG. 15D

IDENTIFICATION AND USE OF CIRCULATING NUCLEIC ACIDS

CROSS REFERENCE

This application is a 371 application and claims the benefit of PCT Application No. PCT/US2015/049838, filed Sep. 11, 2015, which claims benefit of U.S. Provisional Patent Application No. 62/049,959, filed Sep. 12, 2014, which applications are incorporated herein by reference in their entirety.

FEDERALLY SPONSORED RESEARCH AND DEVELOPMENT

This invention was made with Government support under contract W81XWH-12-1-0285 awarded by the Department of Defense. The Government has certain rights in the invention.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

BACKGROUND OF THE INVENTION

Tumors continually shed DNA into the circulation, where it is readily accessible (Stroun et al. (1987) *Eur J Cancer Clin Oncol* 23:707-712). Analysis of such cancer-derived cell-free DNA (cfDNA) has the potential to revolutionize detection and monitoring of cancer. Noninvasive access to tumor-derived DNA is particularly attractive for solid tumors. However, analysis of circulating tumor nucleic acids is hindered by low nucleic acid yields and artifacts of the analytical technique. For example, sequencing errors limit analytical sensitivity of mutation profiling of cfDNA.

There is thus a need for more sensitive and high-throughput methods to detect and monitor tumor-derived nucleic acids in cancer patients. The present invention addresses these and other needs in the art.

SUMMARY OF THE INVENTION

In one embodiment, the invention is a pool of unique adaptors for analyzing nucleic acids in a sample, each adaptor comprising: a double stranded portion at a proximal end and two single stranded portions at a distal end, wherein the double stranded portion comprises a double-stranded barcode of at least two base pairs specific to the adaptor, and wherein the single-stranded portion comprises: a pre-defined single-stranded barcode of at least two nucleotides specific to the sample; and a random single-stranded barcode of at least two nucleotides specific to the adaptor. The pool of adaptors may have the double-stranded portion further comprising one or more G/C base pairs between the double-stranded barcode of at least two base pairs and the proximal end of the adaptor. The pool of adaptors may also have the number of G/C base pairs that varies among the adaptors in the pool. The double-stranded barcode may comprise 2-20 base pairs. The pre-defined single-stranded barcode may comprise 4-20 nucleotides. The random single-stranded barcode may comprise 4-20 nucleotides.

In another embodiment, the invention is a method of analyzing nucleic acids comprising: attaching a pool of adaptors according to claims 1-6 to both ends of a plurality of double-stranded nucleic acids via the double stranded portions of the adaptors; amplifying both strands of the adaptor-nucleic acids to produce first amplicons and second amplicons, wherein the first amplicons are derived from a first strand of the double-stranded nucleic acids and contain a first strand of the double-stranded barcodes, and the second amplicons are derived from a second strand of the double-stranded nucleic acids and contain a second strand of the double-stranded barcodes; determining the sequence of the first and second amplicons; and determining whether the first and the second amplicons originate from a single double-stranded nucleic acid of the plurality of the double-stranded nucleic acids by means of identifying the double-stranded barcode. The plurality of double-stranded nucleic acids may comprise cell-free DNAs. The amplifying may comprise 12-14 cycles of PCR.

In another embodiment, the invention is a method of analyzing a plurality of double-stranded nucleic acids, the method comprising: attaching a pool of adaptors according to claims 1-6 to both ends of the plurality of double-stranded nucleic acids; amplifying both strands of the adaptor-nucleic acids to produce first amplicons and second amplicons, wherein the first amplicons are derived from a first strand of the double-stranded nucleic acids and contain a first strand of the double-stranded barcodes, and the second amplicons are derived from a second strand of the double-stranded nucleic acids and contain a second strand of the double-stranded barcodes; determining the sequence of the first and second amplicons; and identifying mutations in the first and second amplicon, wherein the mutation from the first and second amplicon are consistent mutations; or eliminating mutations that occur in the first but not the second amplicon; or eliminating G to T mutations that occur on at least about 90% of first amplicons derived from a first strand of a double-stranded nucleic acid, wherein the G to T mutations do not occur on less than about 10% of second amplicons derived from a second strand of the double-stranded nucleic acid; or eliminating mutations that are less than 100 base pairs from one another; or eliminating mutations that occur on less than about 50% of amplicons comprising the same pre-defined single stranded barcode and random single-stranded barcode; or any combination thereof. In this embodiment, the first amplicons and the second amplicons of c) comprise the same endogenous barcode and the same double-stranded barcode, and wherein the first amplicons and the second amplicons of c) comprise different random barcodes derived from the random single-stranded barcode of the adaptor. Further in this embodiment, the method may comprise eliminating mutations that are less than 5 base pairs from another. Further in this embodiment, the method may comprise eliminating mutations that occur on less than about 60%, about 70%, about 80%, about 90%, about 95%, or about 100% of amplicons comprising the same double-stranded stem barcode and the same endogenous barcode.

In another embodiment, the invention is a method of reduced-error analysis of nucleic acid comprising: attaching to each end of nucleic acids an adaptor from a pool of unique adaptors each adaptor comprising a double stranded portion at a proximal end and two single stranded portions at a distal end, wherein the double stranded portion comprises a double-stranded barcode of at least two base pairs specific to the adaptor, and wherein the single stranded portion containing a 5'-terminal nucleotide comprises: i) a pre-defined single-stranded barcode of at least two nucleotides specific to the sample; and ii) a random single-stranded barcode of at least two nucleotides specific to one strand of the adaptor; sequencing the nucleic acids with attached adaptors to determine sequence and if present, sequence variations of the nucleic acids; grouping the sequences of nucleic acids sharing the same random single-stranded barcode specific to one strand of the adaptor, to form barcode groups; eliminating sequence variations that are present in fewer than all members of the barcode group; eliminating sequence variations that are present at a frequency below a predetermined threshold among the barcode groups. The predetermined threshold may be 50%. The threshold may be predetermined according to a method comprising the steps of: performing single molecule sequencing of multiple samples to determine the target nucleic acid sequence; for each of the possible classes of nucleotide substitutions, determining a total number of substitutions (y) in all positions; and a number of supporting reads (t) for each position having a substitution; defining a function relating y to t; solving the function for the desired value of y by determining t, wherein t is the threshold number of reads above which the substitution may be called a sequence variation at the base position in the nucleic acid.

In another embodiment, the invention is a method of analyzing nucleic acids in a sample comprising: attaching to each end of nucleic acids an adaptor from a pool of unique adaptors each adaptor comprising a double stranded portion at a proximal end and two single stranded portions at a distal end, wherein the double stranded portion comprises a double-stranded barcode of at least two base pairs specific to the adaptor, and wherein the single stranded portion containing a 5' terminal nucleotide comprises: i) a pre-defined single-stranded barcode of at least two nucleotides specific to the sample; and ii) a random single-stranded barcode of at least two nucleotides specific to one strand of the adaptor; sequencing the nucleic acids with attached adaptors to determine sequence and if present, sequence variations of the nucleic acids; grouping the sequences of nucleic acids sharing the same random single-stranded barcode to form barcode groups; eliminating sequence variations that are present in fewer than all members of a barcode group; performing steps above on nucleic acids from control samples to identify recurrent sequence variations; applying statistical analysis to determine a confidence interval for the frequency of each sequence variation identified in the preceding step; setting a threshold for the frequency of sequence variations within the confidence interval of the preceding step; eliminating sequence variations whose frequency falls below the threshold set in the preceding step.

In yet another embodiment, the invention is a method of assessing a patient by analyzing patient's cell-free nucleic acids by the method described in the preceding paragraph, further comprising a step of assessing the patient as having cancer if one or more of the sequence variations is present after the elimination steps.

In yet another embodiment, the invention is a method of designing a selector comprising a plurality of target genomic regions to be analyzed in a sample of a patient having a type of tumor, the method comprising: performing sequencing of a genome of the type of tumor from multiple patients; identifying regions of the genome containing a mutation; ranking the regions identified in step b) based on the highest number of patients having a mutation per kilobase of sequence obtained in the first step; ranking the regions based on the highest number of patients having a mutation per exon; including the highest ranked regions from steps c) and d) in the selector. The genome sequencing may be exon sequencing. The regions identified by the method may be at least 100 base pairs long. The mutations may comprise single nucleotide variations, copy number variations, fusions, seed regions and histology classification regions. The highest ranked regions included in the selector comprise the top 10% of the highest ranking regions. The method may further comprise eliminating from the selector regions that fall into repeat-rich regions of the genome.

In yet another embodiment, the invention is a method of assessing cancer in a patient comprising: designing a selector as described above; obtaining a sample from a patient comprising cell-free nucleic acids; determining the sequence of genomic regions of the selector in the patient's nucleic acids; assessing the patient as likely to have cancer or recurrence of cancer if at least one sequence contains a mutation. The method may further comprise a confirmation of detected mutations as somatic in a matched tumor biopsy.

In yet another embodiment, the invention is a method of setting a threshold for calling a sequence variant at a base position in a target nucleic acid sequence containing nucleotide substitutions, the method comprising: performing single molecule sequencing of barcoded nucleic acids from multiple samples to determine the target nucleic acid sequence; for each of the possible classes nucleotide substitutions, determining a total number of substitutions (y) in all positions; a number of supporting reads (t) for the position having a substitution; defining a function relating y to t; solving the function for the desired value of y by determining t, wherein t is the threshold number of reads above which the substitution may be called a variant at the base position in the nucleic acid. The threshold t for a given sequence g among the plurality of target sequences may be adjusted for global error rate by a method comprising the steps of: determining error rate e for the plurality of target sequences equal to the number of base positions with nucleotide substitutions in a target sequence divided by the total number of bases in the target sequence; determining sequencing depth d for the plurality of target sequences; if e for sequence g falls within the top 25% of e of the plurality of target sequences, the threshold t for sequence g is adjusted to t' according to the formula: $t' \leftarrow t \times w$, where $w = \min\{q^2, 5\}$ and $q = e$ divided by the $75^{th}$ percentile of the error rates of sequences in the selector; if d for sequence g falls below the median of sequencing depths of the plurality of target sequences ($d^{med}$), the threshold t for sequence g is adjusted to t' according to the formula: $t' \leftarrow t/w^*$, where $w^* = \ln(d^{med}/d)$.

In yet another embodiment, the invention is a method of assessing a non-small cell lung cancer (NSCLC) patient by analyzing the patient's cfDNA to detect mutations with a selector and correcting for errors as described above and assessing the patient as assessing the patient as having NSCLC or having a progression of NSCLC if one or more of the sequence variations is present after error correction. The mutation may be a mutation in epidermal growth factor receptor (EGFR) gene located in the kinase domain (exon 19, 20 and 21) of the gene.

In yet another embodiment, the invention is a method of pairing nucleic acid sequencing reads to obtain a double-stranded nucleic acid sequence comprising: determining the sequence of plurality of single-stranded nucleic comprising insert sequences and adaptor sequences containing barcodes; determining genomic coordinates of the insert sequences; pairing the sequences into a double-stranded nucleic acid if the sequences have complementary barcodes and genomic coordinates of the insert map to the opposite strands. The method may further comprise a step of eliminating single-member barcode families containing a sequence variant unless the variant is supported by at least one other barcode family with members.

In another embodiment, the invention is a pool of unique adaptors for analyzing nucleic acids in a sample, each adaptor comprising: a double stranded portion at a proximal end and at least one single stranded portion at a distal end, wherein the double stranded portion comprises a double-stranded barcode of at least two base pairs specific to the adaptor, and wherein the single-stranded portion comprises: a pre-defined single-stranded barcode of at least two nucleotides specific to the sample; and a random single-stranded barcode of at least two nucleotides specific to the adaptor. Each adaptor may comprise two single-stranded portions at the distal end; one portion comprising a 5'-end and the other portion comprising a 3'-end, wherein the single stranded portions are non-hybridizable with each other. The two single stranded portions are covalently linked to each other at the distal ends, e.g., by a linker. The linker may optionally comprise a cleavage site. In some embodiments, the invention is a pool of unique adaptors comprising a combination of two sub-pools of adaptors: a first sub-pool wherein each adaptor comprises two single-stranded portions at the distal end: one portion comprising a 5'-end and the other portion comprising a 3'-end, wherein the single stranded portions are non-hybridizable with each other; and a second sub-pool wherein each adaptor comprises two non-hybridizable single-stranded portions that are covalently linked to each other at the distal ends.

In another embodiment, the invention is a method of reduced-error analysis of nucleic acid in a subject's sample comprising: performing single molecule sequencing nucleic acids from multiple control samples to determine the target nucleic acid sequence; determining the frequency of each of the possible classes of nucleotide substitutions at each position among the control samples; fitting a statistical model to these frequencies to determine frequencies of background errors; performing single molecule sequencing nucleic acids from the subject's sample; determining the frequency of each of the possible classes of nucleotide substitutions at each position in the subject's sample; determining the depth of reads for each target sequence in the subject's sample; applying the statistical model to the subject' sequence; eliminating nucleotide substitutions having frequencies below those of background errors.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

(FIG. 1A) End repair and A-tailing were performed on isolated cfDNA. (FIG. 1B) Y-shaped adaptors were attached to cfDNA. (FIG. 1C) The Y-shaped adaptor comprised a random barcode and a fixed barcode on its non-hybridizable portion, and a primer sequence on its hybridizable portion. (FIG. 1D) Template nucleic acids were amplified by PCR and the sequence information was obtained by next generation sequencing. * indicates real biological mutations. #indicates errors induced by PCR, etc. (FIG. 1E) False mutations were filtered out by bioinformatic analysis using barcodes. (FIG. 1F), (FIG. 1G) Sensitivity of mutations detection was enhanced from 0.02% to 0.001%.

(FIG. 2A) End repair and A-tailing were performed on isolated cfDNA. (FIG. 2B) Y-shaped adaptors were attached to cfDNA. (FIG. 2C) Each Y-shaped adaptor comprises a unique double-stranded barcode on the hybridizable portion. Arrows indicate stem barcodes.

FIG. 3A-3E: Endogenous barcodes comprise one or more sequences at different loci of the nucleic acid.

FIG. 5A-5C: Noninvasive and ultrasensitive detection of circulating DNA from solid tumors. (FIG. 5A) Selector design and validation. (FIG. 5B) Sensitivity modeling. (FIG. 5C) Cost optimization flow chart.

FIG. 8A-8E: Applicability of the selector to multiple types of tumors

(FIG. 9A) Tandem sequencing adaptors for error suppression and recovery in single and double stranded DNA molecules; (FIG. 9B) Heat map of position-specific selector-wide error rates; (FIG. 9C) Effect of barcode deduping and background polishing on selector-wide error metrics; (FIG. 9D) Density plots of the selector-wide LLOD for each base substitution; (FIG. 9E) Selector-wide detection limits for all possible base substitutions; (FIG. 9F) Comparison of iDES against different barcoding deduping strategies.

FIG. 11A-11E: Strand bias in stereotypical base substitution errors

(FIG. 12A) Comparison of three post-processing methods for biopsy-free genotyping; (FIG. 12B) observed and expected allele fractions; (FIG. 12C) heat map of detected SNVs; (FIG. 12D) White list variants in NSCLC patients detected with iDES; (FIG. 12E) Receiver Operating Characteristic (ROC) analysis of variants in FIG. 12D; (FIG. 12F) Recovery rates of actionable EGFR mutations from NSCLC tumors analyzed with iDES; (FIG. 12G) Comparison of post-processing methods for the detection of ctDNA; (FIG. 12H) Monitoring of tumor burden in a patient; (FIG. 12I) evaluation of the detection limit of duplex sequencing.

FIG. 15A-15F: Statistical framework for ctDNA detection and selector design. (FIG. 15A) ctDNA detection limits as a function of available tumor reporters; (FIG. 15B) ctDNA detection limits as a function of available tumor reporters and sequenced GEs for >90% detection likelihood; (FIG. 15C) distances between adjacent somatic mutations (source lung adenocarcinoma (LUAD), The Cancer Genome Atlas (TCGA); (FIG. 15D) Concordance between observed and predicted numbers of distinct tumor reporters; (FIG. 15E)

Analysis of the number of SNVs and indels per tumor covered by the NSCLC selector; (FIG. 15F) Reproducibility of each selector.

DETAILED DESCRIPTION OF THE INVENTION

Figure 1A:
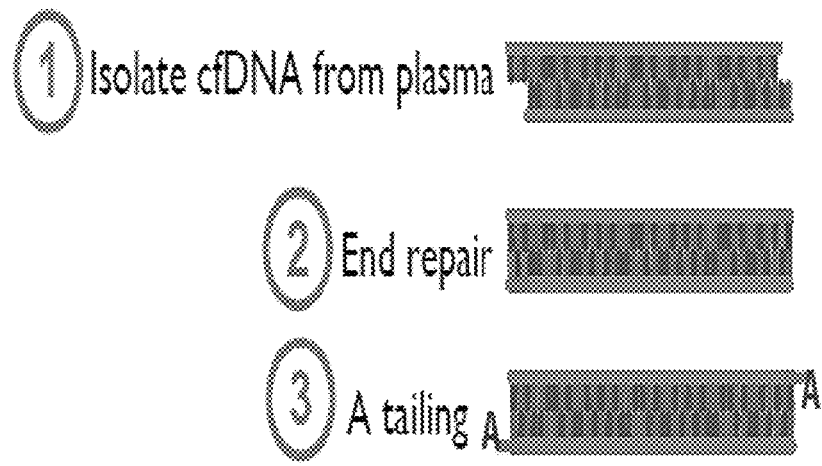
FIG. 1A-1G: Reducing background error with molecular barcoding.
Figure 1B:
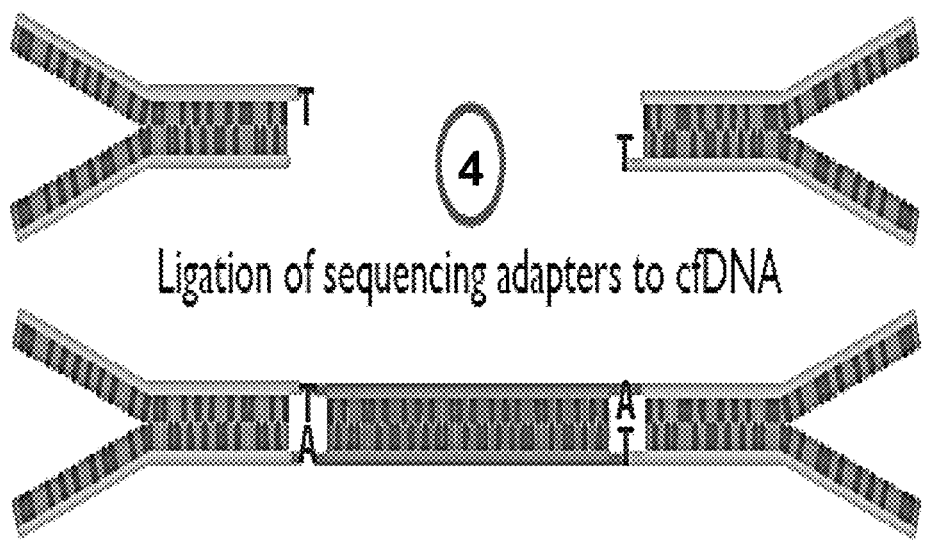
Figure 1C:
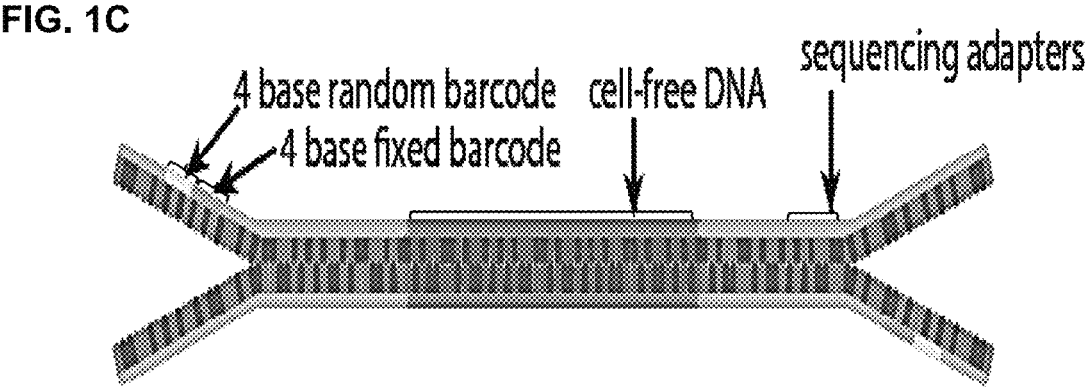
Figure 1D:
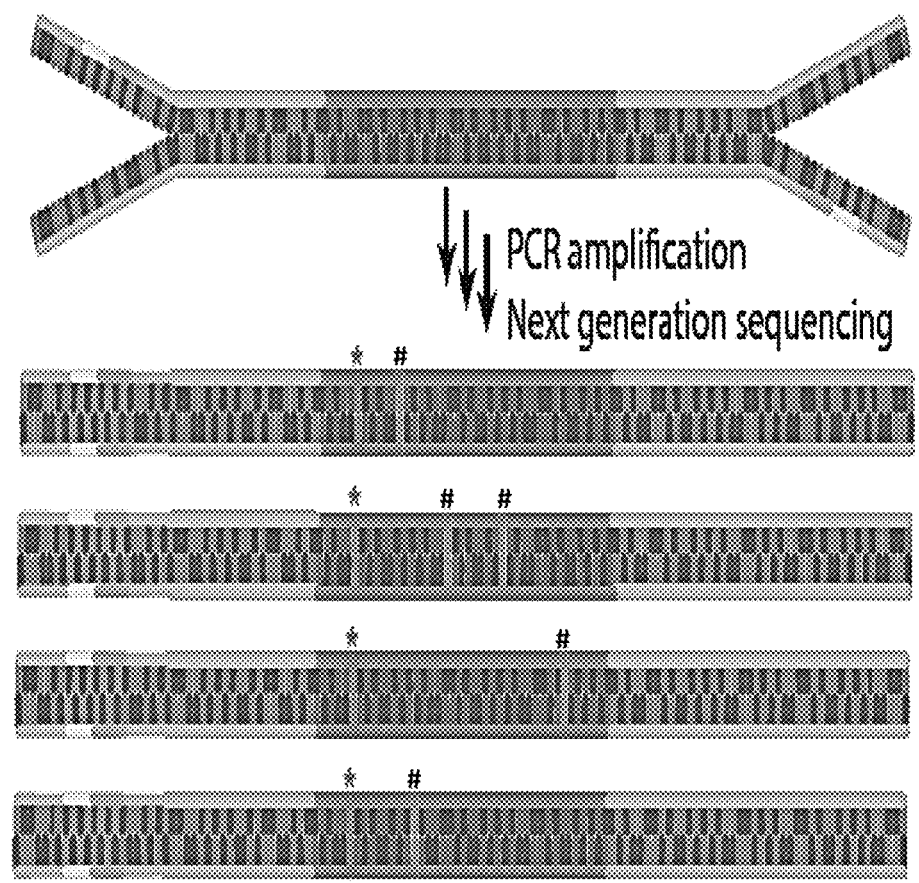
Figure 1E:
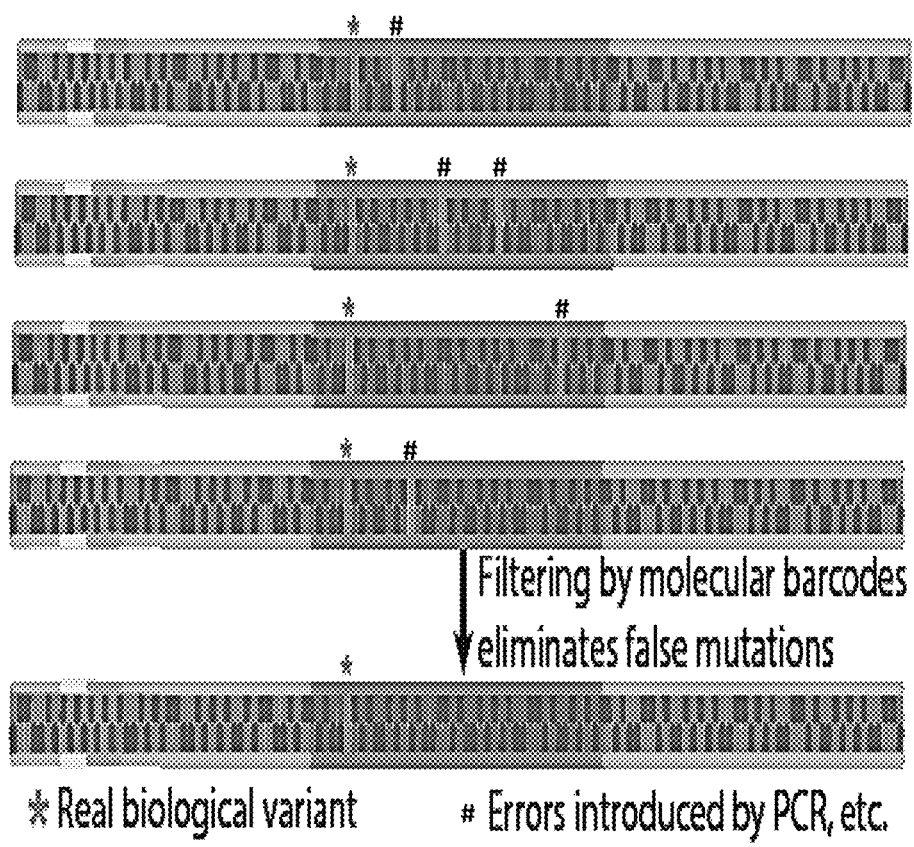
Figure 1F:
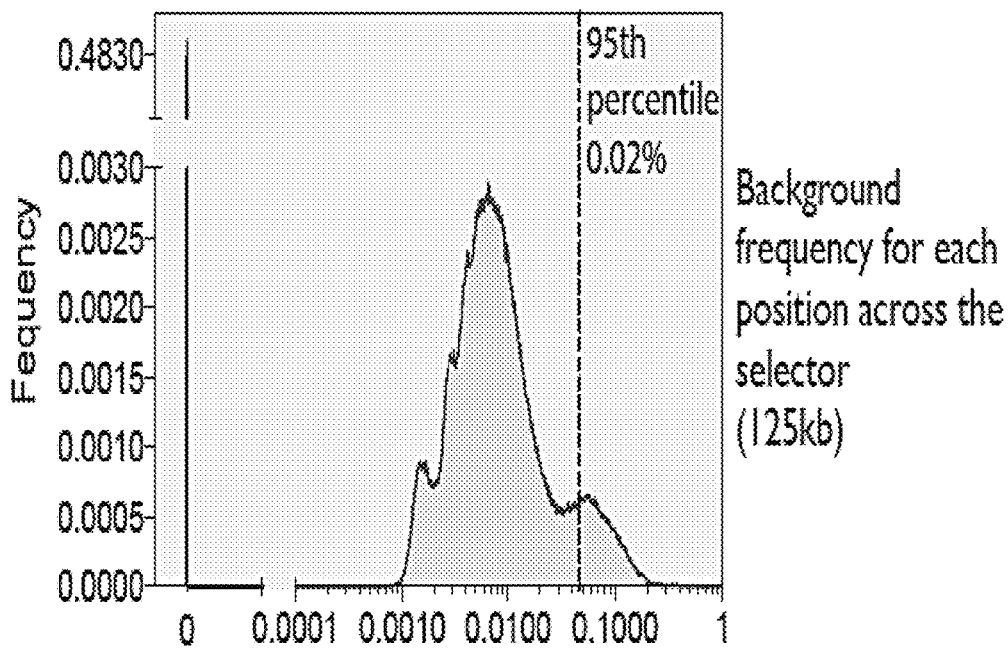
Figure 1G:
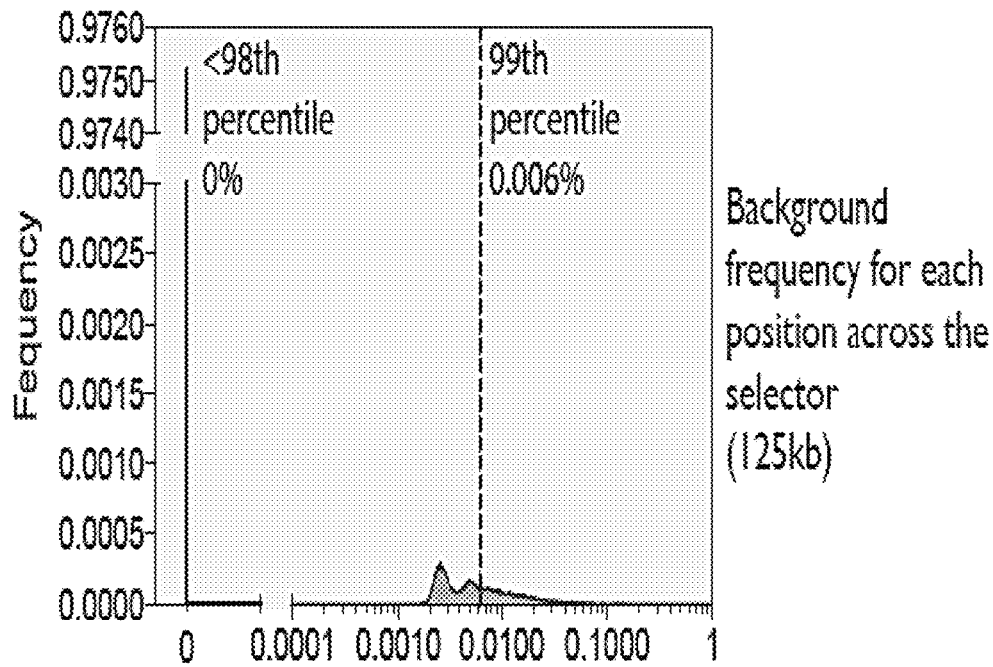

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

Definitions

The term "treating" includes achieving a therapeutic benefit and/or a prophylactic benefit. Therapeutic benefit can be eradication or amelioration of the underlying disorder being treated. Also, a therapeutic benefit can be achieved with the eradication or amelioration of one or more of the physiological symptoms associated with the underlying disorder such that an improvement can be observed in the patient, notwithstanding that the patient may still be afflicted with the underlying disorder. For prophylactic benefit, the compositions can be administered to a patient at risk of developing a particular disease, or to a patient reporting one or more of the physiological symptoms of a disease, even though a diagnosis of this disease may not have been made.

The term "adaptor" refers to a polynucleotide of known or unknown sequence that can be attached to either the 3' or 5' end of one or more polynucleotides. In some cases, the polynucleotide adaptor can be attached to another polynucleotide adaptor that is identical or different. The adaptor can comprise known sequences, unknown sequences, or both. A polynucleotide adaptor can be double-stranded or single-stranded. A double-stranded adaptor may comprise two hybridizable strands. Alternatively, an adaptor can comprise a hybridizable portion and a non-hybridizable portion. The non-hybridizable portion comprises at least one single stranded region, for example two single-stranded regions that are not hybridizable to each other. Within the non-hybridizable portion, the strand containing an unhybridized 5'-end is referred to as the 5'-strand and the strand containing an unhybridized 3'-end is referred to as the 3'-strand. The adaptor can have the hybridizable portion is at one end of the adaptor and the non-hybridizable portion is at the opposite end of the adaptor. The non-hybridizable portion may be open (Y-shaped adaptor) or covalently closed via a linker (BAL Seq adaptor).

The term "barcode" refers to a sequence of nucleotides within a polynucleotide that is used to identify a nucleic acid molecule. For example, a barcode can be used to identify molecules when the molecules from several groups are combined for processing or sequencing in a multiplexed fashion. Further, a barcode can be at certain position within a polynucleotide (e.g., at the 3'-end, 5'-end, or middle of the polynucleotide) and can comprise sequences of any length (e.g., 1-100 or more nucleotides). Additionally, a barcode can comprise one or more pre-defined sequences. The term "pre-defined" means that sequence of a barcode is predetermined or known prior to identifying or without the need to identify the sequence of the nucleic acid comprising the barcode. In some cases, pre-defined barcodes can be attached to nucleic acids for sorting the nucleic acids into groups. For example, a sequence of AAAA can be attached to identify nucleic acids isolated from Patient A. In some other cases, a barcode can also comprise one or more random sequences. The term "random" means that sequence of a barcode is not predetermined or is unknown prior to identifying. The term "random sequence" is used interchangeably with the term "degenerate sequence," i.e., the sequence not having a precise definition. For example, random barcodes can be attached to a nucleic acid as an identifier for the nucleic acid. In some cases, a barcode can comprise artificial sequences, e.g., designed sequences that are not contained in the unaltered genome of a subject. In some other cases, a barcode can comprise an endogenous sequence, e.g., sequences that are present in the unaltered genome of a subject. In certain cases, a barcode can be an endogenous barcode. An endogenous barcode can be a sequence of a genomic nucleic acid, where the sequence is used as a barcode or identifier for the genomic nucleic acid. Different types of barcodes can be used in combination. For example, a genomic nucleic acid fragment can be attached to a random barcode. One or more sequences of the genomic DNA fragment can be an endogenous barcode. Combination of the random barcode and the endogenous barcode can be used as a unique identifier of the genomic nucleic acid fragment.

The term "single-stranded barcode" means a barcode comprising a single-stranded sequence, e.g., a polynucleotide that is not bound to another polynucleotide by Watson-Crick hydrogen bonds. A double-stranded polynucleotide (e.g., a polynucleotide that is bound to another polynucleotide by Watson-Crick hydrogen bonds), for example, a double-stranded adaptor, can comprise a single-stranded barcode on one strand, where the barcode nucleotides do not have complementary nucleotides in the other strand of the polynucleotide. The term "double-stranded barcode" can mean a barcode comprising a double-stranded sequence, e.g., a polynucleotide barcode that is bound to another polynucleotide by Watson-Crick hydrogen bonds. In some instances the double stranded barcode can comprise a portion of a polynucleotide. A double-stranded adaptor can comprise one or more single-stranded barcodes and one or more double-stranded barcodes.

The term "hybridizable" means that two polynucleotide strands of a nucleic acid are complementary at one or more nucleotide positions, e.g., the nitrogenous bases of the two polynucleotide strands can form two or more Watson-Crick hydrogen bonds. For example, if a polynucleotide comprises 5'ATGC 3', it is hybridizable to the sequence 5' GCAT 3'. Under some experimental conditions, if a polynucleotide comprises 5' GGGG 3', the sequences 5'CCAC 3' and 5' CCCA 3', which are not perfectly complementary, can also be hybridizable.

The term "non-hybridizable" means that two polynucleotide strands of a nucleic acid are non-complementary, e.g., nitrogenous bases of the two separate polynucleotide strands do not form two or more Watson-Crick hydrogen bonds under standard hybridization conditions. For example, if a polynucleotide comprises 5'ATGC 3', the sequence 5' ATGC 3' can be non-hybridizable.

eThe term "assessing" comprises is used herein in reference to cancer or status of a patient with cancer and denote inferring the presence or the absence of tumors or tumor cells as well as with respect to the patient, recommending or not recommending therapy or treatments, evaluating or predicting effectiveness of therapy, monitoring the patient's condition, or evaluating prognosis of a cancer in a patient.

The term "diagnosing" means testing subjects to determine if the subjects have a particular trait for use in a clinical decision. Diagnosing can include testing of subjects at risk of developing a particular disease resulting from infection by an infectious organism or a non-infectious disease, such as cancer or a metabolic disease. Diagnosing can also include testing of subjects who have developed particular symptoms to determine the cause of the symptoms. The result of diagnosing can be used to classify patients into groups for performance of clinical trials for administration of certain therapies. For example, in some embodiments, diagnosing can comprise analyzing cfDNAs collected from subjects to detect the presence or absence of cancer-related mutations. In some other embodiments, diagnosing can comprise analyzing cfDNAs collected from subjects to monitor cancer progression or stages of cancer. In certain instances, diagnosing can also comprise analyzing cfDNAs collected from subjects receiving cancer treatments to detect the effect of the treatments and monitor cancer progression or stages of cancer during or after treatment.

The term "determining prognosis" means the testing of subjects to predict if they have a particular trait for use in a clinical decision. Determining prognosis can include testing of subjects at risk of developing a particular disease resulting from infection by an infectious organism or a non-infectious disease, such as cancer or a metabolic disease. For example, in some embodiments, determining prognosis can comprise analyzing cfDNAs collected from subjects to detect the presence or absence of cancer-related mutations. In some other embodiments, determining prognosis can comprise analyzing cfDNAs collected from subjects to monitor cancer progression or stages of cancer. In certain cases, determining prognosis can also comprise analyzing cfDNAs collected from subjects receiving cancer treatments to detect the effect of the treatments and monitor cancer progression or stages of cancer during or after treatment.

The term "amplification" refers to any method for increasing the number of copies of a nucleic acid sequence. For example, the amplification can be performed with the use of a polymerase, e.g., in one or more polymerase chain reactions (PCR) or another exponential or linear method of amplification.

The term "amplicons" means nucleic acid products of an amplification reaction. For example, the term "amplicons" may not include nucleic acid precursors that have not been incorporated into a desired nucleic acid product (e.g., unincorporated primers, dNTPs, etc.).

The terms "cancer," "neoplasm", and "tumor" can be used interchangeably herein and may refer to cells or tissues which exhibit autonomous, unregulated growth, such that the cells or tissues exhibit aberrant growth characterized by an increased cell proliferation, e.g., significant cell proliferation. Cells of interest for detection, analysis, or treatment in the present application may include, but are not limited to, precancerous (e.g., benign), malignant, pre-metastatic, metastatic, and non-metastatic cells. Cancers of virtually every tissue are known to those of skill in the art, including solid tumors such as carcinomas, sarcomas, glioblastomas, melanomas, lymphomas, myelomas, etc., and circulating cancers such as leukemias. Examples of cancer include, but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

The phrase "cancer burden" or "tumor burden" refers to the quantity of cancer cells or tumor volume in a subject. Reducing cancer burden accordingly may refer to reducing the number of cancer cells, or the tumor volume in a subject.

The term "cancer cell" refers to any cell that is a cancer cell or is derived from a cancer cell, e.g. clone of a cancer cell. The term "cancer cell" may also refer to a cell that exhibits cancer-like properties, e.g., uncontrollable reproduction, resistance to anti-growth signals, ability to metastasize, and loss of ability to undergo programmed cell death (e.g., apoptosis).

The term "deduping" refers to a method comprising grouping nucleic acid sequences into groups comprising progeny of a single molecule originally present in the sample. The original molecule and its progeny are characterized by the same unique molecular barcode (UID). Deduping further comprises analysis of the sequences of the progeny molecules to indirectly determine the sequence of the original molecule with a reduced rate of errors.

The term "mutation" refers to a genetic alteration in the genome of an organism or a cell. For example, mutations of interest can be changes relative to the germline of an organism, e.g., cancer cell-specific changes. Mutations may include single nucleotide variants (SNV), copy number variants (CNV), single nucleotide polymorphisms (SNP), insertions, deletions, and rearrangements (e.g., fusions).

The term "cancer-related mutations" refers to mutations that occur in tumor. For example, cancer-related mutations may be the cause of cancers. Cancer-related mutations may also facilitate cancer development, but not be the sole cause of cancer. Cancer-related mutations may also cause or facilitate cancer metastasis.

The term "cell-free DNA (cfDNA)" refers to DNA in a sample that when collected, was not contained within a cell. cfDNAs can comprise both normal cell and cancer cell-derived DNA. cfDNA is commonly obtained from blood or plasma ("circulation"). cfDNAs may be released into the circulation through secretion or cell death processes, e.g., cellular necrosis or apoptosis. Some cfDNA is ctDNA (see below).

The term "circulating tumor DNA (ctDNA)" or "circulating cancer DNA" refers to the fraction of cell-free DNA (cfDNA) that originates from a tumor.

The term "genome equivalents" refers to the amount of DNA necessary to comprise an entire genome.

The term "sample" refers to any biological sample that is isolated from a subject. For example, a sample can include, without limitation, an aliquot of body fluid, whole blood, platelets, serum, plasma, stool, red blood cells, white blood cells or leucocytes, endothelial cells, tissue biopsies, synovial fluid, lymphatic fluid, ascites fluid, and interstitial or extracellular fluid. The term "sample" may also encompass the fluid in spaces between cells, including gingival crevicular fluid, bone marrow, cerebrospinal fluid (CSF), saliva, mucus, sputum, semen, sweat, urine, or any other bodily fluids. The sample may also be a tumor sample. Samples can be obtained from a subject by means including but not limited to venipuncture, excretion, ejaculation, massage, biopsy, needle aspirate, lavage, scraping, surgical incision, or intervention or other means known in the art.

The term "blood sample" refers to whole blood or any fraction thereof, including blood cells: red blood cells, white blood cells or leucocytes, or platelets, or serum and plasma.

The term "genomic region" can refer to a range of sequences within a genome. For example, a genomic region can include a sequence in a gene or outside of a gene, e.g., an intron, a promoter, a non-coding region, etc.

The term "selector" refers to a plurality of oligonucleotides or probes that hybridize with one or more genomic regions. In some instances, the one or more genomic regions may be associated with diseases, e.g., cancers.

The term "attaching" refers to connecting two molecules by chemical bonds to generate a new molecule. For example, attaching an adaptor polynucleotide to another polynucleotide can refer to forming chemical bonds between the adaptor and the polynucleotide (e.g., using a ligase or any other method) to generate a single new molecule comprising the adaptor and the polynucleotide.

The term "locus" refers to a position in the genome. In some cases, a locus can be one or more nucleotides or one or more base pairs.

The term "polynucleotide" refers to a biopolymer that comprises one or more nucleotide monomers (natural or non-natural) covalently bonded in a chain. In some cases, a polynucleotide can have a sequence comprising genomic nucleic acid sequence. In other cases, a polynucleotide can have an artificial sequence (e.g., a sequence not found in genomic nucleic acid). A polynucleotide can comprise both genomic nucleic acid sequence or and an artificial sequence. An artificial sequence can contain non-natural nucleotides.

While specific genetic changes differ from individual to individual and between different types of cancer, there are regions of the genome that can show recurrent changes. In those regions there is an increased probability that any given cancer will show genetic variation. The genetic changes in cancer cells can provide a means by which cancer cells can be distinguished from normal (e.g., non-cancer) cells. For example, cfDNA can be analyzed for the presence of genetic variation distinctive of tumor cells. However, the absolute levels of cell-free tumor DNA in such samples is often low, and the genetic variation may represent only a very small portion of the entire genome. A method to address this issue includes accurate detection of cancer-related mutations in cancer cell nucleic acid in the background of normal cell nucleic acid. Although the methods disclosed herein may specifically refer to DNA or RNA, it is expressly contemplated that any nucleic acids can be substituted for DNA or RNA, or can be used in combination with one or more types of nucleic acids (e.g., RNA/DNA hybrids).

Y-Shaped Adaptors Comprising Unique Barcodes

Provided herein are compositions that can be used to identify or analyze nucleic acids. For example, in some embodiments, the composition can include a pool of Y-shaped adaptors, wherein each Y-shaped adaptor comprises a hybridizable portion at one end of the Y-shaped adaptor and a non-hybridizable portion at the opposite end of the Y-shaped adaptor, wherein the hybridizable portion comprises a unique identifiable double-stranded stem barcode of at least two base pairs.

Also provided herein are compositions that can include a pool of Y-shaped adaptors, wherein each Y-shaped adaptor comprises a hybridizable portion at one end of the Y-shaped adaptor and a non-hybridizable portion at the opposite end of the Y-shaped adaptor, wherein the non-hybridizable portion comprises i) a pre-defined single-stranded barcode of at least two nucleotides, and ii) a random single-stranded barcode of at least two nucleotides on the same strand as the pre-defined single-stranded barcode.

Further provided herein are compositions that can include a pool of Y-shaped adaptors, wherein each Y-shaped adaptor comprises a hybridizable portion at one end of the Y-shaped adaptor and a non-hybridizable portion at the opposite end of the Y-shaped adaptor, wherein the hybridizable portion comprises a unique double-stranded stem barcode of at least two nucleotides, and wherein the non-hybridizable portion comprises i) a pre-defined single-stranded barcode of at least two nucleotides, and ii) a random single-stranded barcode of at least two nucleotides on the same strand as the pre-defined single-stranded barcode.

To help in identifying the unique cancer nucleic acids, the adaptors in some embodiments can comprise a pre-defined single-stranded barcode and a random single-stranded barcode on the 5' strand of the non-hybridizable portion of the adaptor. On the other hand, in other embodiments, the pre-defined single-stranded barcode and the random single-stranded barcode can be on the 3' strand of the non-hybridizable portion of the adaptor.

The pre-defined single-stranded barcode can be adjacent to the random single-stranded barcode. It is also explicitly contemplated that the pre-defined single-stranded barcode can be separated from the random single-stranded barcode by one or more nucleotides.

The pre-defined single-stranded barcode may contain, naturally occurring bases (e.g., Adenosine (A), Thymidine (T), Guanosine (G), Cytosine (C), and Uracil (U)) or non-naturally occurring bases e.g., aminoallyl-uridine, iso-cytosines, isoguanine, and 2-aminopurine, and be between 1 and about 20 nucleotides long.

Similar to the pre-defined single stranded barcode, the length of the random barcode can be between 1 and about 20 nucleotides and it can contain naturally occurring bases (e.g., Adenosine (A), Thymidine (T), Guanosine (G), Cytosine (C), and Uracil (U)), or non-naturally occurring bases e.g., aminoallyl-uridine, iso-cytosines, isoguanine.

With regards to the length of the double-stranded stem barcode, it can also be between 1 and about 20 nucleotides.

In some cases, the double-stranded stem barcode can comprise pre-defined sequence. In other embodiments, the double-stranded stem barcode can comprise random sequence or comprise both a pre-defined sequence and a random sequence.

The double-stranded barcode can comprise natural and non-natural nucleotides, e.g., aminoallyl-uridine, iso-cytosines, isoguanine, and 2-aminopurine. This can assist in the detection of the double-stranded barcode.

In further embodiments, each Y-shaped adaptor can further comprise a primer sequence. The primer sequence may be a PCR primer sequence or a sequencing primer sequence. In some embodiments, the primer sequence can be on the non-hybridizable portion of the Y-shaped adaptor. In other embodiments, the primer sequence can be on the hybridizable portion of the Y-shaped adaptor. In some embodiments, the primer sequence can be the same in the entire Y-shaped adaptor pool. In some other embodiments, the primer sequences on one or more Y-shaped adaptors can be different from the primer sequences on other Y-shaped adaptors.

Methods of Analyzing Nucleic Acids

In some embodiments, the invention is a method of analyzing circulating tumor nucleic acids to detect a cancer-related mutation profile with high sensitivity. The method may be applied to cell-free DNA (cfDNA) containing circulating tumor DNA (ctDNA). The analyzing can comprise high-throughput sequencing of the nucleic acids. Disclosed herein is a novel analytical modeling framework for integrated digital error suppression (iDES) that enables sequencing nucleic acids with a low rate of error. The method of the present invention optimizes detection and analysis of ctDNA from low input samples. By combining suppression of stereotypical background errors with efficient molecular barcoding (iDES) delivers lower detection limits than previous methods across a broad range of sequencing methods thereby facilitating biopsy-free quantification of variants across hundreds of kilobases. In some embodiments, the sensitivity of the ctDNA analysis is as low as 1-3 mutant molecules per typical sample. In some embodiments, the method is applied to advanced non-small cell lung cancer (NSCLC) and enables biopsy-free detection of 95% of activating mutations in the EGFR gene without false positives. In some embodiments, the method allows recovery of ctDNA fractions as low as 0.004% in a monitoring context. In yet other embodiments comprises Moreover, by leveraging reconstructed duplex sequences the method enables the detection limit of 2.5 molecules in the background of 1,000,000 molecules.

Disclosed herein are methods of analyzing nucleic acids, including the methods for the ultrasensitive detection of nucleic acids, e.g., circulating cell-free DNA, for example, circulating cell-free tumor DNA in a sample. The method accurately quantifies nucleic acids, e.g., cell-free tumor DNA, from early and advanced stage tumors. Because tumor-derived DNA levels often parallel clinical responses to diverse therapies, the method may identify actionable mutations. The method may also be used to noninvasively detect and monitor tumors, thus facilitating personalized cancer therapy.

The adaptors used in the method of the invention are shown in FIG. 6. The method of the invention may utilize Y-shaped adaptors or covalently closed adaptors can also be used. In covalently closed adaptors, the single-stranded portions may be connected via a linker. The method of the invention can also utilize a combination of Y-shaped and covalently closed adaptors.

The method can comprise a) attaching double-stranded adaptors to both ends of a plurality of double-stranded nucleic acids to produce adaptor-ligated nucleic acids, wherein each of the double-stranded adaptors comprises a double-stranded stem barcode; b) amplifying both strands of the adaptor-ligated nucleic acids to produce first amplicons and second amplicons, wherein the first amplicons are derived from a first strand of the double-stranded nucleic acids and a first strand of the double-stranded stem barcodes, and the second amplicons are derived from a second strand of the double-stranded nucleic acids and a second strand of the double-stranded stem barcodes; c) ascertaining the sequence of the first and second amplicons; and d) analyzing the nucleic acids using the double-stranded stem barcode.

Analyzing may include determining whether the first and the second amplicons originate from the same strand of a single double-stranded nucleic acid of the plurality of the double-stranded nucleic acids by means of identifying the double-stranded stem barcode.

Also disclosed herein are methods comprising a) attaching adaptors via their double-stranded portions to both ends of a plurality of double-stranded nucleic acids to produce adaptor-ligated nucleic acids, wherein each adaptor comprises a hybridizable portion at one end and a non-hybridizable portion at the opposite end, and wherein the hybridizable portion of each of the double-stranded adaptors comprises a double-stranded stem barcode; b) amplifying both strands of the adaptor-ligated nucleic acids to produce first amplicons and second amplicons, wherein the first amplicons are derived from a first strand of the double-stranded nucleic acids and a first strand of the double-stranded stem barcodes, and the second amplicons are derived from a second strand of the double-stranded nucleic acids and a second strand of the double-stranded stem barcodes; c) ascertaining the sequence of the first and second amplicons; and d) using the double-stranded stem barcode, determining whether the first and the second amplicons originate from the same strand of a single double-stranded nucleic acid of the plurality of the double-stranded nucleic acids.

Also disclosed herein are methods comprising a) attaching adaptors via their double-stranded portions to both ends of a plurality of double-stranded nucleic acids to produce adaptor-ligated nucleic acids, wherein each adaptor comprises a hybridizable portion at one end and a non-hybridizable portion at the opposite end, wherein the hybridizable portion comprises a double-stranded stem barcode, and wherein the non-hybridizable portion comprises a 5' strand comprising: i) a pre-defined single-stranded barcode of at least two nucleotides; and ii) a random single-stranded barcode of at least two nucleotides on the same strand as the pre-defined single-stranded barcode, wherein one or more sequences of each double-stranded nucleic acid provides an endogenous barcode of the nucleic acid, and wherein combination of the random single-stranded barcode and the endogenous barcode provides a unique identifier for each double-stranded nucleic acid; b) amplifying both strands of the adaptor-ligated nucleic acids to produce first amplicons and second amplicons, wherein the first amplicons are derived from a first strand of the double-stranded nucleic acids and a first strand of the double-stranded stem barcodes, and the second amplicons are derived from a second strand of the double-stranded nucleic acids and a second strand of the double-stranded stem barcodes; c) ascertaining the sequence of the first and second amplicons; and d) determining whether the first and the second amplicons originate from the same strand of a single double-stranded nucleic acid of the plurality of the double-stranded nucleic acids by identifying the sequence of the double-stranded stem barcode.

Disclosed herein are methods for analyzing nucleic acids for detecting, diagnosing, or determining prognosis of cancer. The methods can comprise a) attaching adaptors via their double-stranded portions to both ends of a plurality of double-stranded nucleic acids to produce adaptor-ligated nucleic acids, wherein each adaptor comprises a hybridizable portion at one end and a non-hybridizable portion at the opposite end, wherein the hybridizable portion comprises a unique identifiable double-stranded stem barcode of at least two nucleotides, and wherein the non-hybridizable portion comprises i) a pre-defined single-stranded barcode of at least two nucleotides; and ii) a random single-stranded barcode of at least two nucleotides on the same strand as the pre-defined single-stranded barcode; b) amplifying the template nucleic acids to produce a plurality of amplicons; c) hybridizing the amplicons with a selector comprising a set of oligonucleotides that selectively hybridize to genomic regions of all or a subset of the one or more sample nucleic acids; and d) obtaining sequences of the hybridized amplicons to detect presence or absence of cancer or cancer-related mutations.

Disclosed herein are methods for analyzing nucleic acids for detecting, diagnosing, or determining prognosis of cancer. The methods can comprise a) attaching adaptors via their double-stranded portions to both ends of a plurality of double-stranded nucleic acids to produce adaptor-ligated nucleic acids, wherein each adaptor comprises a hybridizable portion at one end and a non-hybridizable portion at the opposite end, wherein the hybridizable portion comprises a unique identifiable double-stranded stem barcode of at least two nucleotides, and wherein the non-hybridizable portion comprises i) a pre-defined single-stranded barcode of at least two nucleotides; and ii) a random single-stranded barcode of at least two nucleotides on the same strand as the pre-defined single-stranded barcode; b) amplifying the template nucleic acids to produce a plurality of amplicons; c) hybridizing the amplicons with a selector comprising a set of oligonucleotides that selectively hybridize to genomic regions of all or a subset of the one or more sample nucleic acids; and d) obtaining sequences of the hybridized amplicons to detect presence or absence of cancer or cancer-related mutations.

The methods of the invention comprise the step of attaching of one molecule to another molecule, e.g., a polynucleotide adaptor onto a different polynucleotide. The attaching may comprise ligating Y-shaped adaptors to one or more nucleic acids. In some cases, the enzyme used in the ligation is a DNA ligase, e.g., a T4 DNA ligase, E. coli DNA ligase, mammalian ligase, or any combination thereof. The mammalian ligase may be DNA ligase I, DNA ligase III, or DNA ligase IV. The ligase may also be a thermostable ligase.

Adaptors Used in the Method

The adaptors disclosed herein and their specific embodiments can be attached to the one or more nucleic acids through the hybridizable (double-stranded) portion of the adaptors. The adaptors can have free or linked single stranded portions. In some embodiments, the method of the invention utilizes adaptors with free single stranded portions (Y-shaped adaptors) and covalently linked single-stranded portions (BAL-Seq adaptors) or a combination of two types of adaptors (FIG. 6). In some embodiments, the covalently linked single-stranded portions are linked by a linker. The linker may optionally contain a cleavage site, e.g., a restriction enzyme recognition sequence.

The adaptors of the present invention may have barcodes located according to several distinct embodiments described below. As shown in FIG. 6, each adaptor may have several barcodes (referred to as "ID" in FIG. 6). The adaptors may have one or more barcodes on each single-stranded portion and one or more barcodes in the double stranded portion. In reference to FIG. 6, in some embodiments, the single stranded portions have molecular ID barcodes and the double-stranded portion may have sample ID barcodes. Each of the barcodes can be located (or co-located) in (a) upper single stranded region (containing the 5'-end), (b) lower single stranded region (containing the 3'-end), and (c) the double-stranded region or stem of the Y-shaped adaptor as shown in Table A and FIG. 6.

TABLE A

Placement of barcodes and use in sequencing

| Upper SS | Lower SS | DS (Stem) | SS Sequencing? | DS Sequencing? |
|---|---|---|---|---|
| M, U | | | yes | no |
| | M, U | | yes | no |
| M, U | M, U | | yes | yes* |
| | | M, U | yes | yes |

TABLE A-continued

Placement of barcodes and use in sequencing

| Upper SS | Lower SS | DS (Stem) | SS Sequencing? | DS Sequencing? |
|---|---|---|---|---|
| M | | U | yes | yes |
| U | | M | yes | no |
| | U | M | yes | no |
| U | U | M | yes | yes* |

M: multiplex sample ID (MID);
U: unique molecular ID (UID);
SS—single stranded;
DS—double stranded
*DS Sequencing, i.e., pairing two strands using barcodes is only possible if barcodes are not random but have known sequences so they could be matched.

In some embodiments, the UIDs are on both strands of the adaptor: the upper and the lower strands, or in the double stranded region. If the UIDs can be matched as originating from the same adaptor, double strand sequencing (i.e., pairing single strands is possible). The UIDs located in the double stranded region are matched by Watson-Crick pairing. The known-sequence (not random) UIDs present on the single stranded portions can be cross-referenced as belonging to the same adaptor molecule.

In some embodiments, the random single-stranded barcode combined with an endogenous barcode can provide a unique identifier for each template nucleic acid. The endogenous barcode can comprise a sequence of any length and can comprise one or more sets of nucleotide sequences on a nucleic acid. The sequences could be at different loci of the nucleic acid. In some embodiments, the endogenous barcode can comprise a sequence on an end of the nucleic acid (FIG. 3 (a)). In some embodiments, the endogenous barcode can comprise a first sequence on an end of the nucleic acid and a second sequence on the opposite end of the nucleic acid (FIG. 3 (b)). In other embodiments, the endogenous barcode can comprise an internal sequence (FIG. 3 (c)). In certain embodiments, the endogenous barcode can comprise a first sequence that is internal, and a second sequence that is on one end of the nucleic acid (FIG. 3 (d)). In still other embodiments, the endogenous barcode can comprise a first and a second sequence that are both internal (FIG. 3 (e)).

In the context of the invention, the amplicons derived from the same template nucleic acid contain the same unique identifier (UID). These distinct unique identifiers can be used to identify and count the distinct template nucleic acids in the original sample. For example, UIDs can be used to count original template nucleic acids containing the same mutations. In other cases, UIDs can be used to identify and group the amplicons from the same original template nucleic acid.

The stem barcode can be in any portion of the stem of the adaptor. For example, the stem barcode can be adjacent to the base pair to which the adaptor attaches on the nucleic acid or one or more base pairs away from the base pair to which the adaptor attaches on the nucleic acid.

The unique double-stranded stem barcodes can also identify strands of the nucleic acid. For example, after an adaptor is attached to a nucleic acid, both strands of the resulting nucleic acid contain the unique stem barcode, even though each strand of the nucleic acid may contain different random single-stranded barcodes or different unique identifier. After amplification, the amplicons derived from one strand of the nucleic acid contain the same stem barcode and the same endogenous barcode as the amplicons derived from the other strand of the same nucleic acid. Thus, in some embodiments, the stem barcode can be used to identify amplicons derived from the two strands of the same template nucleic acid. In certain embodiments, the unique stem barcodes can be used to identify mutations on one strand, but not the other strand, of the nucleic acid. In some other embodiments, mutations that occur on one strand, but not the other strand, of the template nucleic acid can be amplification errors and can be disregarded as artifact.

In some embodiments, the invention comprises a novel adaptor molecule. Disclosed herein are "tandem" sequencing adaptors containing two fundamentally distinct barcodes, which allow tracking of individual DNA molecules to distinguish real somatic mutations arising in vivo from errors introduced during ex vivo procedures including high-throughput sequencing. Adaptors may comprise barcodes that include a defined sequence or a random sequence or a combination of a random sequence and a defined sequence. As shown on FIG. 1 and FIG. 6, the single stranded portion of the adaptor includes a barcode consisting of a multiplex sample ID (MID) portion shared among the adaptor molecules in a sample and a barcode unique to each adaptor molecule (unique ID or UID). In some embodiments, the unique barcode is a random barcode. Adaptors with such compound barcodes are referred to as "index adaptors." In some embodiments, the adaptors are "tandem adaptors." Tandem adaptors comprise index adaptors with added nucleotides. In some embodiments, 2 or more bases are added to each end of each adaptor oligonucleotide to yield a tandem adaptor. In some embodiments, the added nucleotides include a T at the 3'-end to enable ligation. In other embodiments, the adaptors are "staggered tandem adaptors." Staggered tandem adaptors comprise tandem adaptors with added nucleotides. In some embodiments, 2 or more bases are added distal to the internal end of the adaptor. (FIG. 6).

Figure 7A:
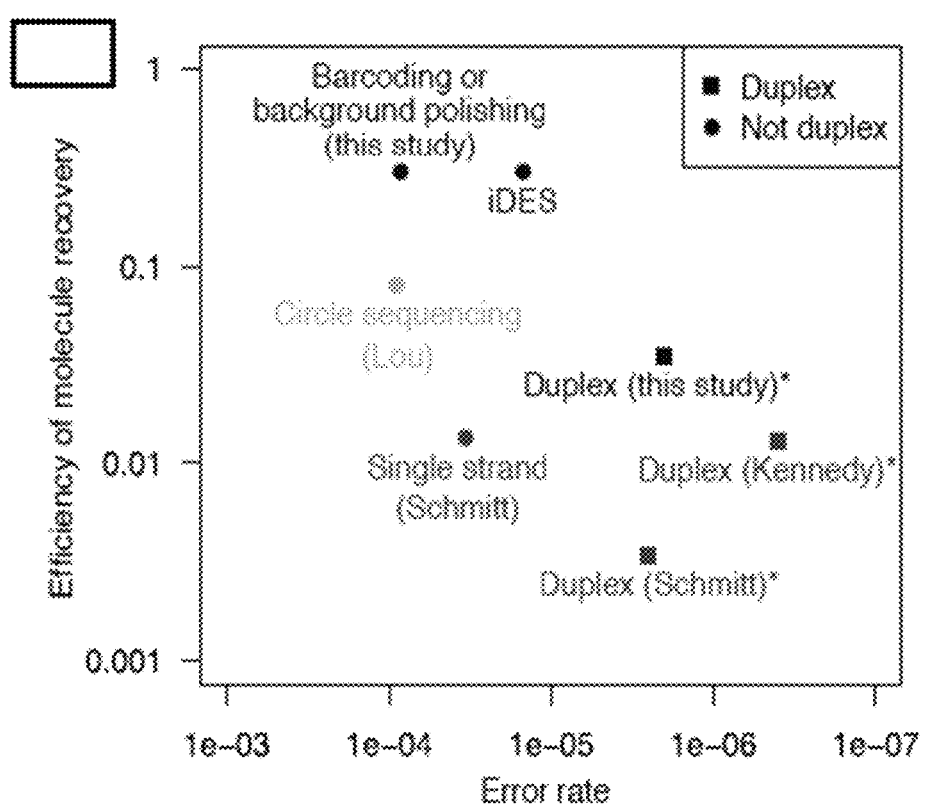
FIG. 7A-7B: Design and performance of Integrated Digital Error Suppression (iDES)
Figure 7B:
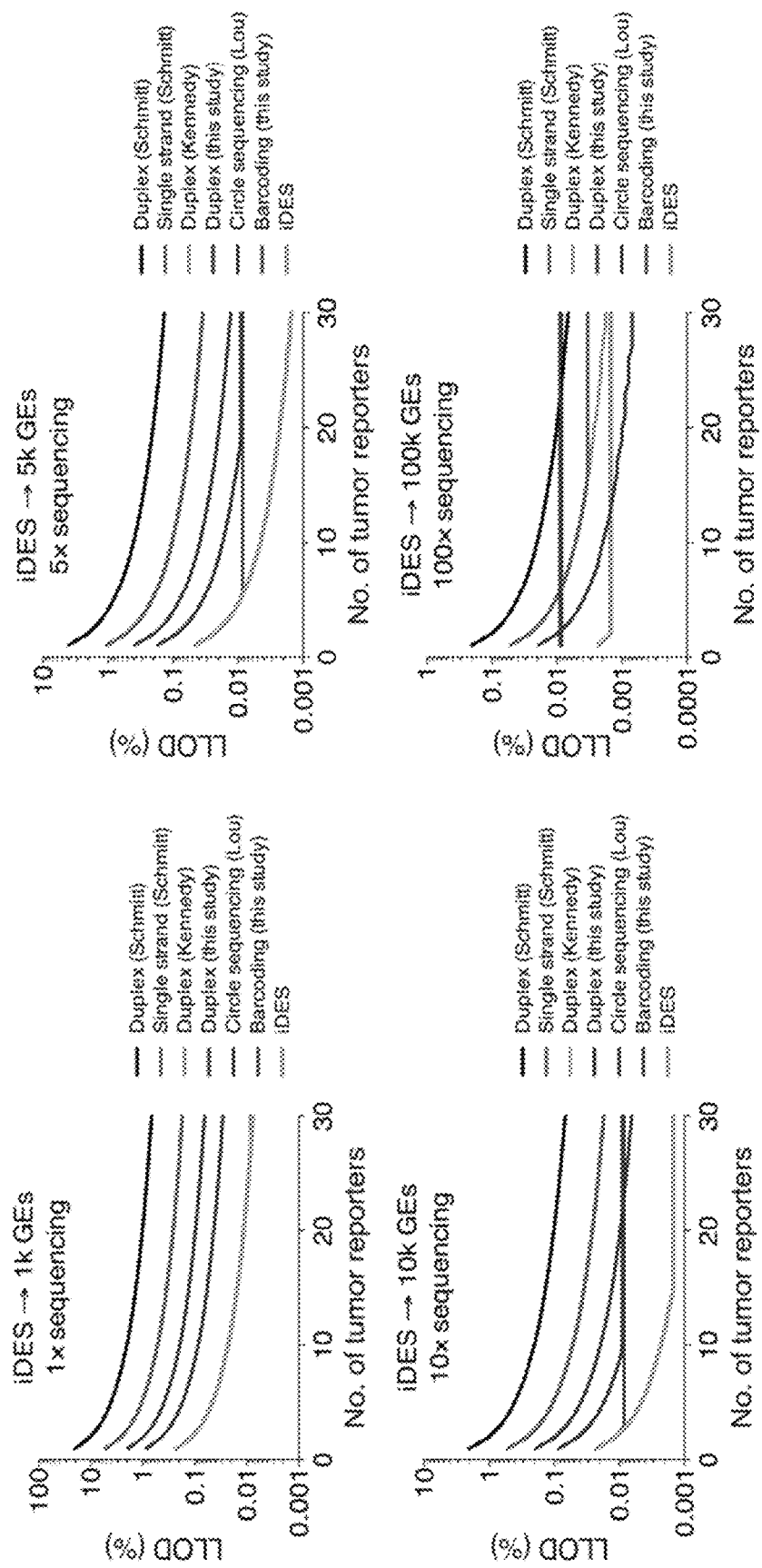

In some embodiments of the adaptor, a typical sample multiplexing barcode (MID) is replaced with a degenerate molecular barcode as a unique identifier, or UID. In another embodiment, a short UID (2 or more nucleotides) near the ligating end of the adaptor creates an "insert" or internal barcode or internal UID. (FIG. 6 (*a*)). By leveraging the distinct genomic coordinates of each molecule, the internal UIDs of the instant invention allow for shorter barcodes, maximizing sequencing throughput. These internal UIDs allow for efficient recovery of duplex molecules, improving by ~2-fold on similar prior art approaches, see (FIG. 7 (*a*)). The method of the present invention (i.e., iDES, barcoding or polishing only, duplex only) compared favorably with error suppression methods from the prior art. (FIG. 7 (*a*)) referring to Lou, D. I., et al. *High-throughput DNA sequencing errors are reduced by orders of magnitude using circle sequencing. Proc Natl Acad Sci USA* 110, 19872-19877 (2013), ("Lou"); Kennedy, S. R. et al. *Detecting ultralow-frequency mutations by Duplex Sequencing. Nat Protoc* 9, 2586-2606 (2014), ("Kennedy"); and Schmitt, M. W., et al. *Detection of ultra-rare mutations by next-generation sequencing. Proc Natl Acad Sci USA* 109, 14508-14513 (2012), ("Schmitt".)

Tandem Adaptors and Staggered Tandem Adaptors

In some embodiments, the invention is a method of barcoding designed to maximize usable sequencing depth within a sequencing read. Instead of inserting a unique molecular barcode (UID) into the read of the target sequence, the molecular barcode was placed near the sample barcode (MID) so that the molecular barcode is read in a separate "index" read. This allowed the both paired-end sequencing reads to be used entirely for reading the DNA bases from the target nucleic acids, in contrast to other molecular barcoding methods which require sacrificing 15 or more of the sequenced bases of each read to the barcodes (Kennedy, S. R. et al. *Detecting ultralow-frequency mutations by Duplex Sequencing. Nat Protoc* 9, 2586-2606 (2014)). Another advantage of the method of the invention is that the sequencing adaptors used herein are otherwise unmodified, This design of the adaptors of the present invention allows for efficient ligation during library preparation in contrast to the lower efficiency of library preparation reported with other methods that use what? (Kennedy, supra). In some embodiments, the length of the random barcode is designed to allow for a sufficient number of distinct barcodes that are different enough from each other to be used simultaneously. For example, a random 2-mer allows for 16 distinct molecular barcodes, while a random 4-mer allows for 256 distinct molecular barcodes. In some embodiments, a random barcode is combined with the genomic coordinates of the fragment starts and ends to form an endogenous or internal barcode. Taken together, the endogenous barcode can provide a sufficiently complex pool of unique molecular barcodes (UID). In the context of this disclosure, sufficient complexity means a number of barcodes sufficient to differentiate the expected number of identical input molecules. For example, one of skill in the art can determine the number of unique nucleic acid molecules (or human genome equivalents) based on the typical size and content of a patient's sample. In this context, one of skill in the art can determine the expected number of nucleic acid molecules obtained from a certain volume of cell-free human plasma sample and thus determine the required number of unique barcodes. In some embodiments, the adaptor also has a multiplex sample barcode (MID). In some embodiments, the MID has sufficient length to design the number of barcodes needed to use the desired number of samples. For example, 4 bases-long multiplexing barcode allows the design of 24 multiplexing barcodes with pairwise edit distances of at least 2.

In some embodiments, the invention is a method of sequencing nucleic acids with a reduced error rate using index barcoding. The method of the invention involves correct pairing of reads from opposite strands of the same duplex molecule. In this embodiment, the invention uses barcodes at the end of each strand of the adaptor molecule. In some embodiments, these barcodes are one or more bases, for example 2 bases long. The barcodes appear at each end of the paired end reads. As is shown in FIG. 6 (*a*), there are 2-base punctuation marks comprising a base pair in the adaptor (G/C pair) and a base pair in the target molecule (A/T pair) resulting from the ligation step described herein. We called these adaptors tandem adaptors to reflect the fact that they contain both multiplex sample barcodes (MID) and unique molecular barcodes (UID). In some embodiments, the unique molecular barcodes are as short as possible. In some embodiments, the unique molecular barcodes are 1 or 2 bases long. For example, having 2-base barcodes maximized informative sequencing content while still allowing differentiation of unique molecules. The present invention discloses a method of analyzing maximized length of a nucleic acid in a single read. In some embodiments, only 8 bases in a pair of reads were used up by barcodes and punctuation, in contrast to 30 or more bases in each pair of reads used by prior art methods (Kennedy, supra).

As the tandem adaptors of the present invention contain both multiplex sample barcodes (MID) and unique molecular barcodes (UID), the invention comprises a method of using both to achieve a synergistic result. In some embodiments, the method comprises combining the two strategies (UID deduping followed by MID deduping) to achieve the lowest error rate. (FIG. 6(b)).

In some embodiments, the method is utilizing single-stranded reads while in other embodiments, the method is utilizing double-stranded reads, i.e., reads of molecules for which the two strands have been sequenced and paired. As demonstrated by Examples, the method of the present invention achieved the low error rate with double stranded reads. The observed error rate of $2\times10^{-6}$ (See Example 18) is better than with nearly all previously seen error suppression mechanisms (Kukita, Y., et al. *High-fidelity target sequencing of individual molecules identified using barcode sequences: de novo detection and absolute quantitation of mutations in plasma cell-free DNA from cancer patients.* DNA Research (2015); Kinde, I., et al. *Detection and quantification of rare mutations with massively parallel sequencing.* Proc Natl Acad Sci USA 108, 9530-9535 (2011); Lou, D. I., et al. *High-throughput DNA sequencing errors are reduced by orders of magnitude using circle sequencing.* Proc Natl Acad Sci USA 110, 19872-19877 (2013), and similar to error rates seen previously using duplex sequencing (Kennedy and Schmitt, supra).

The results further demonstrate that the method of the invention is superior to the state of the art at recovering duplex molecules. The duplex molecules were recovered at about twice the rate as previously reported with as many as 3.3% duplex molecules among total reads sequenced.

In some embodiments, the invention utilizes single stranded molecules or molecules without dual strand support. As shown in Examples, sequencing with iDES increased recovery of molecules by an order of magnitude, while maintaining the error rate at $1.5\times10^{-5}$, which is still better than published non-duplex molecular barcode error suppression techniques (FIG. 7(a), Example 18).

In some embodiments, the adaptors were designed to have a combination of 2- and 4-base barcodes. It is known in the art that it is beneficial to have substantial sequence diversity within the pool of nucleic acids to be sequenced. Where such diversity is lacking (due to e.g., non-random fragmentation of nucleic acids or the use of short barcodes) the sample may be spiked with a pool of high-diversity nucleic acids (e.g., PhiX library offered by Illumina, San Diego, Calif.). In some embodiments, the invention includes the use of staggered tandem adaptors that have more diversity than tandem adaptors. Staggered tandem adaptor pool comprises a combination of adaptors with 2-base barcodes and 4-base barcodes. As shown in Examples, the error rate found with staggered adaptors was at least as good as the error rate with tandem adaptors and a spike of PhiX (FIG. 6(c), Example 12).

Samples

The methods disclosed herein may comprise analyzing one or more samples. A sample can be any biological sample isolated from a subject, for example, an aliquot of body fluid, whole blood, platelets, serum, plasma, stool, red blood cells, white blood cells or leucocytes, endothelial cells, tissue biopsies, synovial fluid, lymphatic fluid, ascites fluid, interstitial fluid or and/or extracellular fluid. A sample may also encompass the fluid in spaces between cells, including gingival crevicular fluid, bone marrow, cerebrospinal fluid (CSF), saliva, mucus, sputum, semen, sweat, urine, or any other bodily fluids. A blood sample can be whole blood or any fraction thereof, including blood cells (red blood cells, white blood cells or leucocytes, and platelets), serum and plasma. Samples can be obtained from humans or non-humans.

The sample may also be a tumor sample. Tumor samples can be obtained from a subject by means including but not limited to venipuncture, excretion, massage, biopsy, needle aspirate, lavage, scraping, surgical incision, or intervention or other means known in the art.

Other sample sources can include sweat, breath, tears, and/or amniotic fluid. For example, the sample may be a cerebral spinal fluid sample. In some instances, the sample is not a Pap smear fluid sample. In some instances, the sample is not a cyst fluid sample. In some instances, the sample is not a pancreatic fluid sample.

Samples may be collected from individuals repeatedly over a period of time (e.g., once a day, once a week, once a month, biannually or annually). Obtaining numerous samples from an individual over a period of time can be used to verify results from earlier detections or to identify an alteration as a result of, for example, drug treatment.

The sample may comprise nucleic acids. The nucleic acids may be tumor nucleic acids. The nucleic acids may also be circulating nucleic acids, e.g., cell-free nucleic acids. For instance, the circulating nucleic acids may be from a tumor, e.g., ctDNA. The nucleic acids may be genomic nucleic acids.

Sample nucleic acids useful for the methods of the invention may comprise cfDNAs, e.g., DNA in a sample that is not contained within a cell. Such DNA may be fragmented, e.g., may be on average about 170 nucleotides in length, which may coincide with the length of DNA wrapped around a single nucleosome.

cfDNA may be a heterogeneous mixture of DNA from normal and tumor cells, and an initial sample of cfDNA may not be enriched for cancer cell DNA and recurrently mutated regions of a cancer cell genome. The terms circulating tumor DNA (ctDNA) or cell-free tumor DNA may be used to refer to the fraction of cfDNA in a sample that is derived from a tumor. One of skill in the art will understand that non-mutated germline sequences may not be distinguished between a tumor source and a normal cell source, but sequences containing somatic mutations have a probability of being derived from tumor DNA. In some cases, a sample may comprise control germline DNAs. A sample may also comprise known tumor DNAs. Further, a sample may comprise cfDNAs obtained from an individual suspected of having ctDNA in the sample. Additionally, a sample may comprise cfDNAs obtained from an individual not suspected of having ctDNA in the sample, for example, as part of routine testing.

The methods disclosed herein may comprise obtaining one or more samples, e.g., nucleic acid samples, from a subject. The one or more sample nucleic acids may be tumor nucleic acids. For example, nucleic acids may be extracted from tumor biopsies. Tumor nucleic acids may also be released into the blood stream from tumor cells, e.g., as a result of immunological responses to the tumor. The tumor nucleic acid that is released into the blood can be ctDNA.

The one or more sample nucleic acids may be genomic nucleic acids. It should be understood that the step of obtaining tumor nucleic acids and genomic nucleic acids from a subject with a specific cancer may occur simultaneously. For example, venipuncture to collect blood, plasma, or serum, may simultaneously collect both genomic and tumor nucleic acids. Obtaining tumor nucleic acids and genomic nucleic acids from a subject with a specific cancer may also occur at separate occasions. For example, it may be possible to obtain a single tissue sample from a patient, for example, a biopsy sample, which includes both tumor nucleic acids and genomic nucleic acids. It is also possible to obtain the tumor nucleic acids and genomic nucleic acids from the subject in separate samples, in separate tissues, or at separate times.

Obtaining tumor nucleic acids and genomic nucleic acids from a subject with a specific cancer may also include the process of extracting a biological fluid or tissue sample from the subject with the specific cancer.

Obtaining the nucleic acids may include procedures to improve the yield or recovery of the nucleic acids, such as separating the nucleic acids from other cellular components and contaminants that may be present in the biological fluid or tissue sample, e.g. by phenol chloroform extraction, precipitation by organic solvents, or DNA-binding spin columns. As noted above, this may improve the yield and may facilitate the sequencing reactions.

Obtaining tumor nucleic acids and genomic nucleic acids from a subject with a specific cancer may also be performed by a commercial laboratory that may not have direct contact with the subject. For example, the commercial laboratory may obtain the samples from a hospital or other clinical facility where the sample is obtained from a subject. The commercial laboratory may thus carry out all the steps of the instantly-disclosed methods at the request of, or under the instructions of, the facility where the subject is being treated or diagnosed.

Sometimes, the nucleic acids are mixed or impure. Therefore, if identifying the source of nucleic acids is desired, the pre-defined single-stranded barcode can be used to sort the nucleic acids into different groups. For example, the pre-defined single-stranded barcode may be used to identify a sample from which the nucleic acid originated. In some cases, nucleic acids from a first sample may be associated with a first pre-defined single-stranded barcode, whereas nucleic acids from a second sample may be associated with a second pre-defined single-stranded barcode. In other cases, the pre-defined single-stranded barcodes of two or more samples may be different. In some other cases, the two or more samples may be from the same subject. In certain embodiments, the two or more samples may be from different tissues of the same subjects. For example, one sample may be from a tumor and another sample may be from the blood of the same subject, where the tumor may be a solid tumor. Additionally, the two or more samples may be from two or more subjects. The samples may be obtained at the same time or at two or more time points.

Amplification

Nucleic acid amplification can result in the incorporation of nucleotides into a nucleic acid molecule or primer thereby forming a new nucleic acid molecule complementary to a template nucleic acid. The newly formed nucleic acid molecule and its template can be used as templates to synthesize additional nucleic acid molecules. The nucleic acids being amplified can be DNAs, including genomic DNAs, cDNAs (complementary DNA), cell-free DNAs (cfDNAs) and circulating tumor DNAs (ctDNAs). The nucleic acids being amplified can also be RNAs. As used herein, one amplification reaction may consist of many rounds of DNA synthesis.

The methods disclosed herein may comprise amplification of the template nucleic acids comprising sample nucleic acids attached to Y-shaped adaptors. Any known techniques for nucleic acid (e.g., DNA and RNA) amplification can be used with the assays described herein. Some amplification techniques are the polymerase chain reaction (PCR) methodologies which can include, but are not limited to, solution PCR and in situ PCR. Alternatively, amplification may comprise non-exponential amplification, such as linear amplification.

Amplification of the template nucleic acids may comprise using bead amplification followed by fiber optics detection as described in U.S. Applications Pub. Nos. 20020012930, 20030058629, 20030100102, 20030148344, 20040248161, 20050079510, 20050124022, and 20060078909.

Amplification of the template nucleic acid may comprise use of one or more polymerases. For example, the polymerase may be a DNA polymerase or an a RNA polymerase. In some cases, the polymerase may be a high fidelity polymerase, KAPA HiFi DNA polymerase. The polymerase may also be Phusion DNA polymerase.

Selector Design

Somatic mutations, which are mutations that occur in any of the cells of the body except the germ-line cells, can be characteristic of cancer cells. Most human cancers are relatively heterogeneous for somatic mutations in individual genes. A selector can be used to enrich tumor-derived nucleic acid molecules from total genomic nucleic acids. The design of the selector can dictate which mutations can be detected in with high probability for a patient with a given cancer. The selector size can also directly impact the cost and depth of sequence coverage. For example, design and use of selectors are described in part in PCT Application No. PCT/US14/25020 (US20140296081) and Newman et al. (2014), Nat Med. 20(5):548-54), incorporated herein by reference in their entirety.

The methods disclosed herein may comprise one or more selector or uses of the one or more selector. A selector may comprise a plurality of oligonucleotides or probes that hybridize with one or more genomic regions. The genomic regions may comprise one or more mutated regions. The genomic regions may comprise one or more mutations associated with one or more cancers.

The plurality of genomic regions may comprise different genomic regions. In some embodiments, the plurality of genomic regions may comprise from a few to up to 5000 different genomic regions.

A genomic region may comprise a protein-coding region, or a portion thereof. A protein-coding region may refer to a region of the genome that encodes a protein, e.g., a gene. A gene may also comprise non-coding sequences, such as an intron, or untranslated region (UTR) or portions thereof. A genomic region may comprise two or more genes, protein-coding regions, or portions thereof. In some instances, a genomic region does not comprise an entire gene.

A genomic region may comprise a non-protein-coding region. In some cases, a non-protein-coding region may be transcribed into a non-coding RNA (ncRNA). In some cases, the non-coding RNA may have a known function. For example, the noncoding RNA may be a transfer RNA (tRNA), ribosomal RNA (rRNA), or regulatory RNA, small nuclear RNA (snRNA), small nucleolar RNA (snoRNA), microRNA, small interfering RNA (siRNAs), Piwi-interacting RNA (piRNA), and long ncRNA (e.g., Xist, HOTAIR). A genomic region may comprise a pseudogene, a transposon, or a retrotransposon.

A genomic region may comprise a recurrently mutated region. A "recurrently mutated region" may refer to a region of the genome, usually the human genome, in which there is an increased probability of genetic mutation in a cancer of interest, relative to the genome as a whole. A recurrently mutated region may refer to a region of the genome that comprises one or more mutations that is recurrent in the population. A recurrently mutated region may be characterized by a "Recurrence Index" (RI). The RI generally refers to the number of individual subjects (e.g., cancer patients) with a mutation that occurs within a given kilobase of genomic sequence (e.g., number of patients with mutations/ genomic region length in kb). A genomic region may also be characterized by the number of patients with a mutation per exon. Thresholds for each metric (e.g., RI and patients per exon or genomic region) may be selected to statistically enrich for known or suspected drivers of the cancer of interest, e.g., NSCLC. Thresholds can also be selected by arbitrarily choosing the top percentile for each metric.

The number of genomic regions in a selector may vary depending on the nature of the cancer. The inclusion of larger numbers of genomic regions may generally increase the likelihood that a unique somatic mutation will be identified. However, including too many genomic regions in the library is not without a cost. For example, the number of genomic regions can be directly related to the length of nucleic acids that may be sequenced in the analysis. At the extreme, the entire genome of a tumor sample and a genomic sample could be sequenced, and the resulting sequences could be compared to note any differences with the non-tumor tissue.

The selectors of the invention may address this problem by identifying genomic regions that are recurrently mutated in a particular cancer, and then ranking those regions to maximize the likelihood that the region will include a distinguishing somatic mutation in a particular tumor. The library of recurrently mutated genomic regions, or "selector", can be used across an entire population for a given cancer or class of cancers, and does not need to be optimized for each subject.

The method may further comprise a hybridization reaction, e.g., hybridizing the amplicons with a selector comprising a set of oligonucleotides that selectively hybridizes to genomic regions of one or more sample nucleic acids. In some embodiments, the hybridization reaction may comprise hybridizing the plurality of nucleic acids to the solid support, e.g., a plurality of beads.

The method may further comprise conducting a hybridization reaction after an enzymatic reaction. For example, in some cases, the enzymatic reaction may comprise one or more of a ligation reaction, a fragmentation reaction, an end repair reaction, an A-tailing reaction, or an amplification reaction.

The selector may also comprise a set of oligonucleotides. The set of oligonucleotides may hybridize to less than 100 kb and up to 1.5 Megabases (Mb) of the genome.

The set of oligonucleotides may be capable of hybridizing to 5 and up to 500 or more different genomic regions.

The selector may also hybridize to a range of different genomic regions, e.g., to between about 10 to about 1000 different genomic regions. The selector may also hybridize to a plurality of genomic regions, e.g., to 50 to at most 5000 different genomic regions.

A selector may hybridize to a genomic region comprising a mutation that is not recurrent in the population. For example, a genomic region may comprise one or more mutations that are present in a given subject. In some instances, a genomic region that comprises one or more mutations in a subject may be used to produce a personalized selector for the subject.

The selector may hybridize to a plurality of genomic regions comprising one or more mutations selected from a group consisting of SNV, CNV, insertions, deletions, and rearrangements.

A selector may hybridize to a mutation in a genomic region known to be associated with a cancer. The mutation in a genomic region known to be associated with a cancer may be referred to as a "known somatic mutation". A known somatic mutation may be a mutation located in one or more genes known to be associated with a cancer. A known somatic mutation may be a mutation located in one or more oncogenes. For example, known somatic mutations may include one or more mutations located in p53, EGFR, KRAS or BRCA1.

A selector may hybridize to a mutation in a genomic region predicted to be associated with a cancer. Further, a selector may hybridize to a mutation in a genomic region that has not been reported to be associated with a cancer.

A genomic region may comprise a sequence of the human genome of sufficient size to capture one or more recurrent mutations. A genomic region may be said to "identify a mutation" when the mutation is within the sequence of that genomic region. The methods of the invention may be directed at cfDNA, which is generally less than about 200 bp in length, and thus a genomic region may be generally less than about 10 kb. Generally the genomic region for a SNV can be quite short, from about 45 to about 500 bp in length, while the genomic region for a fusion or other genomic rearrangement may be longer, from about 1 Kbp to about 10 Kbp in length. A genomic region in a selector may be less than 10 Kbp, for example, 100 bp to 10 Kbp.

In some embodiments, the total sequence covered by the selector is less than about 1.5 megabase pairs (Mb), e.g., 10 kb-1.5 Mb.

In some embodiments, the invention comprises an improved design of a selector that improves sensitivity of detecting tumor mutations (variants) in a patient's sample. The selector used in the method of the invention comprises variants obtained from whole genome sequencing of tumors. Optionally, the selector may exclude variants located in regions containing repeats or other technical obstacles. For example, the list of variants can be obtained from exome-sequencing nucleic acids from collections of tumor samples, such as a collection of lung squamous cell carcinoma (SCC) tumors or lung adenocarcinoma tumors or any other collections of one or more types of tumors available for sequencing analysis. The sequences may be filtered to eliminate variants located in repeat-rich genomic regions (such as for example, simple repeats, microsatellites, interrupted repeats and segmental duplications). The sequences may also (or instead) be filtered to eliminate variants located in intervals with low mapping rates or low k-mer uniqueness.

According to the method of the invention, selectors used in the method are designed to cover as many patients and mutations per patient as possible with the least amount of genomic space. In some embodiments, the invention includes a method of creating a selector, i.e., selecting genomic regions to be analyzed in a patient. The genomic regions are included based on experimental steps described below. The selectors are designed to prioritize inclusion of genomic regions based on the "recurrence index" (RI) metric defined herein. In some embodiments, genomic regions to be included in the selector are exons or smaller portions of an exon containing known lesions. A genomic region to be included comprises the known lesion and is flanked by one or more base pairs to a minimum tile size of 100 bp. According to the method of the invention, genomic regions are ranked by decreasing RI, and those in the highest ranks of both RI and the number of patients per exon are included in the selector. In some embodiments, the highest rank is higher or equal to top 10%. In this embodiment, the selector has maximized additional patient coverage with minimal space. In some embodiments, the process of selecting genomic regions is repeated under reduced stringency, i.e., the percentile rank lower than top 10%, e.g., top 33% are selected. In this embodiment, the method results in including regions that maximally increase the median number of mutations per patient. In some embodiments, inclusion of further genomic regions into a selector is terminated when a predetermined size is reached. In some embodiments, the predetermined desired size is about 100-200 kb (e.g., 175 kb for the NSCLC cfDNA selector). In other embodiments, inclusion of further genomic regions into a selector is terminated when all genomic regions satisfying the filters described above are exhausted.

In some embodiments, the selector comprising genomic regions containing single nucleotide variations (SNVs) as described above further comprises clinically relevant regions containing other types of mutations, e.g., fusions, seed regions, copy number variations (CNVs) and histology classification regions.

Clinical Indications

The method provided herein may further comprise obtaining sequence information of the hybridized amplicons to detect presence or absence of cancer. For example, sequence information can be the actual nucleotide sequence or in some cases the number of copies of genes.

In some cases, the cancer may be a solid tumor. For example, the solid tumor may be non-small cell lung cancer (NSCLC). The cancer may also be a breast cancer. For example, the breast cancer may be associated with mutations in the BRCA genes, e.g., BRCA1.

The selector can be designed for a specific cancer, for example, non-small cell carcinoma, endometrial uterine carcinoma, etc. The selector can also be designed for a generic class of cancers, e.g., epithelial cancers (carcinomas), sarcomas, lymphomas, melanomas, gliomas, teratomas, etc. The selector can also be designed for a subgenus of cancers, e.g., adenocarcinoma, squamous cell carcinoma, and the like.

The selector may also comprise information pertaining to a plurality of genomic regions comprising one or more mutations present in at least one subject suffering from a cancer. For example, the selector may comprise information pertaining to a plurality of genomic regions comprising up to 20 mutations present in at least one subject suffering from a cancer. In some cases, the selector may comprise information pertaining to a plurality of genomic regions comprising up to 200 or more mutations present in at least one subject suffering from a cancer.

The selector may comprise information pertaining to a plurality of genomic regions comprising one or more mutations present in at least one subject suffering from a cancer. In some cases, the one or more mutations within the plurality of genomic regions may be present in at least 1% and up to 20% or more (e.g., up to 95% or more) subjects from a population of subjects suffering from a cancer.

Sequencing

Genotyping, detection, identification or quantitation of the ctDNA can utilize sequencing. Sequencing can be accomplished using high-throughput systems. Sequencing can be performed using nucleic acids described herein such as genomic DNA, cDNA derived from RNA transcripts or RNA as a template. For example, sequence information of the cell-free DNA sample may be obtained by massively parallel sequencing. In some cases, massively parallel sequencing may be performed on a subset of a genome, e.g., from a subset of cfDNA from the cfDNA sample. Sequence information can be obtained by parallel sequencing using flow cells. For example, primers for amplification can be covalently attached to slides in the flow cells and then the flow cells can be exposed to reagents for nucleic acids extension and sequencing. High-throughput sequencing can also involve the use of technology available from Helicos BioSciences Corp. (Cambridge, Mass.) such as the Single Molecule Sequencing by Synthesis (SMSS) method. In some embodiments, high-throughput sequencing involves the use of technology available by 454 Life Sciences, Inc. (Branford, Conn.) such as the Pico Titer Plate device which includes a fiber optic plate that transmits chemiluminescent signal generated by the sequencing reaction to be recorded by a CCD camera in the instrument. This use of fiber optics allows for the detection of a minimum of 20 million base pairs in 4.5 hours.

In some cases, the high-throughput sequencing can be next generation sequencing technique, e.g., using the HiSeq or MiSeq instruments available from Illumina (San Diego, Calif.) This sequencing method is based on the amplification of DNA on a solid surface using fold-back PCR and anchored primers. The sequencing can involve a library preparation step. Genomic DNA can be fragmented, and sheared ends can be repaired and adenylated. Adaptors can be added to the 5' and 3' ends of the fragments. The fragments can be size selected and purified. The sequencing can comprise a cluster generation step. DNA fragments can be attached to the surface of flow cell channels by hybridizing to a lawn of oligonucleotides attached to the surface of the flow cell channel. The fragments can be extended and clonally amplified through bridge amplification to generate unique clusters. The fragments become double stranded, and the double stranded molecules can be denatured. Multiple cycles of the solid-phase amplification followed by denaturation can create several million clusters of approximately 1,000 copies of single-stranded DNA molecules of the same template in each channel of the flow cell. Reverse strands can be cleaved and washed away. Ends can be blocked, and primers can by hybridized to DNA templates. Hundreds of millions of clusters can be sequenced simultaneously. Primers, DNA polymerase and four fluorophore-labeled, reversible terminator nucleotides can be used to perform sequential sequencing. All four bases can compete with each other for the template. After nucleotide incorporation, a laser can be used to excite the fluorophores, and an image is captured and the identity of the first base is recorded. The 3' terminators and fluorophores from each incorporated base are removed and the incorporation, detection and identification steps are repeated. A single base can be read each cycle. In some embodiments, a HiSeq system (e.g., HiSeq 2500, HiSeq 1500, HiSeq 2000, or HiSeq 1000) is used for sequencing.

High-throughput sequencing of RNA or DNA can also take place using AnyDot-chips (Genovoxx, Germany), which allows monitoring of biological processes (e.g., miRNA expression or allele variability (SNP detection)). For example, the AnyDot-chips allow for 10×-50× enhancement of nucleotide fluorescence signal detection. Other high-throughput sequencing systems include those disclosed in Venter, J., et al. Science 16 Feb. 2001; Adams, M. et al., Science 24 Mar. 2000; and M. J, Levene, et al. Science 299:682-686, January 2003; as well as U.S. Application Pub. No. 2003/0044781 and 2006/0078937. The growing of the nucleic acid strand and identifying the added nucleotide analog may be repeated so that the nucleic acid strand is further extended and the sequence of the target nucleic acid is determined.

The methods disclosed herein can comprise conducting a sequencing reaction based on one or more genomic regions from a selector.

In some cases, the sequencing information may be obtained for a subset of genomic regions from a selector. For example, sequencing information may be obtained for 10-500 or more genomic regions from a selector.

In some cases, sequencing information may be obtained for less than 5%, or up to 95% of the genomic regions from a selector.

End Repair

The embodiments of the method may comprise performing an end repair reaction on the plurality of nucleic acids to produce a plurality of end repaired nucleic acids. For example, the end repair reaction may be conducted prior to attaching the adaptors to the plurality of nucleic acids.

In some cases, the end repair reaction may be conducted prior to amplification of the adaptor-modified nucleic acids. In other cases, the end repair reaction may be conducted after amplification of the adaptor-modified nucleic acids.

In some embodiments, the end repair reaction may be conducted prior to fragmenting the plurality of nucleic acids. In other embodiments, the end repair reaction may be conducted after fragmenting the plurality of nucleic acids.

The end repair reaction may also be performed by using one or more end repair enzymes. In some cases, enzymes for repairing DNA can comprise polymerase and exonuclease. For example, polymerase can fill in the missing bases for a DNA strand from 5' to 3' direction. The resulting double-stranded DNA can be the same length as the original longest DNA strand. Exonuclease can remove the 3' overhangs. The resulting double-stranded DNA can be the same length as the original shortest DNA strand.

A-Tailing

The embodiments of the method may comprise performing an A-tailing reaction on the plurality of nucleic acids to produce a plurality of A-tailed nucleic acids. For example, the A-tailing reaction may be conducted prior to attaching the adaptors to the plurality of nucleic acids.

Further, the A-tailing reaction may be conducted prior to amplification of the adaptor-modified nucleic acids. In other cases, the A-tailing reaction may be conducted after amplification of the adaptor-modified nucleic acids.

In some embodiments, the A-tailing reaction may be conducted prior to fragmenting the plurality of nucleic acids. In some cases, the A-tailing reaction may be conducted after fragmenting the plurality of nucleic acids.

In other cases, the A-tailing reaction may be conducted prior to end repair of the plurality of nucleic acids. In some embodiments, the A-tailing reaction may be conducted after end repair of the plurality of nucleic acids.

The A-tailing reaction may also be performed by using one or more A-tailing enzymes. For example, an A residue can be added by incubating a DNA fragment with dATP and a non-proofreading DNA polymerase, which will add a single 3' A residue.

Reducing Background Error

The method provided herein may further comprise methods of reducing background error. Background errors may comprise mutations that do not occur in vivo but are artificially generated, e.g., during amplification or sequencing. Background error mutations, for example, single nucleotide changes, e.g., guanine to thymine (G to T) mutations, may be caused by errors of PCR or sequencing. These mutations occur on one strand of a double-stranded nucleic acid but do not occur on the other strand. These artificial G to T mutations can be detected and disregarded.

Also disclosed herein are methods for reducing background error in sequence of a plurality of amplicons derived from a plurality of nucleic acids, comprising a) identifying mutations from at least a first sequence read and at least a second sequence read, where the mutation from the first sequence read and second sequence read are consistent mutations; b) eliminating mutations that occur on less than 50% of amplicons derived from a single nucleic acid; c) eliminating G to T mutations that occur on first amplicons derived from a first strand of a double-stranded nucleic acid, where the G to T mutations do not occur on second amplicons derived from a second strand of the double-stranded nucleic acid; d) eliminating mutations that are less than 100 base pairs from one another; e) eliminating mutations on amplicons, where a first subset of the amplicons comprises a first double-stranded stem barcode and a second subset of the amplicons comprise a second double-stranded stem barcode, where the first double-stranded stem barcode is different from the second double-stranded stem barcode; or f) any combination thereof. The term "eliminating" as used herein can refer to disregarding mutation data from the sequence information.

The reducing background error can comprise identifying mutations from at least a first sequence read and at least a second sequence read, wherein the mutation from the first sequence read and second sequence read are consistent mutations. In this case, the mutation can be a real mutation, e.g., not background error.

In some embodiments, a mutation of a nucleotide identified from a first sequence read of one strand of a double-stranded nucleic acid is consistent with a mutation of the nucleotide identified from a second sequence read of the same strand of the double-stranded nucleic acid. For example, if the mutations are real, e.g., are not background errors, an A mutation (e.g., a nucleotide mutated to A) identified from a sequence read of one strand of a double-stranded nucleic acid should be consistent with an A mutation (e.g., a nucleotide mutated to A) identified from a sequence read of the same strand of the double-stranded nucleic acid.

In other embodiments, a mutation of a nucleotide identified from a first sequence read of one strand of a double-stranded nucleic acid is consistent with a mutation of a complementary nucleotide identified from a second sequence read of the other strand of the double-stranded nucleic acid. For example, if the mutations are real, e.g., are not background errors, an A mutation (e.g., a nucleotide mutated to A) identified from a sequence read of one strand of a double-stranded nucleic acid should be consistent with a T mutation (e.g., a nucleotide mutated to T) identified from a sequence read of the other strand of the double-stranded nucleic acid.

Reducing background error may comprise identifying consistent mutations from 2 or more, e.g. up to 20 or more sequence reads.

Mutations that are considered to be background error in the sequence information can randomly occur on various loci, and thus, may not be present on all the amplicons containing a locus of the mutations. Amplicons that contain the same locus of a mutation can be identified by the pre-defined single-stranded barcodes on the amplicons, the random single-stranded barcodes on the amplicons, or any combination thereof. In some embodiments, amplicons that contain the same locus of a mutation can be amplicons containing the same unique identifier. In another embodiment, bioinformatic analysis can be performed to remove the mutations that do not occur on all the amplicons containing the same locus.

Background error may comprise mutations that do not occur on all amplicons derived from a single nucleic acid. For example, reducing background error may comprise eliminating mutations that occur on less than about 50% to less than about 75% or less than about 100% of the amplicons derived from a single nucleic acid or below an experimentally determined cut-off level.

Spatial Proximity of Mutations

Some mutations that are background errors can be close to one another, e.g., exist in a close spatial proximity. For example, reducing background can comprise removing, e.g., disregarding, mutations that are adjacent to one another. In other embodiments, reducing background error may comprise removing mutations that are one or less base pairs from one another or up to 100 base pairs from another.

Amplicons derived from a single nucleic acid can comprise one or more barcodes, e.g., one or more barcodes that are the same (the same random single-stranded barcode, or the same pre-defined single-stranded barcode, or the same endogenous barcode) or a combination of two or more barcodes that are the same.

G to T Mutations

Sometimes, background error may comprise artifact guanine (G) to thymine (T) mutations. In some embodiments, reducing background can comprise eliminating artifact G to T mutations. The G to T mutations that are artifacts may occur on one of the two strands of a double-stranded nucleic acid. However, the G to T mutations that are not artifacts, e.g., real mutations, will likely occur on both strands of a double stranded nucleic acid molecule. Thus, removing G to T mutations due to artifacts can comprise identifying the parental nucleic acid strand from which the amplicons are derived. Barcodes can be used to identify the parental strand from which amplicons are derived. One or more double-stranded stem barcodes can be attached to a double-stranded nucleic acid. Different single-stranded barcode can be attached to the two strands the double-stranded nucleic acid. In some cases, amplicons derived from one strand of the nucleic acid and amplicons derived from the other strand of the nucleic acid can comprise the same double-stranded stem barcode, and one or more sequences on the nucleic acid (e.g., an endogenous barcode). In some other cases, amplicons derived from one strand of the nucleic acid and amplicons derived from the other strand of the nucleic acid can comprise different random single-stranded barcodes. Thus, in some embodiments, reducing background may comprise eliminating G to T mutations that occur on first amplicons derived from a first strand of a double-stranded nucleic acid, wherein the G to T mutations do not occur on second amplicons derived from a second strand of the double-stranded nucleic acid. In certain embodiments, the first amplicons and the second amplicons can comprise the same endogenous barcode and the same double-stranded barcode, but different random barcodes derived from the random single-stranded barcodes of the double-stranded nucleic acid.

In some embodiments, reducing background may comprise eliminating G to T mutations that occur on a fraction of first amplicons derived from a first strand of a double-stranded nucleic acid, but do not occur on a larger fraction of second amplicons derived from a second strand of the double-stranded nucleic acid.

The number of the first amplicons and the number of the second amplicons derived from the double-stranded nucleic acid can be determined using barcodes. In some embodiments, the first amplicons can comprise a first barcode derived from a first single-strand barcode on a first strand of the parental double-stranded nucleic acid. The second amplicons can comprise a second barcode derived from a second single-strand barcode on a second strand of the parental double-stranded nucleic acid. In some embodiments, the first barcode and the second barcode can comprise different sequences. In other embodiments, the first barcode and the second barcode can comprise the same sequence. The number of the first and the second amplicons can be determined by counting the first and the second barcodes.

The method disclosed herein can further comprise counting the numbers of the amplicons. In some embodiments, for example, the number of the first amplicons can be determined by counting amplicons comprising the same double-stranded stem barcode and the same endogenous barcode as the parental double-stranded nucleic acid, and a first random barcode derived the random single-stranded barcode on a first strand of the parental nucleic acid. Similarly, the number of the second amplicons can be determined by counting amplicons comprising the same double-stranded stem barcode and the same endogenous barcode as the parental double-stranded nucleic acid, and a second random barcode derived the random single-stranded barcode on a second strand of the parental nucleic acid. Accordingly, the number of the first amplicons carrying a G to T mutation at a locus and the number of the second amplicons carrying the G to T mutations at the same locus can be determined using the barcodes.

Reducing background can also comprise eliminating mutations that do not occur on both strands of a double-stranded nucleic acid. In some embodiments, reducing background error can comprise eliminating mutations that occur on less than about 50% (or a higher threshold) of amplicons comprising the same double-stranded stem barcode and the same endogenous barcode.

Estimating LLOD

In some embodiments, the invention includes a step of estimating sensitivity of ctDNA detection as illustrated on FIG. 7 (b). In some embodiments, the sensitivity depends on the number of reporters. The sensitivity is estimated in an assay-independent manner by utilizing knowledge of available number of tumor genome equivalents and tumor-specific reporters (i.e., somatic variants). The method utilizes a combination of several tumor-specific reporters (as described in PCT/US14/25020 (US20140296081)) that enable to scale detection limits as compared to a single reporter (e.g., dPCR). For example, the use of 8 reporters yields an eight-fold reduction in the lowest limit of detection (LLOD) compared to a single-reporter detection. In some embodiments, the reporters behave independently. In some embodiments, the LLOD of the detection method is below the number of available tumor genome equivalents.

FIG. 15 illustrates a statistical framework for ctDNA detection and selector design. FIG. 15 (a): within the typical cfDNA yield from 10 mL blood (assuming ~50% capture efficiency), a simple analytical model allows estimation of ctDNA detection limits as a function of available tumor reporter. In FIG. 15 (b), detection limit of ctDNA shown as a function of available tumor reporters and sequenced GEs for >90% detection likelihood. In FIG. 15 (c), distances between adjacent somatic mutations found in the coding regions of lung adenocarcinoma (LUAD) tumors profiled by The Cancer Genome Atlas (TCGA) (n=381). The vertical dashed line indicates the median length of cfDNA molecules. FIG. 15 (d) shows concordance between the number of distinct tumor reporters observed versus those predicted by analytical modeling utilizing pretreatment NSCLC plasma and defined spike-ins from previous work. FIG. 15 (e) Analysis of the number of SNVs and indels per tumor covered by the NSCLC selector in both a TCGA training cohort (LUAD) and an independent lung adenocarcinoma cohort. FIG. 15 (f) Reproducibility of each selector tile in capturing NSCLC patients between a TCGA training dataset and a validation cohort profiled by CAPP-Seq. Recurrence index is equal to the percentage of unique patients covered per kilobase.

In some embodiments, the invention is a method of genotyping circulating tumor nucleic acids (e.g., ctDNA) with an improved lowest level of detection (LLOD). In some embodiments, the invention is a method of assessing cancer in a patient by genotyping ctDNA from the patient using a selector design targeting a LLOD of 0.01% or less, up to 0.0001% (i.e., a selector design with a sufficient number of reporters to achieve LLOD 0.01% or less, up to 0.0001%). In some embodiments, the invention further comprises genotyping a matching tumor sample from the patient obtained by any method known in the art, e.g., surgical samples or fine needle biopsies; frozen samples and formalin-fixed specimens. In some embodiments, the invention further comprises genotyping a non-tumor sample from the patient, e.g., peripheral blood leukocytes to confirm tumor association of the clinically defined variants.

Figure 8D:
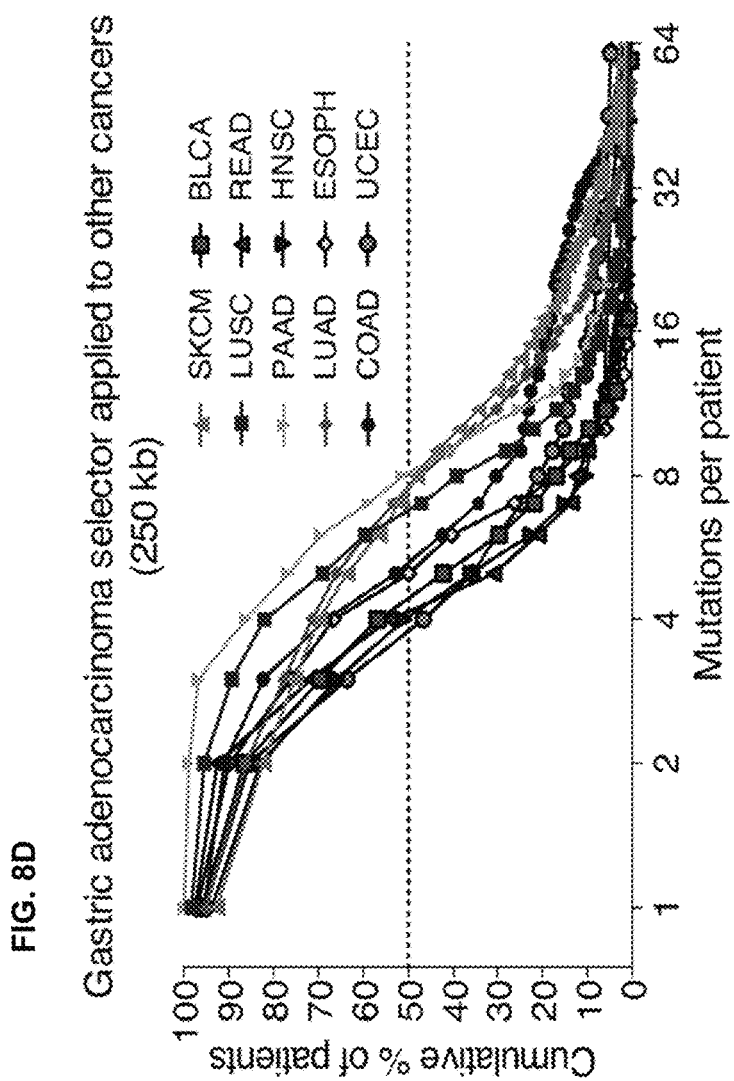
Figure 8E:
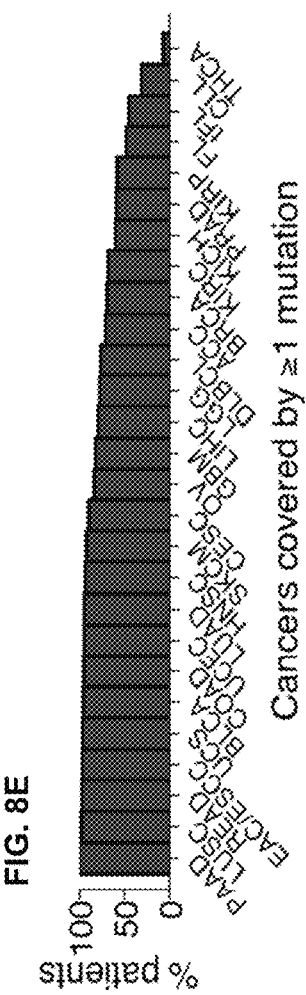
Figure 9A:
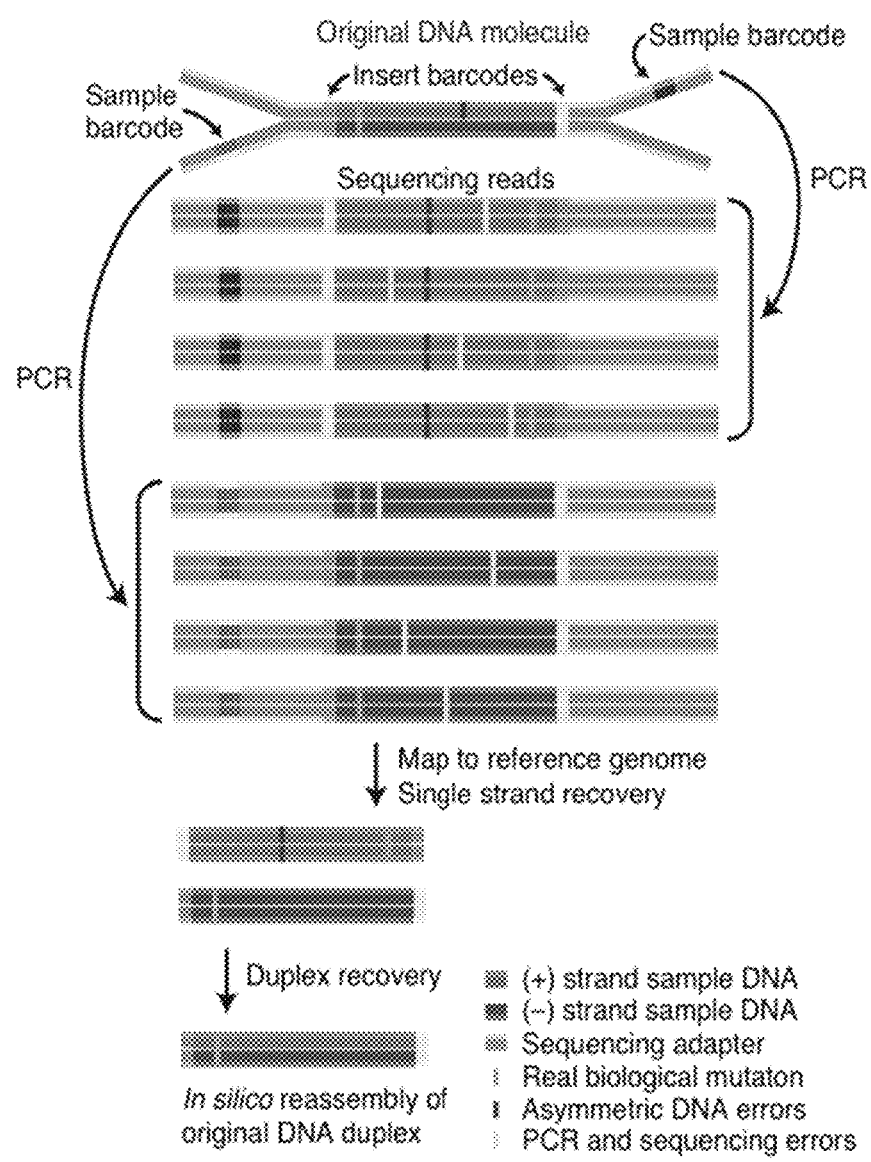
FIG. 9A-9F: Development of integrated digital error suppression.
Figure 9B:
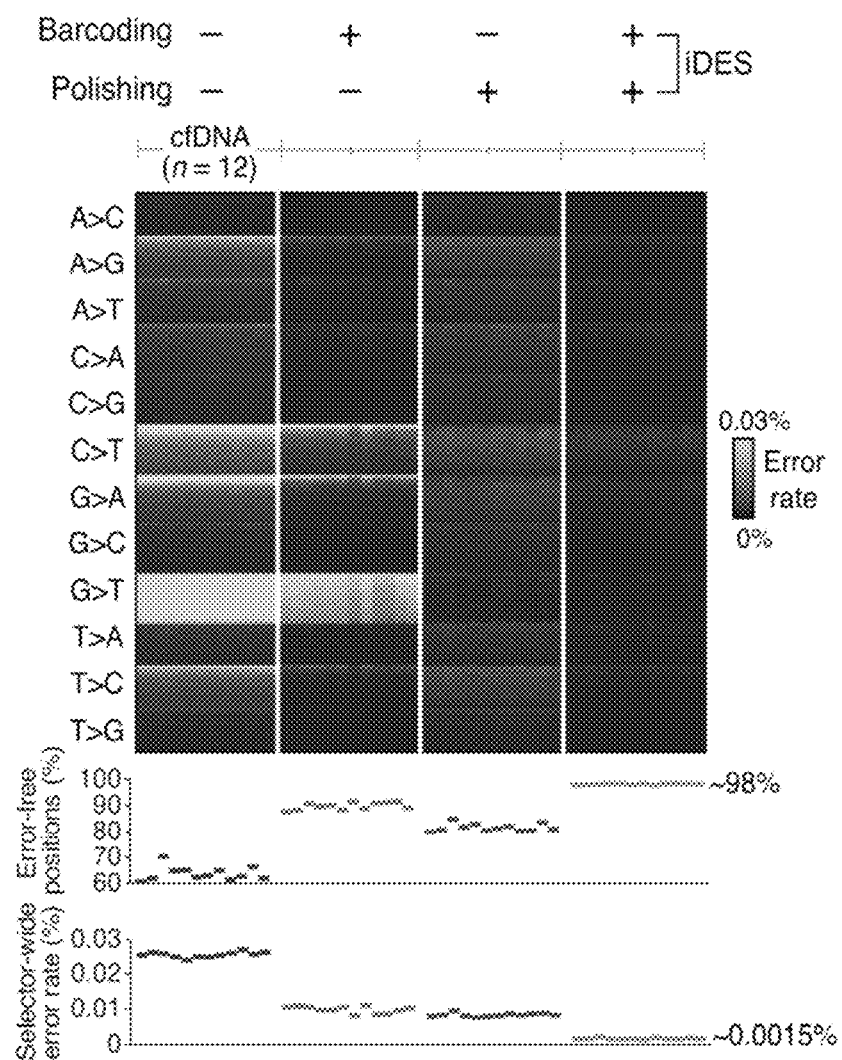
Figure 9C:
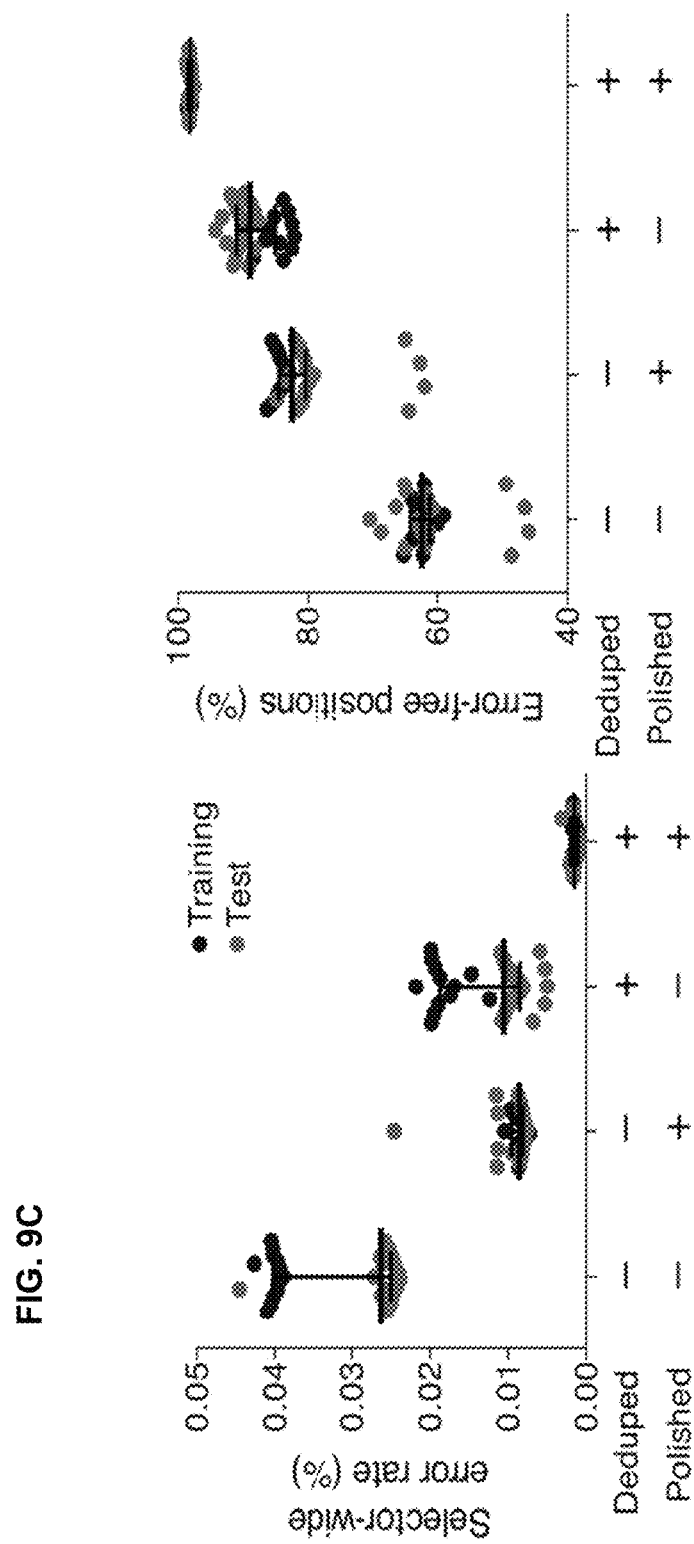
Figure 9E:
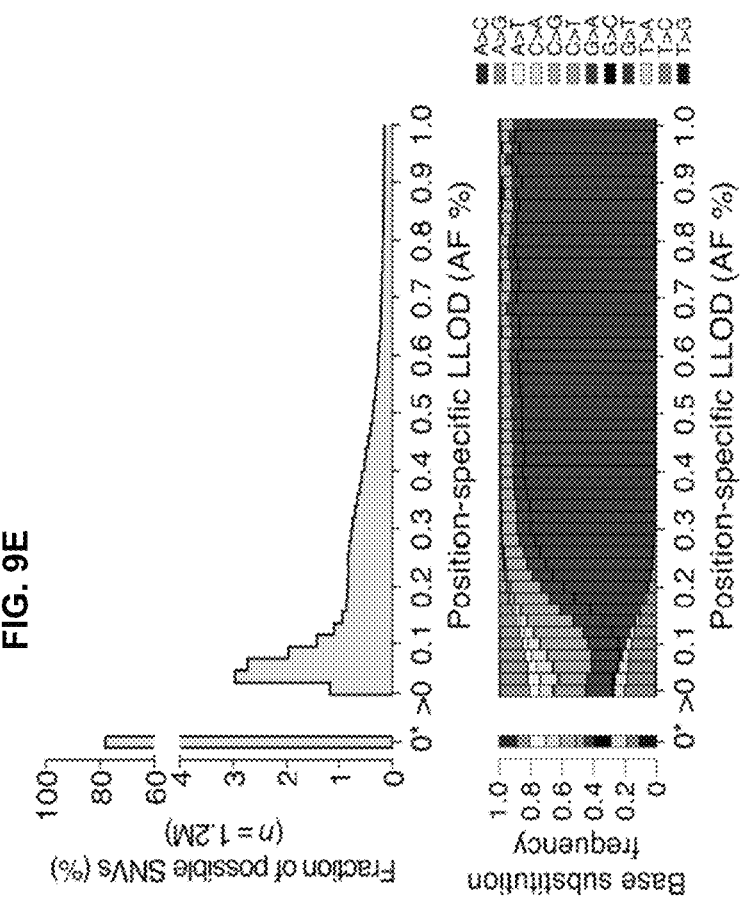
Figure 9D:
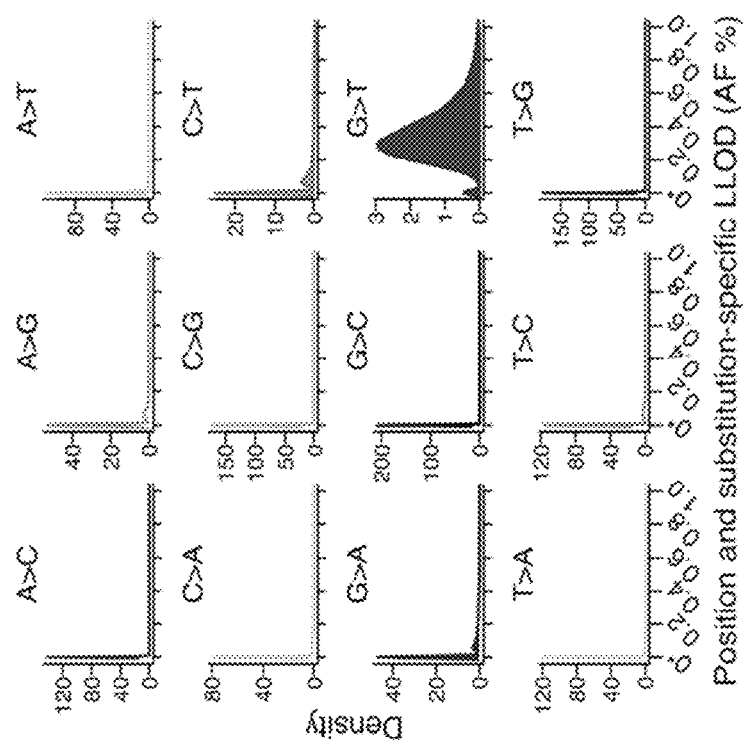
Figure 9F:
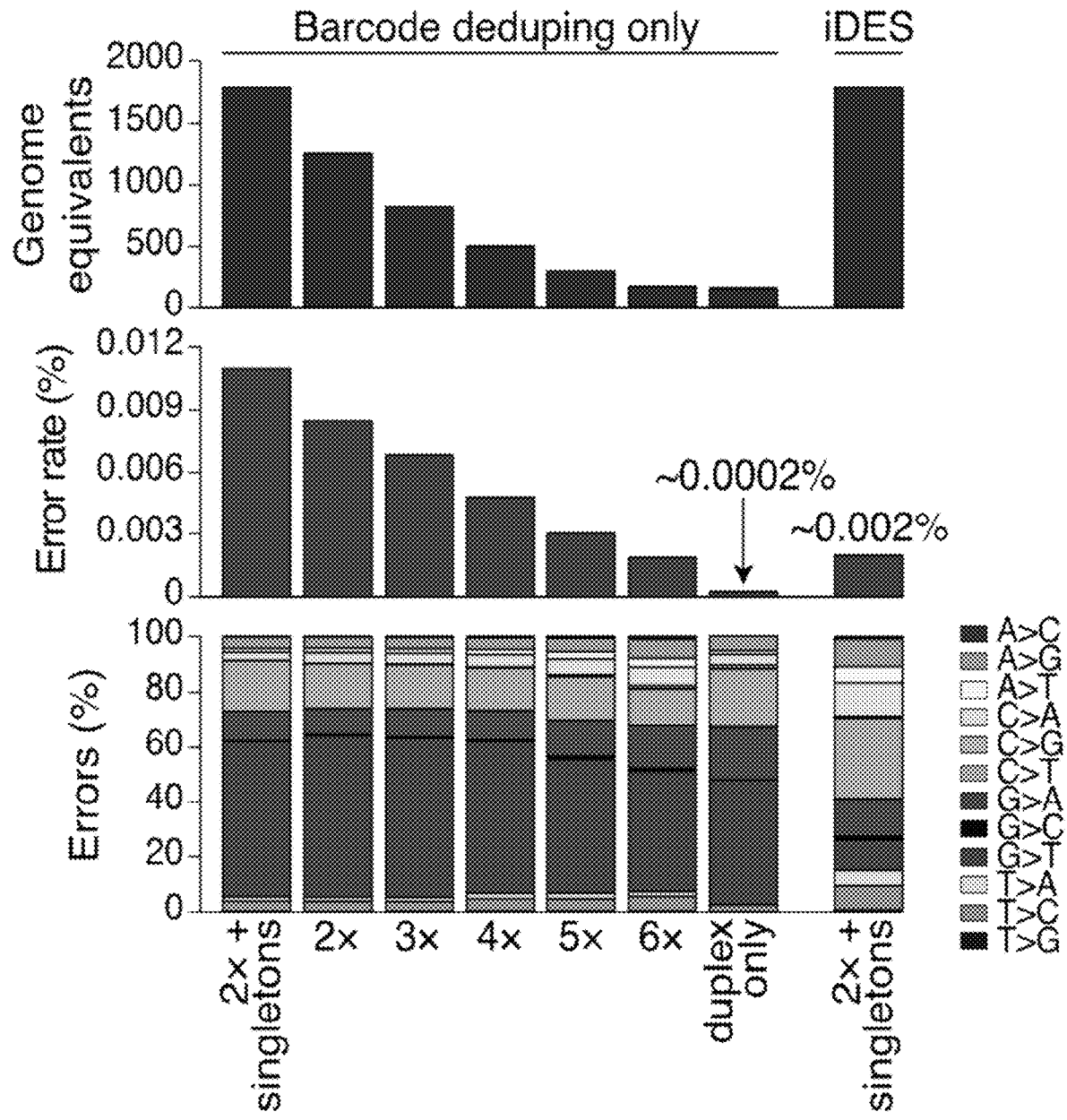

The inventors have discovered that a number of cancers are covered by at least one common mutation. In some embodiments, a selector is designed using one type of tumor according to the method of the invention and used in a different type of tumor as illustrated on FIG. 8.

Removing Duplicates "Deduping"

In some embodiments, the invention is a method of sequencing ctDNA that comprises a step of reducing background errors by grouping the molecules sharing the same unique molecular ID (UID) into families. This step determines the number of original molecules sequenced (as the number of families sharing a UID) and eliminates errors not shared by all the members of the family. These errors can be introduced by oxidative nucleoside damage, PCR, and other exogenous sources during ex vivo copying or processing of the target molecule. The method of grouping molecules by UID and assessing errors is herein referred to as "deduping."

Error Suppression Using Different Barcodes

In some embodiments, the invention is a method of assessing cancer by analyzing ctDNA with error suppression using molecular barcoding. In variations of this method, the invention is a method of error suppression in genotyping ctDNA from a patient using molecular barcoding. In this embodiment, ctDNA from a subject, e.g., a patient is obtained and prepared for sequencing according to methods described herein. For example, as little as 30 ng of ctDNA can be extracted from a subject and sequenced to the depth of 1000-10,000×, e.g., 6,000×. The sequences can then be "deduped" using UIDs as described herein. To benchmark error-suppression from molecular barcoding, the inventors profiled cfDNA samples from 12 healthy adults. For each subject, uniform DNA inputs (median 32 ng) were sequenced to a median depth of nearly 6,000× (pre-duplication removal). Given the typically low cfDNA yields in clinical plasma samples, error rates and barcoding performance can be assessed using all recovered molecules (i.e., regardless of UID copy number or strandedness). In some embodiments, based on the assessment of the methods of error correction, the method of the invention includes comparing non-deduped data to assess whether internal (insert) or external (adaptor) molecular barcodes reduced selector-wide background by a greater number. In some embodiments, the method includes using internal (insert) UIDs for error-suppression or barcode-deduping strategy.

Stereotyping Errors

In some embodiments, the invention is a method of reducing background in sequencing of nucleic acids including ctDNA, by identifying as errors and removing nucleotide changes from genome locations determined to be error-prone in a prior sequencing study such as a population study. In some embodiments, the error-prone location is a G (guanine) and the removed nucleotide change is a T (thymine). The inventors have observed that in healthy blood donors, error-prone positions were strikingly stereotyped in their genomic locations and base-substitution spectrum (FIG. 9 (b) and FIG. 10). Even after error suppression using barcode-deduping, most remaining errors consisted of these stereotyped low frequency alleles (<0.1%), with the majority due to G>T transversions and, to a lesser extent, C>T or G>A transitions (FIG. 9 (b)). Without becoming bound by a particular theory, the inventors hypothesized that oxidative damage of nucleic acids during library preparation may be occurring leading to formation of 8-oxoguanine and cytosine deamination. The inventors further observed that when mapped to the opposite (plus) strand of the reference human genome, G>T changes were highly skewed compared to reciprocal C>A events (FIG. 9 (b)), and this imbalance was not attributable to sequencing strand bias (FIG. 11 (b)). The inventors therefore examined the enrichment step, and identified a graded increase in the ratio of G>T errors to C>A errors reproducibly increasing by 2.5-fold between 0.1 days-long and 3 days-long duration of targeted sequence capture (FIG. 11 (c)). A similar trend was observed for errors exclusively seen in both DNA strands (duplex-only data, FIG. 11 (d)). The data shows that the G>T transversions are largely driven by reactive oxygen species coupled with a capture reagent that exclusively targets the positive strand (FIG. 11 (e)). In some embodiments, the invention includes a step of reducing background error in nucleic acid sequencing by removing damaged nucleic acids from the nucleic acids in a sample by contacting the sample with one or more nucleic acid repair enzymes. Examples of such repair enzymes include (i) uracil DNA-glycosylase (UDG), which leaves an abasic site in place of uracil (a cytosine oxidation product), preventing PCR from continuing through the site of oxidation, eliminating C>T errors due to cytosine oxidation; (ii) 8-oxoguanine DNA glycosylate (FPG), which removes damaged purines and cleaves at the site of the damaged bases, eliminating G>T errors due to guanine oxidation. Reducing error rates by application of these enzymes is illustrated on FIG. 11 (a).

Threshold for Variant Calling in Error Suppression

Single-molecule sequencing error rates are heterogeneous, differing in magnitude across target genomic intervals and between types of base substitution. Moreover, sequencing depths typically vary within and across samples. Collectively, these issues complicate the selection of robust thresholds for variant calling, leading to suboptimal tradeoffs between sensitivity and specificity. To improve the detection rate of low frequency alleles, we developed a general genotyping approach that adaptively considers local and global variation in background error rates, enabling automatic determination of position-specific variant calling thresholds in each sample. The method comprises determining threshold t for minimum number of sequencing reads with a variant (SNV) to identify the variant as a true variant and not an artifact.

In one embodiment, the invention comprises a step of determining a global rate of errors for each class of base substitutions using a control sample. In some embodiments, global error rate was determined for 24 possible base substitutions. In some embodiments, the threshold setting step excludes candidate sequence variants with >5 supporting reads to minimize the confounding influence of true variants. Given that base substitution classes have disparate background distributions (FIG. 2b), we sought to control the false positive rate for each class separately. Toward that end, we modeled the cumulative distribution of background errors for each base substitution class. The inventors have discovered that power series and exponential functions fit the observed data well (FIG. 19 (a)), and for each class, we selected the function that best captured the data using linear regression in log-linear space. To increase sensitivity, we modeled candidate sequence variants with and without second nucleic acid strand support separately, for a total of 24 base substitution models per sample (2 strands×12 substitution classes). Such models readily illustrate the impact of background polishing on substitution-specific error rates (FIG. 19 (a)). The method further comprises a step of defining a function relating the number of errors to the number of observed supporting reads. In some embodiments, the number of errors is adjusted for experimental parameters, e.g., per number of bases sequenced "cumulative errors." The method is further comprising a step of solving each of the 24 functions to identify the minimum number of supporting reads t needed to yield y cumulative errors. In some embodiments, y=0. (FIG. 19 (a)). In some embodiments, the invention further comprises adjusting threshold t as set forth below.

In one embodiment, the invention comprises a step of adjusting the global error rate based on local error rates and sequencing depth. The step comprises determining error rate e (defined as the number of positions harboring non-reference bases divided by the number of sequenced bases) and determining sequencing depth d for each gene. (FIG. 19 (b).) If gene g falls within the top 25 percent of selector-wide gene-level error rates, the threshold t is adjusted to t' according to:

$t' \leftarrow t \times w$, where $w = \min\{q^2, 5\}$ and $q = e$ divided by the $75^{th}$ percentile of the error rates of all evaluable genes If gene g has sequencing depth d below the median selector-wide sequencing depth $d^{med}$, the threshold t is adjusted to t' according to:

$t' \leftarrow t / w^*$, where $w^* = \ln(d^{med}/d)$

In some embodiments, the invention is a method of sequencing nucleic acids including cfDNA with a reduced rate of errors, comprising identifying as true SNV sequence variants, the variants that exceeded the experimentally established threshold (i.e., the number of reads with the variant exceeded the threshold), wherein the threshold is determined as set forth above.

Removing Low-Frequency Alleles

In some embodiments, the invention comprises a step of applying a heuristic filter to detect and remove SNVs with lower allele frequencies. (FIG. 19b) The step comprises creating a list of candidate SNVs, ranking SNVs according to allele frequency and removing the lowest-frequency SNVs. In some embodiments, the method comprising statistical analysis to determine the threshold point for separating errors from true SNVs. The method may comprise dividing the list in at least two sections statistically evaluating the difference in variance between the two sections, yielding a p-value and a p-value minimum. Upon ranking L by increasing AFs, an iterator i was used to traverse the list. For each i, L was split into two parts, SNVs with an AF below $L_i$ and SNVs with an AF≥$L_i$. A two-sided F-test was employed to statistically evaluate the difference in variance between the two lists, yielding a p-value. The SNVs below the minimum list L was then traversed in order of increasing AFs to identify the index i* of the first p-value corresponding to a local minimum, if one exists. Such a minimum, if detected, indicates a potential inflection point between noise (lower tail) and signal (higher AFs). If the p-value corresponding to i* was below 0.05 and if $L_i$ was at least 10% greater than $L_{i-1}$, we subsequently evaluated the difference between $L_i$ and the distribution of potential background events, $L_1$ to $L_{i-1}$, using a one-sided z test (justified given normality observed for SNV AFs). If the corresponding p-value was <0.01, the candidate SNV list was split and the lower tail ($L_1$ to $L_{i-1}$) was removed. In empirical analyses, this procedure was found to improve specificity (data not shown) suggesting it can effectively detect residual background variants.

Integrated Digital Error Suppression (iDES)

In some embodiments, the invention is a computational approach to suppress position-specific sequencing errors. In this embodiment, the method comprises obtaining a baseline distribution of sequence variations to set an experimentally determined threshold for single nucleotide variations (SNVs), followed by "in silico polishing" (eliminating variants with allele fractions falling below the threshold) from barcode-deduped data. In this embodiment, the invention comprises a method of reducing errors in sequencing of nucleic acids including ctDNA comprising grouping the molecules sharing the same unique molecular ID (UID) into families and eliminating as errors nucleotide changes having a frequency below a predetermined threshold. A threshold can be established in a sequencing study such as a population study. The method is illustrated on FIG. 9. FIG. 9 (a) is a schematic depicting tandem sequencing adaptors ligated to a hypothetical double stranded (duplex) DNA molecule containing a real biological mutation in both strands as well as a non-replicated, asymmetric base change in only one strand (top). The application of internal/insert barcodes allows (i) error suppression and (ii) recovery of single stranded (center) and double stranded (bottom) DNA molecules. FIG. 9 (b) (top) shows a heat map depicting position-specific selector-wide error rates parceled into all possible base substitutions (rows) and organized by decreasing mean allele fractions (for each substitution type) across 12 cfDNA samples from healthy controls (columns). Background patterns are shown for non-deduped data (left), barcode-deduped data (center), and barcode-deduped data after background polishing (right). Errors are defined as non-reference alleles excluding germline SNPs. Dark indicates no background and light indicates a ceiling of 0.03% fractional abundance. FIG. 9 (b) Bottom: Selector-wide error metrics. FIG. 9 (c) shows effect of barcode deduping and background polishing on selector-wide error metrics for 30 normal control cfDNA samples, divided into training (n=12) and test (n=18) cohorts. Medians and interquartile ranges are shown. (d) Density plots of the selector-wide LLOD for each base substitution. FIG. 9 (e) (top) shows a histogram of selector-wide detection limits for all possible base substitutions. FIG. 9 (e) (bottom) shows distribution of base substitution types for each bin in the histogram above. Pie chart shows distribution of single base changes for the top 1% of variants by frequency from the Catalogue of Somatic Mutations in Cancer (COSMIC) database intersected with our NSCLC selector FIG. 9 (f) shows comparison of iDES against different barcoding deduping strategies across 30 cfDNA control samples. All analyses in FIG. 9 b-f were performed with the NSCLC clinical selector.

Figure 10:
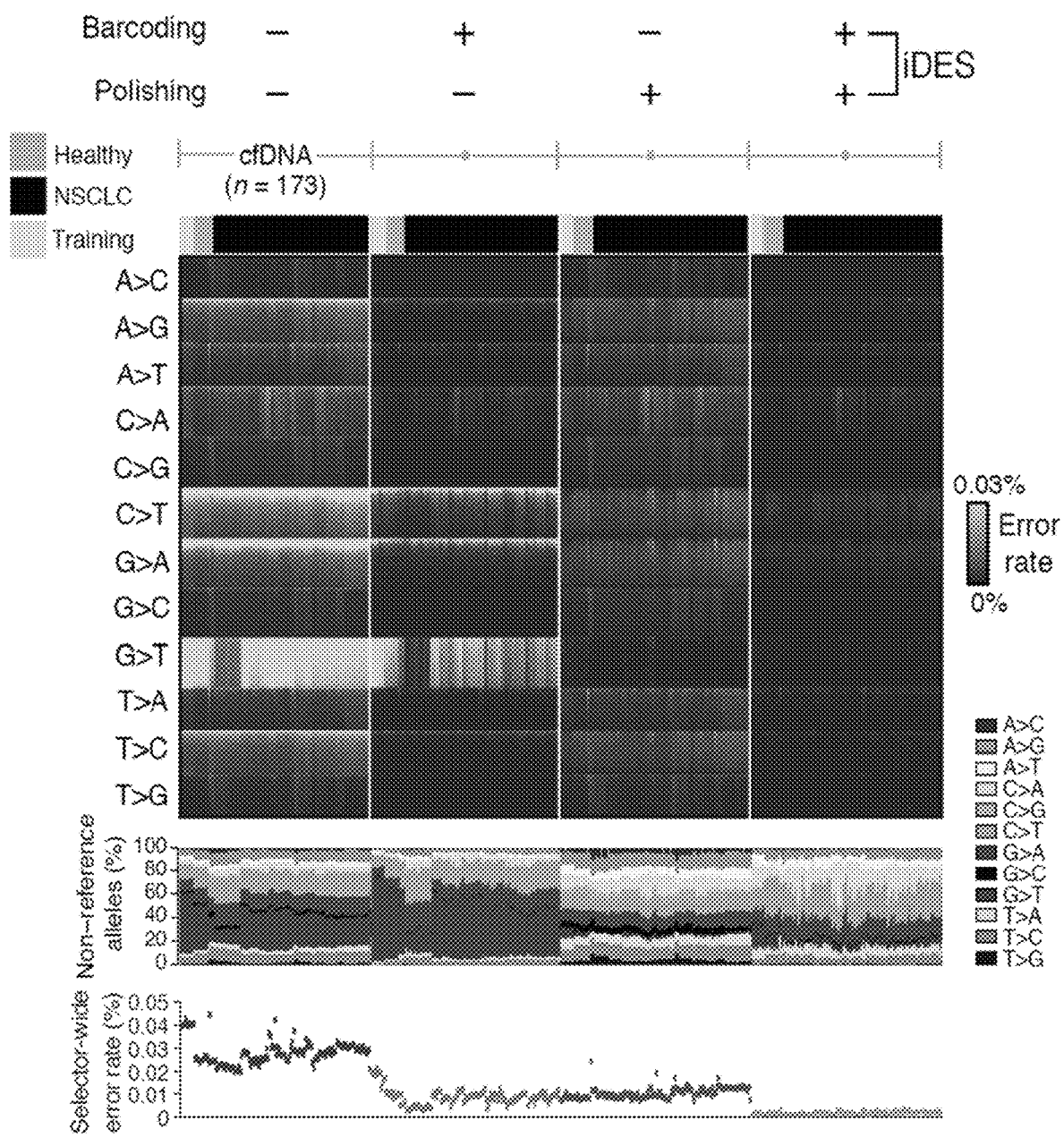
FIG. 10: Stereotyping base substitution errors
Figure 11A:
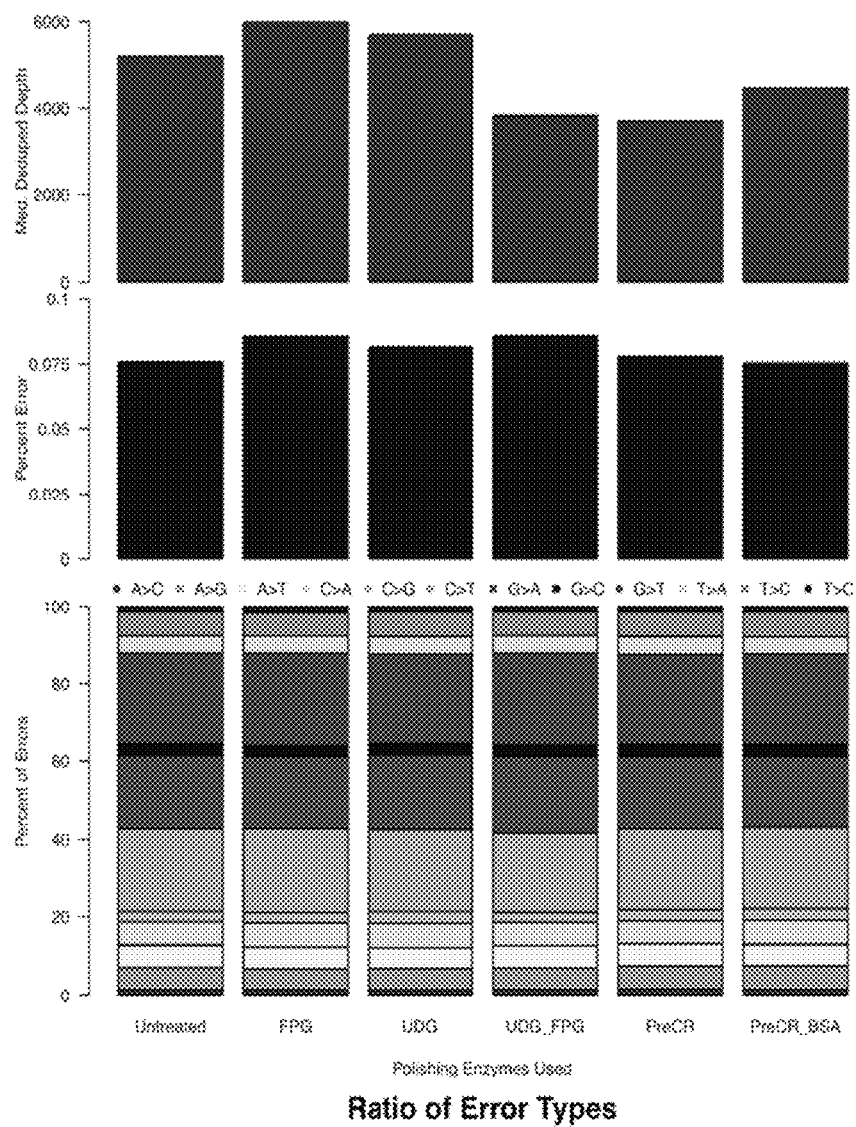
Figure 11B:
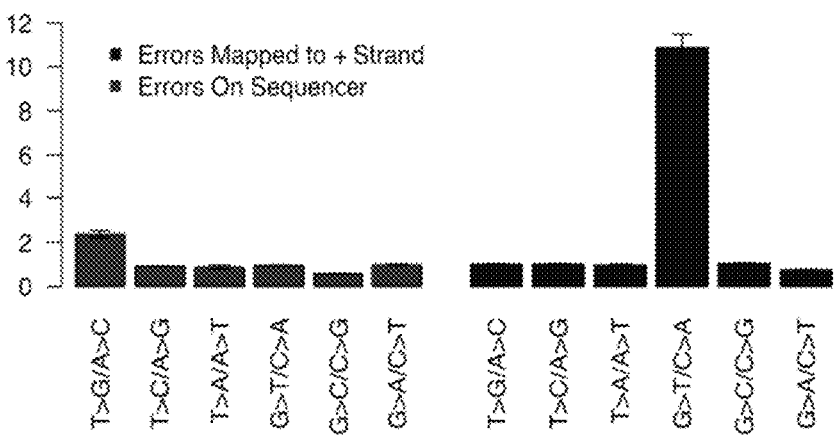
Figure 11C:
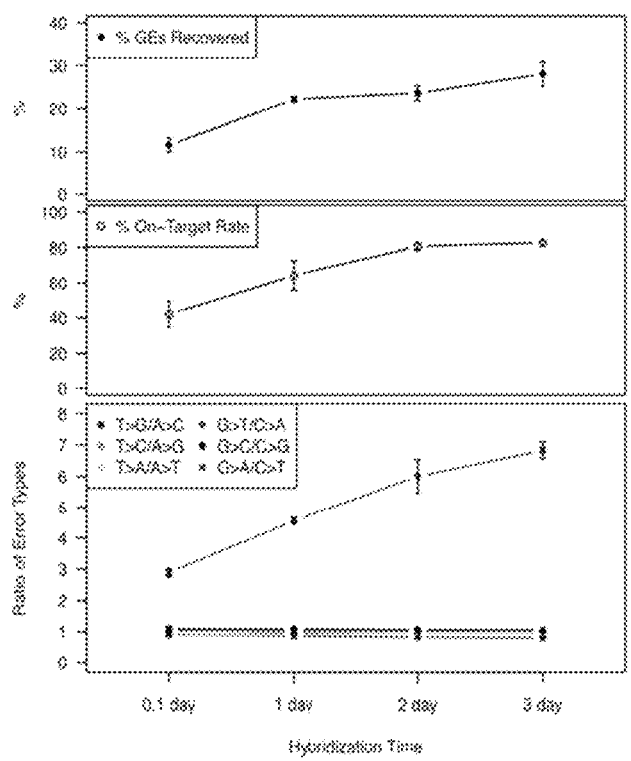
Figure 11C:
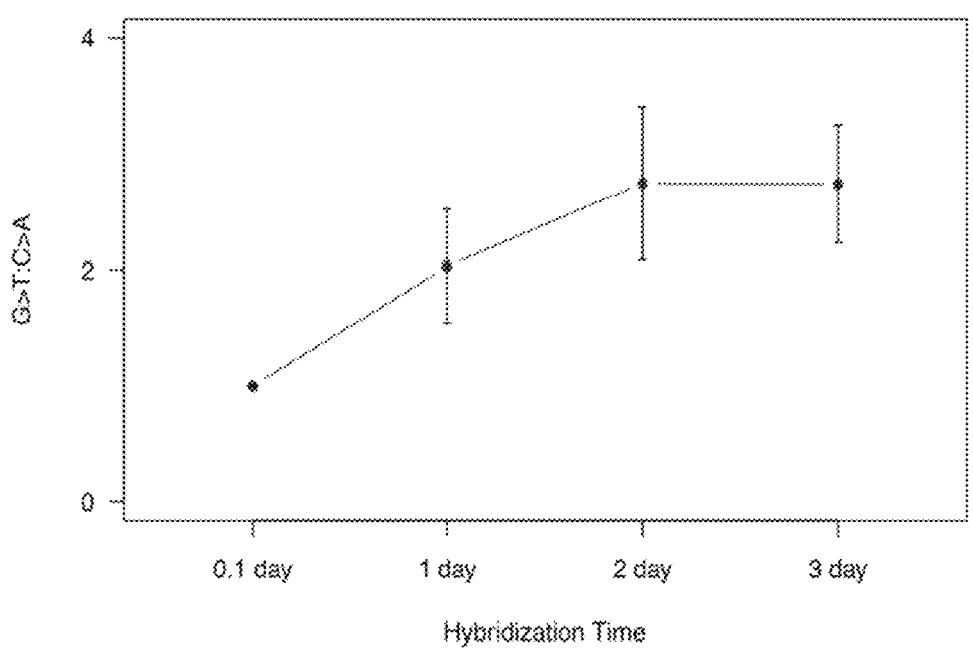
Figure 11E:
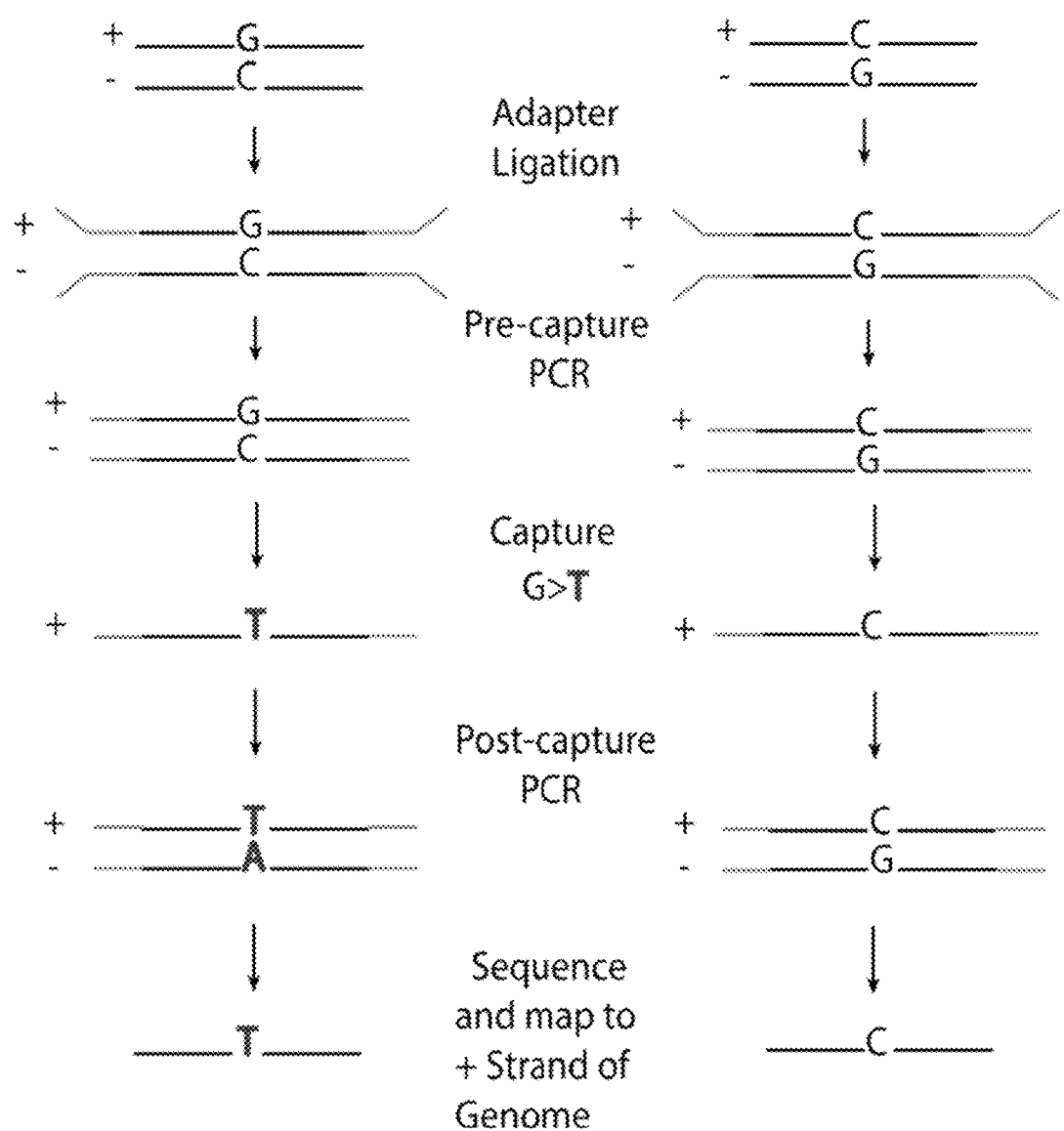
Figure 12A:
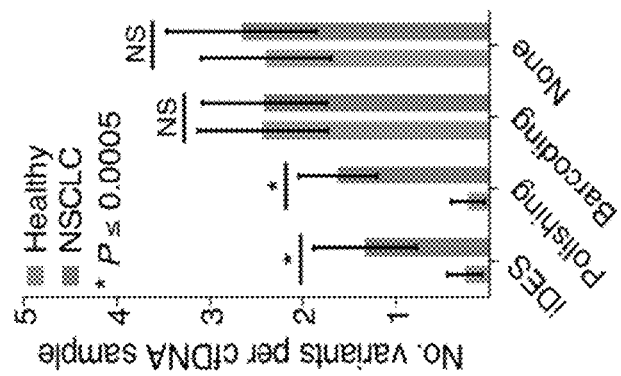
FIG. 12A-12I: Biopsy-free tumor genotyping and ultrasensitive monitoring of NSCLC with iDES.
Figure 12A:
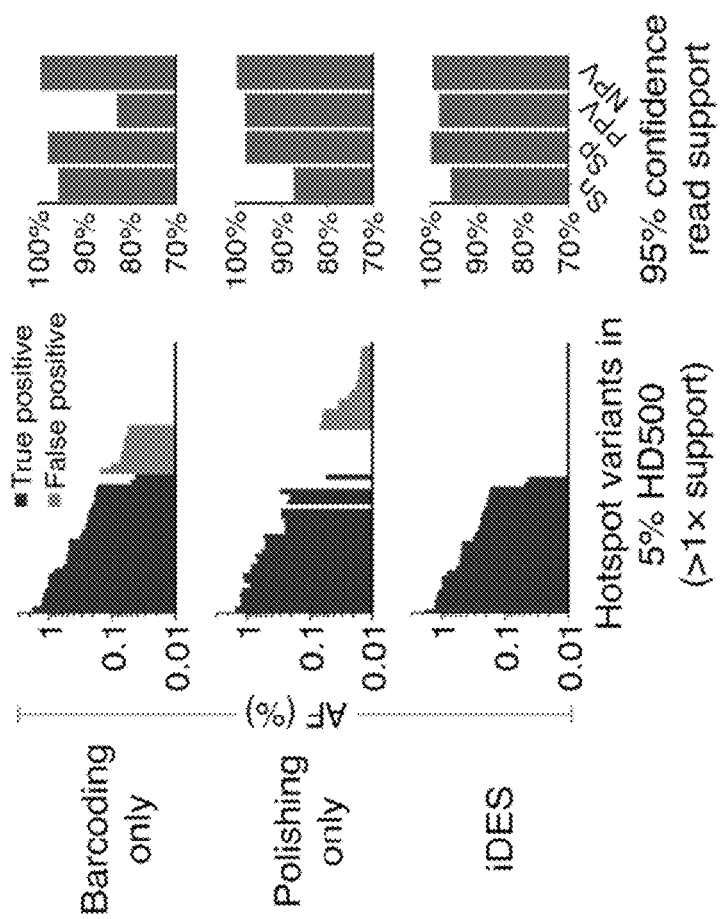
Figure 12C:
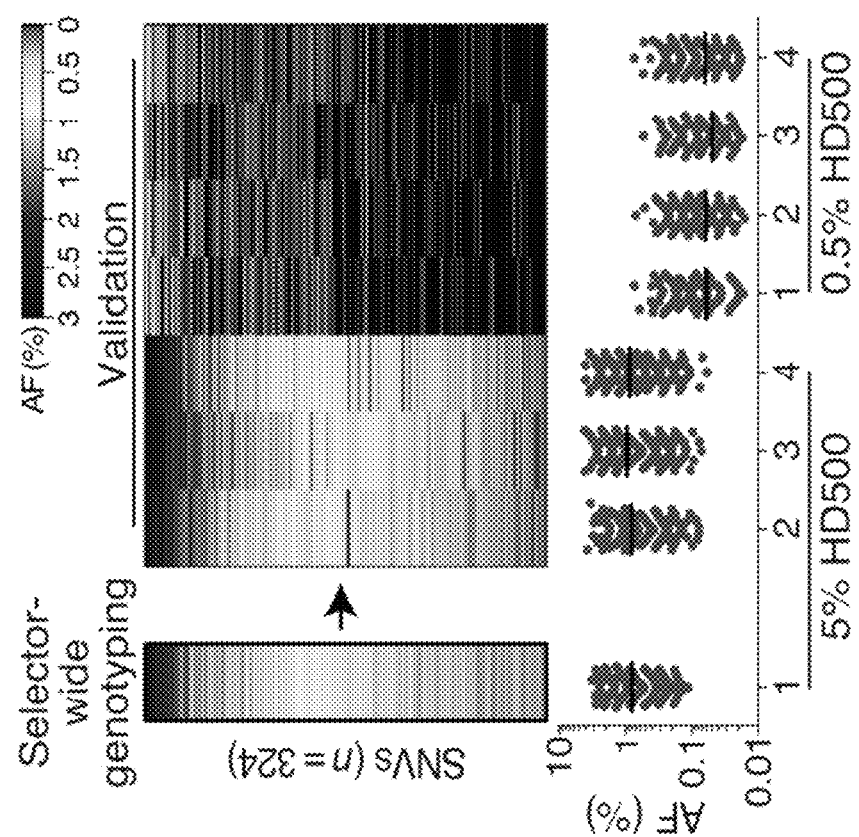
Figure 12B:
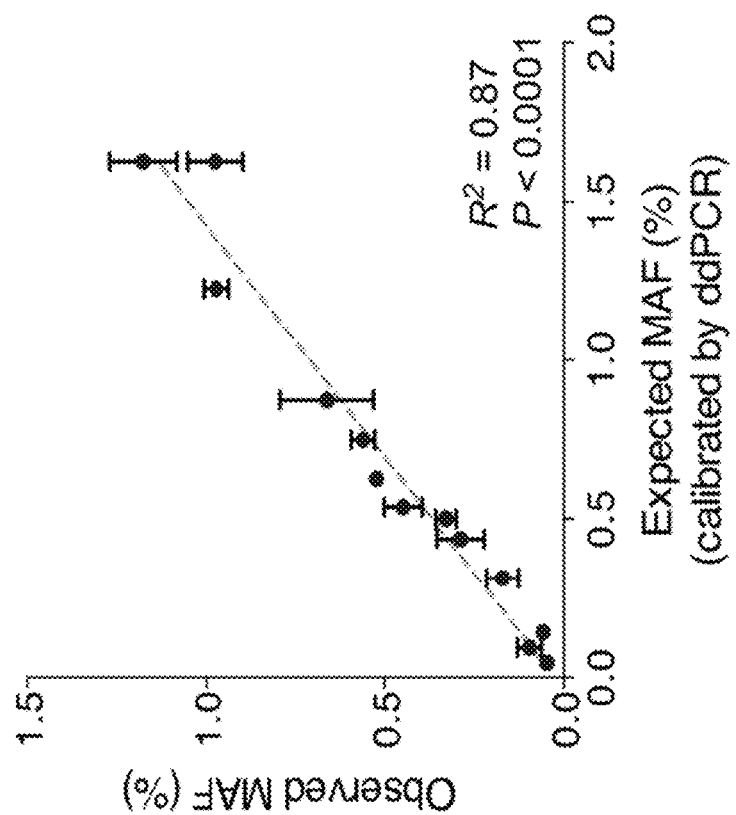
Figure 12D:
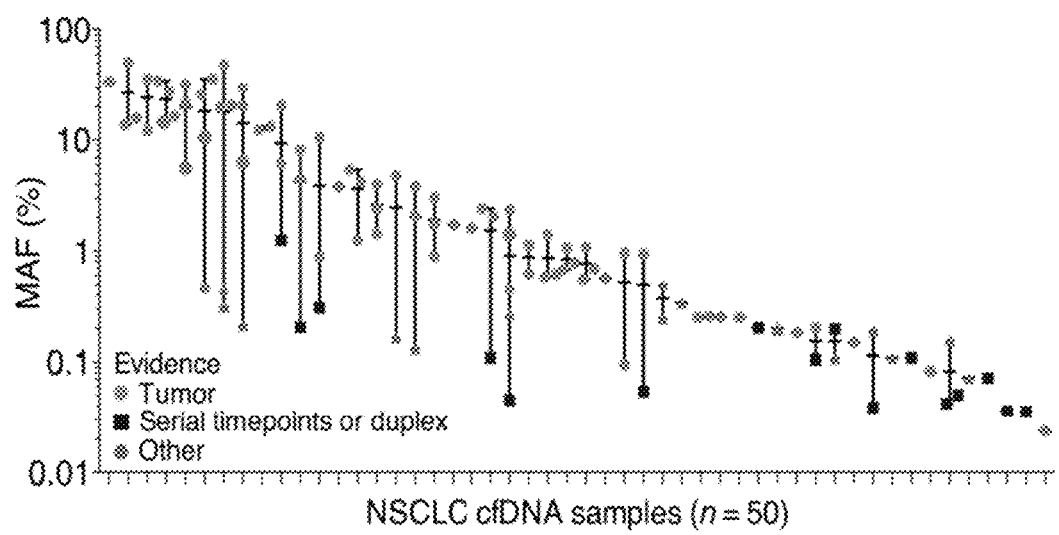
Figure 12E:
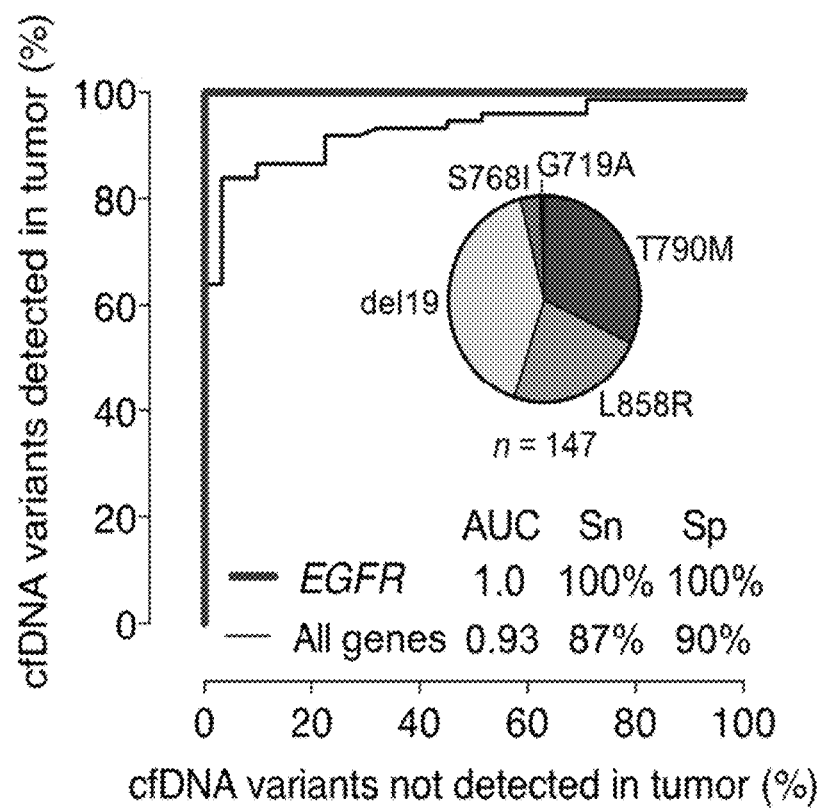
Figure 12F:
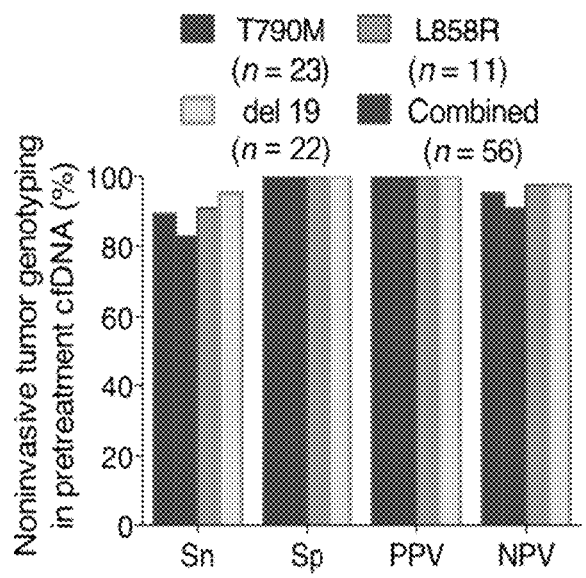
Figure 12G:
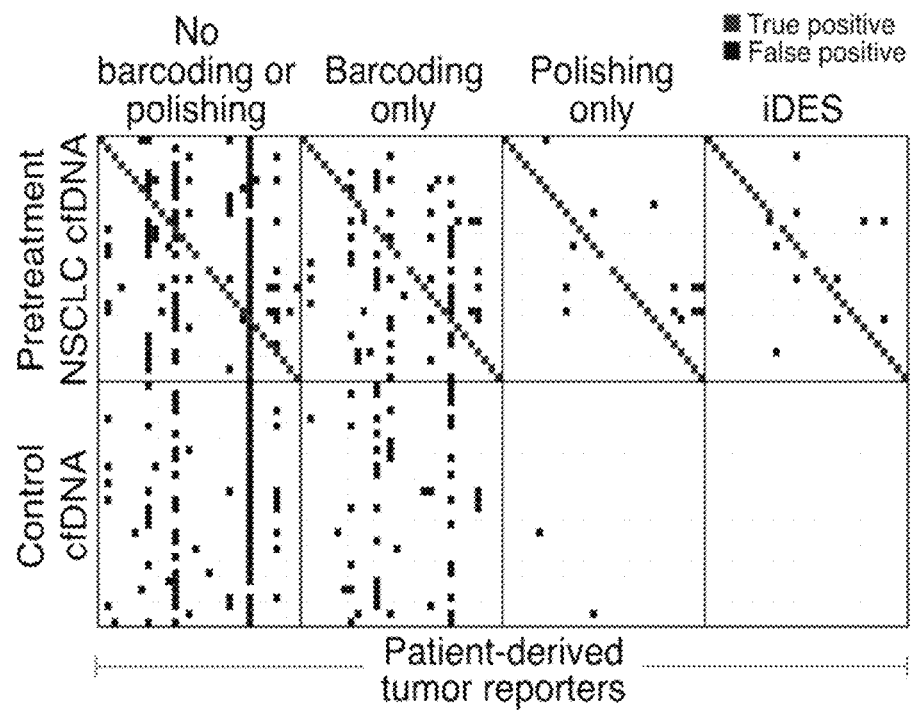
Figures 12H, 12I:
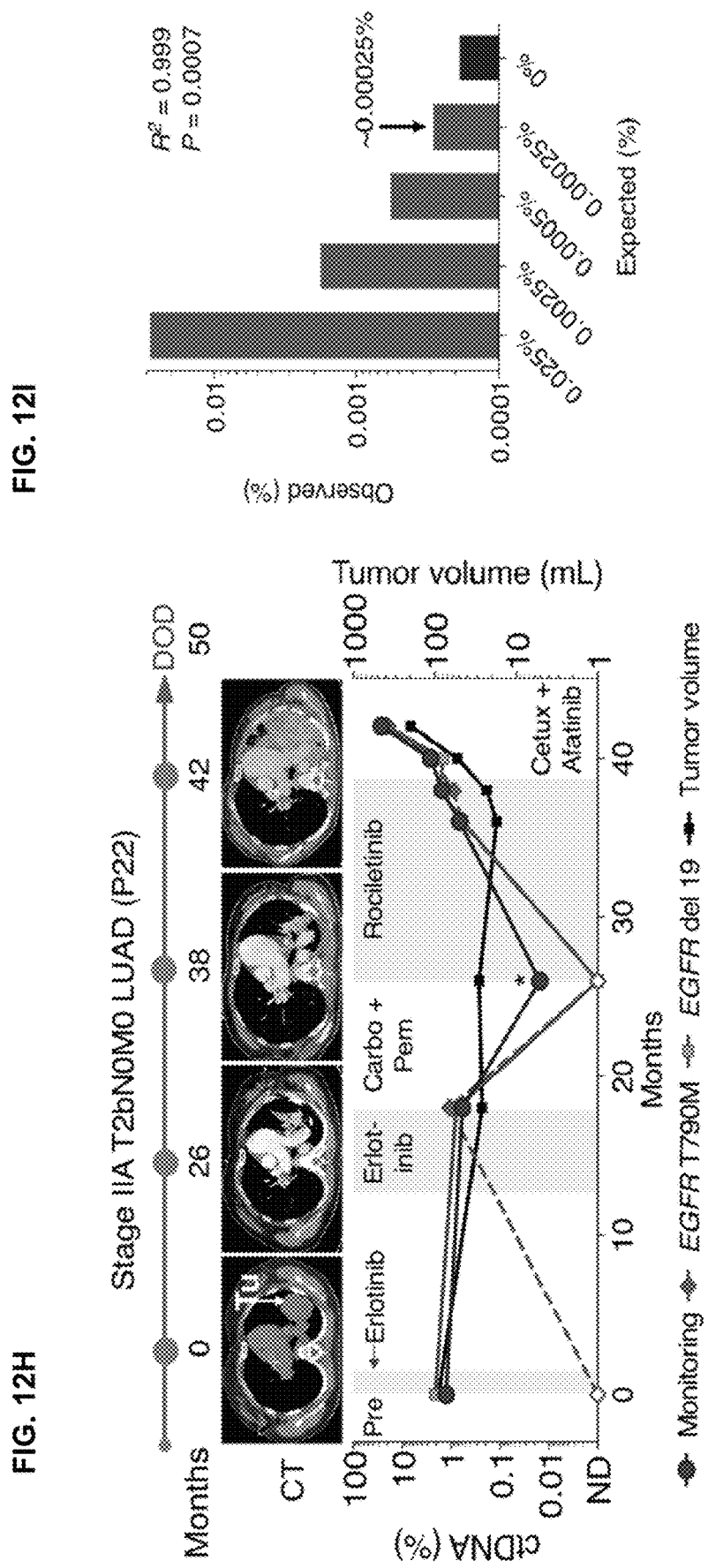

The invention comprises assessing cancer by genotyping ctDNA with a low error rate obtained by error suppression comprising "in silico polishing" of barcode-deduped data, eliminating variants with allele fractions below position-specific thresholds (FIG. 9 (b)). The inventors termed this combined application of in silico polishing and molecular barcoding "integrated digital error suppression" (iDES) to reduce or eliminate the effect of stereotyped and stochastic errors, respectively. In some embodiments, selector-wide error rates dropped to $1.5 \times 10^{-5}$, and error-free positions increased to ~98%. In variations of this embodiment, the method comprises only background polishing of deduped or non-deduped cfDNA samples (i.e., polished with or without the use of barcodes), or only barcode deduping without polishing. However, it is noted that when performed together, the two approaches synergize. (FIG. 10).

In some embodiments, the invention is an analysis of error profiles to characterize allele-specific detection limits across large regions of the human genome that are recurrently mutated in cancer genomes. The invention comprises analyzing the 12 possible nucleotide-substitution classes, to determine their error rate, background and LLOD. The invention further comprises determination on whether the particular substitution class is represented in the Catalogue of Somatic Mutations in Cancer (COSMIC) (FIG. 9 (d)). As described herein, nearly 80% of all possible SNVs were detected error-free (FIG. 9 (e)). Among residual errors, G>T detection was most notable, yet maintained a reasonably low median LLOD of ~0.3% across the selector (FIG. 9 (d)). Moreover, G>T changes, which encompassed the majority of alleles with detection limits >0, comprised only 5% of mutational hotspots annotated by the COSMIC overlapping our NSCLC selector, suggesting minimal impact on genotyping performance (FIG. 9 (e)).

In some embodiments, the invention is a method of assessing the condition of a patient by sequencing the patient's cfDNA with a reduced error rate and maximized sensitivity, the method comprising the steps of utilizing duplex molecules when available, but otherwise utilizing single-stranded molecules to obtain background-polished sequencing data.

In some embodiments, the invention is a method of assessing the status of a patient via biopsy-free genotyping of a tumor using integrated digital error suppression (iDES). The method may comprise a step of first assessing performance of iDES on somatic alterations (SNVs and indels) that are highly recurrent and clinically relevant in cancer. The assessment may be performed by applying the genotyping to cfDNA from healthy subjects. The calls with duplex support suggest bona fide variant alleles arising in vivo while barcoded and non-deduped data indicates false positive calls. The invention may further comprise a benchmark evaluation of simulated ctDNA using defined inputs of a mutant DNA spiked into control cfDNA. If the mutations in the spiked DNA are known, the invention may comprise assessing sensitivity, specificity, positive predictive value, and negative predictive value and false positive rate for detecting rare variants.

In some embodiments, the invention is a method of integrated digital error suppression (iDES) for biopsy-free genotyping of patients from blood plasma. The method may comprise a confirmation of mutations as somatic in a matched tumor biopsy. For example, the invention is a method of assessing cancer in e.g., NSCLC patients, e.g., stage (IB-IV) that includes a non-invasive assessment of the tumor genotype with a low error rate. In some embodiments, genotyping includes detecting EGFR mutations, including mutations in the kinase domain (exon 19, exon 20 and 21) that include activating and resistance mutations.

In some embodiments, the invention is a method of error suppression (iDES) for biopsy-free genotyping of NSCLC patients from patient's blood plasma sample where the genotype of the patient's tumor is known. In some embodiments, the invention comprises investigating clonal dynamics within the patient's tumor by genotyping cfDNA. In another embodiment, the invention is a method of biopsy-free genotyping of detecting a likelihood of response or resistance to erlotinib or a mechanism of resistance to erlotinib. In another embodiment, the invention is a method of prognosis or detecting disease progression in a patient affected with cancer by genotyping cfDNA from a plasma sample according to the low-error methods described herein. In some embodiments, the invention is a mechanism of detecting resistance to therapy (such as erlotinib) by analyzing cfDNA in the patient's plasma sample according to the low-error methods described herein.

Double Stranded Sequencing

In some embodiments, the invention is a method of analyzing nucleic acids that comprises a step of pairing sequencing reads to obtain a double-stranded (duplex) sequence. The first step in this embodiment is reading the nucleic acid sequence to determine the barcode. In some embodiments, the barcodes on the two strands are complementary to each other (e.g., if UID are located in the stem region of the adaptor.) In other embodiments, the non-random barcodes on the two strands are cross-referenced as located on single strands of the same adaptor molecule. In yet another embodiment, the barcode is a combination of the external and internal barcodes. The first step of pairing such sequences is reading and matching the short (2 or more base-pairs) external barcode. Next, a portion of the insert is also sequenced to determine genomic coordinates of the insert sequence. If the short barcodes are complementary to each other and the genomic coordinates of the insert map to the opposite strands, the reads represent reciprocal strands of a duplex molecule.

In some embodiments, the invention is a method of analyzing nucleic acids that comprises a step of error suppressing using barcodes. The method comprises a step of mapping the sequence to the reference genome and identifying all single nucleotide variants (SNVs) (i.e., bases different from the reference sequence). The method further comprises a step of subjecting the SNVs to quality filtering. In some embodiments, the quality filtering is Phred quality filtering using a threshold Q of 30, which eliminates 99.9% of errors arising from sequencing artifacts. The method further comprises a step of reducing errors by counting the number of SNVs for each genomic position (subjected to and having passed the quality filtering in the preceding step) and selecting the most abundant variant. The method further comprises a step of subtracting sequences with SNVs that have not passed the quality filtering from the group of sequences defined as a barcode family sharing the same UID. The method further comprises a step of consolidating all members of the barcode family into a single sequence, only keeping variants that pass step 3 with ≥2 members.

As a final error suppression step, all non-reference variants in singleton barcode families (i.e., families with one sequence) were eliminated unless supported by evidence from at least one other DNA molecule with ≥2 family members supporting that variant. We termed this deduping strategy "2×+singletons" (FIG. 9 (f)).

Estimating Tumor Burden

In some embodiments, the invention is a method of determining tumor burden in a patient by sequencing duplex molecules in the patient's cfDNA. Given the superior error rate of duplex sequencing, we sought to determine its LLOD for quantitating circulating tumor burden. The method comprises a step of designing a selector covering an adequate number (e.g., >1,500) of sequence variations, such as non-synonymous mutations. The selector may be designed by any survey method, e.g., exome sequencing of tumors. In some embodiments, a personalized selector may be designed by exome sequencing the patient's tumor. The method further comprises a step of duplex sequencing the patient's cfDNA. In some embodiments, as little as 1,000 genome equivalents may be recoverable in this step.

Figure 13:
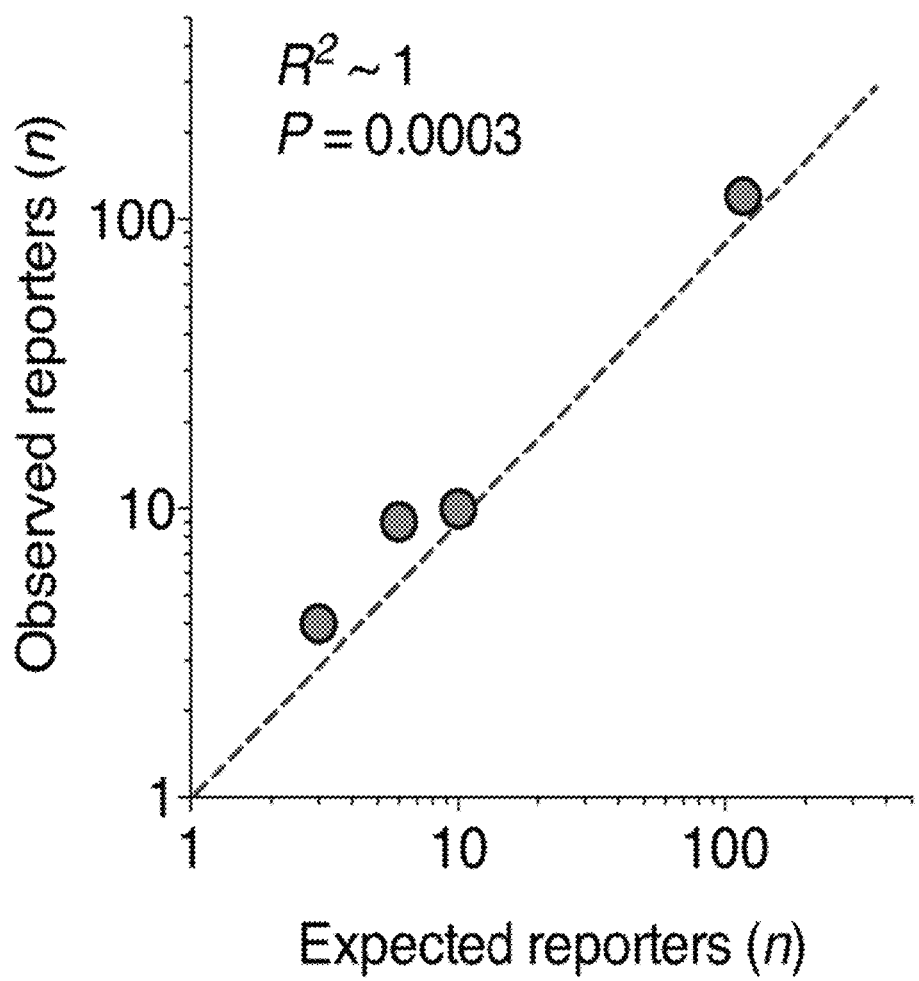
FIG. 13: Validating the analytical model for sensitivity

As demonstrated by the Examples, the method is able to accurately detect target sequences from 0.025% to 0.00025% with high linearity (FIG. 12 (i)), further validating our analytical model (FIG. 13) and demonstrating a detection limit of 2.5 molecules in the background of 1,000,000 molecules, nearly 100× below the LLOD of single allele dPCR. This suggests that personalized selectors are a promising approach for deep surveillance of microscopic residual disease, particularly for tumors with high mutational loads.

Collectively, the methods disclosed herein provide for a robust and flexible framework for ultrasensitive ctDNA profiling, achieved using accurate analytical models of detection limits, integrated digital error suppression, and adaptive cfDNA genotyping. By combining practical molecular barcoding implementations for error reduction and efficient duplex strand recovery with a generally applicable approach for removing residual background errors, iDES decreases error rates by 10-100-fold without sacrificing recovered genomic yields (FIG. 7(a)). These qualities improve detection limits over previous methods for samples with limited DNA content, such as clinically practical blood collection volumes (FIG. 7(b)). Moreover, by leveraging duplex strand recovery, our approach can be tuned to deliver exceptional sensitivity when sufficient tumor reporters and GEs are available. Given its advantages for ctDNA profiling, we anticipate that iDES will have broad utility for a variety of deep sequencing applications requiring precise digital quantification of low frequency alleles.

Maximizing Sensitivity while Minimizing Sequencing Cost

Circulating DNA has the potential to revolutionize the identification and monitoring of disease, e.g., cancer, but its detection in the blood, serum, and/or plasma of most patients has remained costly and challenging.

Disclosed herein includes a novel economical method that can combine ultra-deep sequencing and novel bioinformatics methods to achieve highly sensitive and specific noninvasive assessment of circulating DNA in the vast majority of patients. In some embodiments, the method can be applied to any type of cancer. The cancer may be a solid tumor, e.g., non-small cell lung cancer (NSCLC).

The method may also comprise designing and validating selectors (~200 kb) for each of these malignancies by combining bioinformatic analysis of publicly available somatic mutation data with prior knowledge of clinically relevant genomic regions and breakpoint hotspots.

Also disclosed herein are methods for rationally designing selectors to achieve a desired ctDNA detection limit, and validating modeling by empirical spiking experiments. For example, in some embodiments, the method disclosed herein can achieve a ctDNA detection limit of at least 1 in 50,000 molecules for all cancers, e.g., NSCLC, esophageal adenocarcinoma (EAC)/esophageal squamous cell carcinoma (ESCC), and pancreatic adenocarcinoma (PAAD) given an input of ~30 ng cfDNA at 50% capture efficiency (~3 mL plasma). In embodiments, the method comprises devising an algorithm to maximize sensitivity while minimizing sequencing cost, based on (i) the number of reporters identified in each tumor, (ii) the input plasma DNA mass, (iii) estimated DNA duplication rate and capture efficiency, and an empirically derived relationship between ctDNA levels and tumor volume (NSCLC only). In some cases, the method can comprise validating the electors by analyzing longitudinal plasma samples with paired tumor biopsies collected from a variety of NSCLC, EAC/ESCC, and PAAD patients spanning diverse stages, tumor volumes, and therapies.

Also disclosed herein are methods of determining the amount of the double-stranded nucleic acids and the number of the flow cells needed. The methods can comprise: a) determining parameters selected from a group consisting of: i) the sizes of the oligonucleotides in a selector; ii) the number of cancer reporters; iii) total genome equivalents; and iv) any combination thereof; b) applying an algorithm to the parameters in a) to determine the amount of the double-stranded nucleic acids and the number of the flow cells needed; and c) adjusting the amount of the double-stranded nucleic acids and the number of the flow cells to optimize cost.

In some embodiments, the cancer reporter may comprise cancer mutations. For example, the cancer reporters can be changes relative to the germline sequence, e.g. cancer cell specific changes. In other embodiments, the cancer reporters may include single nucleotide variants (SNV), copy number variants (CNV), insertions, deletions and rearrangements (e.g., fusions).

EXAMPLES

Example 1

Reducing Background Error with Molecular Barcoding

Barcodes were used to eliminate mutations due to background errors, such as errors caused by PCR and sequencing.

Cell-free DNA was isolated from patient blood samples. The cfDNAs were subject to end repairing and A-tailing (FIG. 1 (a)). A unique endogenous barcode for each cfDNA molecule was formed by the sequences at the start and end coordinates of a cfDNA.

Y-shaped adaptors, which comprise a hybridizable and a non-hybridizable portion, were then ligated to both ends of each cfDNA molecule by T4 DNA ligase (FIG. 1 (b)). The non-hybridizable portion of the Y-shaped adaptor comprised a four base random barcode and a four base fixed barcode, where the two barcodes were adjacent to each other (FIG. 1 (c)). The Y-shaped adaptor also comprised a universal sequence that can bind to a sequencing primer (FIG. 1 (c)). The combination of the random barcode and the endogenous barcode was used as a unique identifier for each of the resulted template nucleic acids. The fixed barcode was pre-defined to identify the source of the cfDNAs, e.g., the patient or the tissue from which the cfDNAs were isolated.

The resulting template nucleic acids were amplified by 12~14 cycles of PCR. The sequence information of the amplicons was then obtained by next generation sequencing, e.g., using Illumina HiSeq 2000. The sequence information comprised cancer-related mutations that occurred in vivo, e.g., real biological variants. However, the sequence information also comprised mutations due to errors introduced by PCR, sequencing or other artifacts (FIG. 1(d)).

In this example, since each template nucleic acid molecule was identified by a unique identifier, amplicons derived from the same template nucleic acid comprised the same unique identifier and were sorted accordingly. Mutations that were real biological variants occurred on the same locus while false mutations due to background errors occurred randomly on different loci. In addition, mutations due to background errors occurred on a subset of the amplicons derived from the same template nucleic acid. The amplicons derived from the same template nucleic acid were aligned based on the unique identifier and bioinformatic analysis was performed to filter out the mutations due to background errors, e.g., false mutations, which occurred randomly on different loci, or occurred on a subset of the amplicons derived from the same template nucleic acid. After false mutations were filtered out, the sensitivity of mutation detection in the sequence information was enhanced from 0.02% to 0.001% (FIG. 1 (e-g)), e.g., 1 tumor cell equivalent in a background of 99,999 normal cell equivalents.

Example 2

(Prophetic): Removing G to T Mutations with Molecular Barcoding

Cell-free DNA is isolated from patient blood samples. The cfDNAs are subjected to end repairing and A-tailing (FIG. 2 (a)). A unique endogenous barcode for each cfDNA molecule is formed by the sequences at the start and end coordinates of a cfDNA.

Figure 2A:
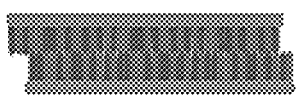
FIG. 2A-2C: Removing G to T mutations with molecular barcoding.
Figure 2B:
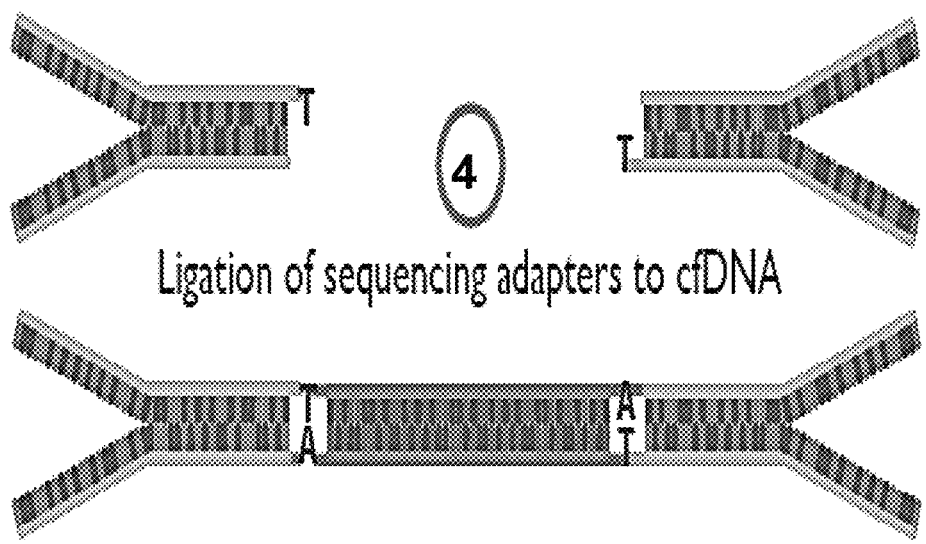
Figure 2C:
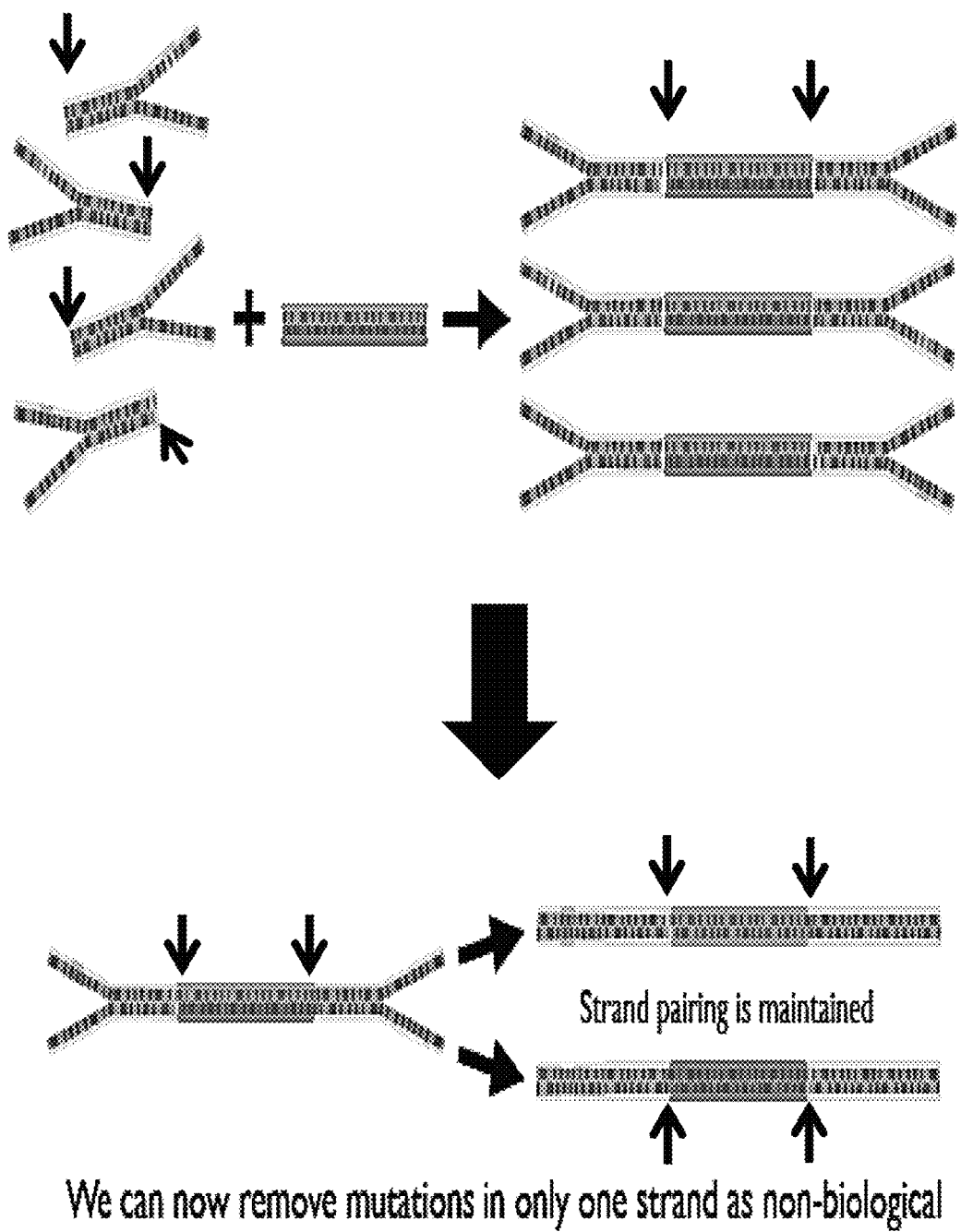

Y-shaped adaptors, which comprise a hybridizable and a non-hybridizable portion, are then ligated to both ends of each cfDNA molecule by T4 DNA ligase, to produce a plurality of template nucleic acids (FIG. 2 (b)). The non-hybridizable portion of the Y-shaped adaptor comprises a random barcode of four bases and a fixed barcode of four bases where the two barcodes are adjacent to each other (FIG. 2 (c)). The combination of the random barcode and the endogenous barcode is a unique identifier for each template nucleic acid. The fixed barcode is pre-defined to identify the source of the cfDNAs, e.g., the patient or the tissue from which the cfDNAs were isolated. Additionally, the Y-shaped adaptors also comprise a unique stem barcode of 2 base pairs (FIG. 2 (c)). After ligation, the stem barcodes are 2 base pairs away from the ligation site.

The resulting template nucleic acids are amplified by 12~14 cycles of PCR. The sequence information of the amplicons is then obtained by next generation sequencing by using Illumina HiSeq2000. The sequence information comprises cancer-related mutations that occur in vivo, e.g. real biological variants. However, the sequence information also comprises mutations due to errors introduced by PCR, sequencing or other artifacts, e.g., G to T mutations.

G to T mutations due to background errors occur on one strand, but not other strand of a template nucleic acid. Therefore, to reduce background, G to T mutations that occur on one strand, but not the other strand of a template nucleic acid are disregarded.

The double-stranded stem barcodes are used to identify the strand from which the amplicons are derived. Amplicons derived from a template nucleic acid comprise the same stem barcode and the same endogenous barcode. In addition, amplicons derived from different strands of the template nucleic acid comprise different random barcodes (FIG. 2 (c)). The amplicons derived from the same template nucleic acid are aligned based on the stem barcodes, the endogenous barcodes, and the random barcodes. The aligned amplicons comprise a first set of amplicons that have the stem barcode, the endogenous barcode and a random barcode, and a second set of amplicons that have the same stem barcode and the same endogenous barcode, but a different random barcode. G to T mutations are then disregarded if they occur on 99.9% of the first set of amplicons, but on less than 1% of the second set of amplicons.

Example 3

(Prophetic): Reducing Background Error Using Double-Stranded Stem Barcodes and Endogenous Barcodes A cfDNAs is isolated from a patient blood sample and subsequently end repaired and subject to A-tailing. A unique endogenous barcode for each cfDNA molecule is formed from the sequences at the start and end coordinates of a cfDNA.

Y-shaped adaptors, which comprise a hybridizable and a non-hybridizable portion, are then ligated to both ends of each cfDNA molecule by T4 DNA ligase. Each Y-shaped adaptor comprises a universal sequence that can bind to a sequencing primer. The sequence of the fixed barcode is pre-defined to identify the source of the cfDNAs, e.g., the patient or the tissue from which the cfDNAs were isolated. The hybridizable portion of each Y-shaped adaptor comprises a double-stranded stem barcode 2 base pairs away from the ligation site.

The resulting ligated template nucleic acids are amplified by 12-14 cycles of PCR. The amplicons are then sequenced by next generation sequencing by using Illumina HiSeq2000. The sequence information comprises cancer-related mutations that occur in vivo, e.g. real biological mutations. However, the sequence information also comprises mutations due to background error, e.g., false mutations, introduced by PCR, sequencing, or other artifacts.

After ligation, each double-stranded cfDNA fragment is attached a double-stranded stem barcode. Amplicons derived from one strand and amplicons derived from the other strand of the double-stranded cfDNA comprise the same double-stranded stem barcodes and the same endogenous barcodes. Real biological mutations occur at the same locus on all amplicons that contain the locus. False mutations comprise mutations that occur on amplicons derived from only one of the two strands of the double-stranded cfDNAs. Therefore, false mutations can occur on about 50% of the amplicons with the same stem barcode and the same endogenous barcode.

In this example, amplicons are aligned based on the stem barcodes and endogenous barcodes. False mutations that only occur on about 50% of the amplicons are filtered out.

Sensitivity of mutation detection in the sequence information is enhanced by filtering out the false mutations.

Example 4

Noninvasive and Ultrasensitive Detection of Circulating DNA from Solid Tumors

Figure 4:
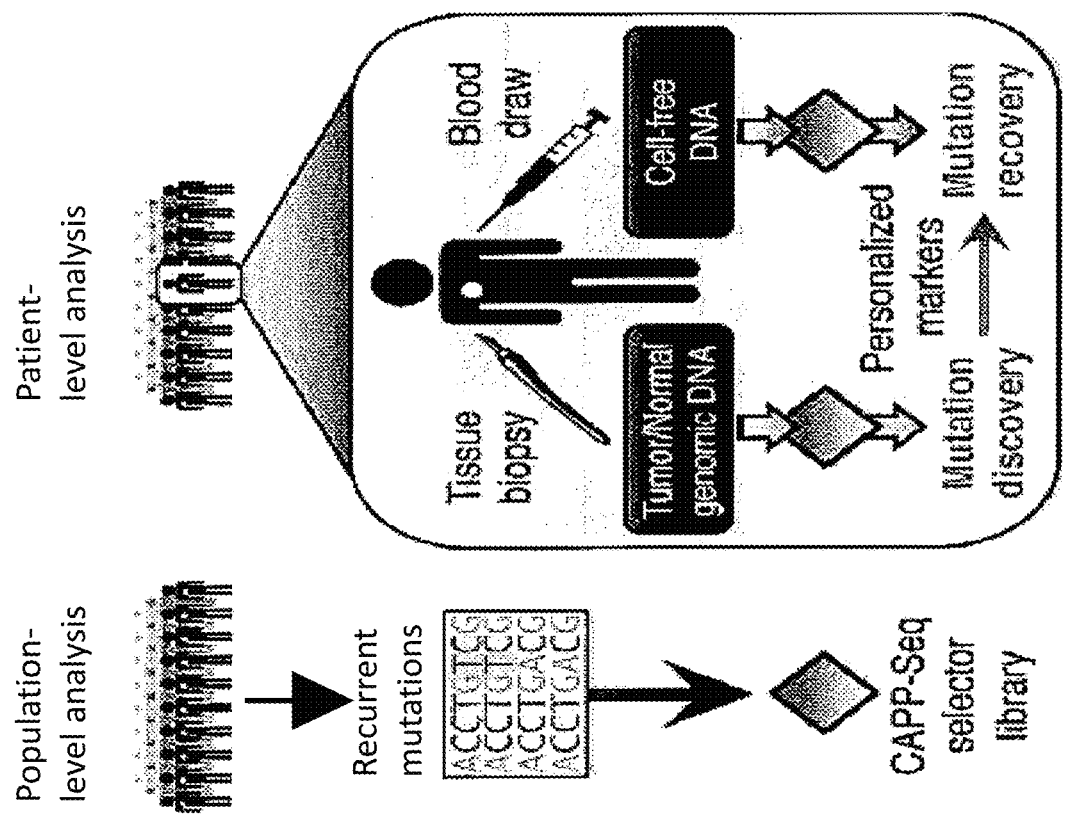
FIG. 4: Development of CAncer Personalized Profiling by Deep Sequencing (CAPP-Seq). Schematic depicting design of CAPP-Seq selectors and their application for assessing circulating tumor DNA.
Figure 5B:
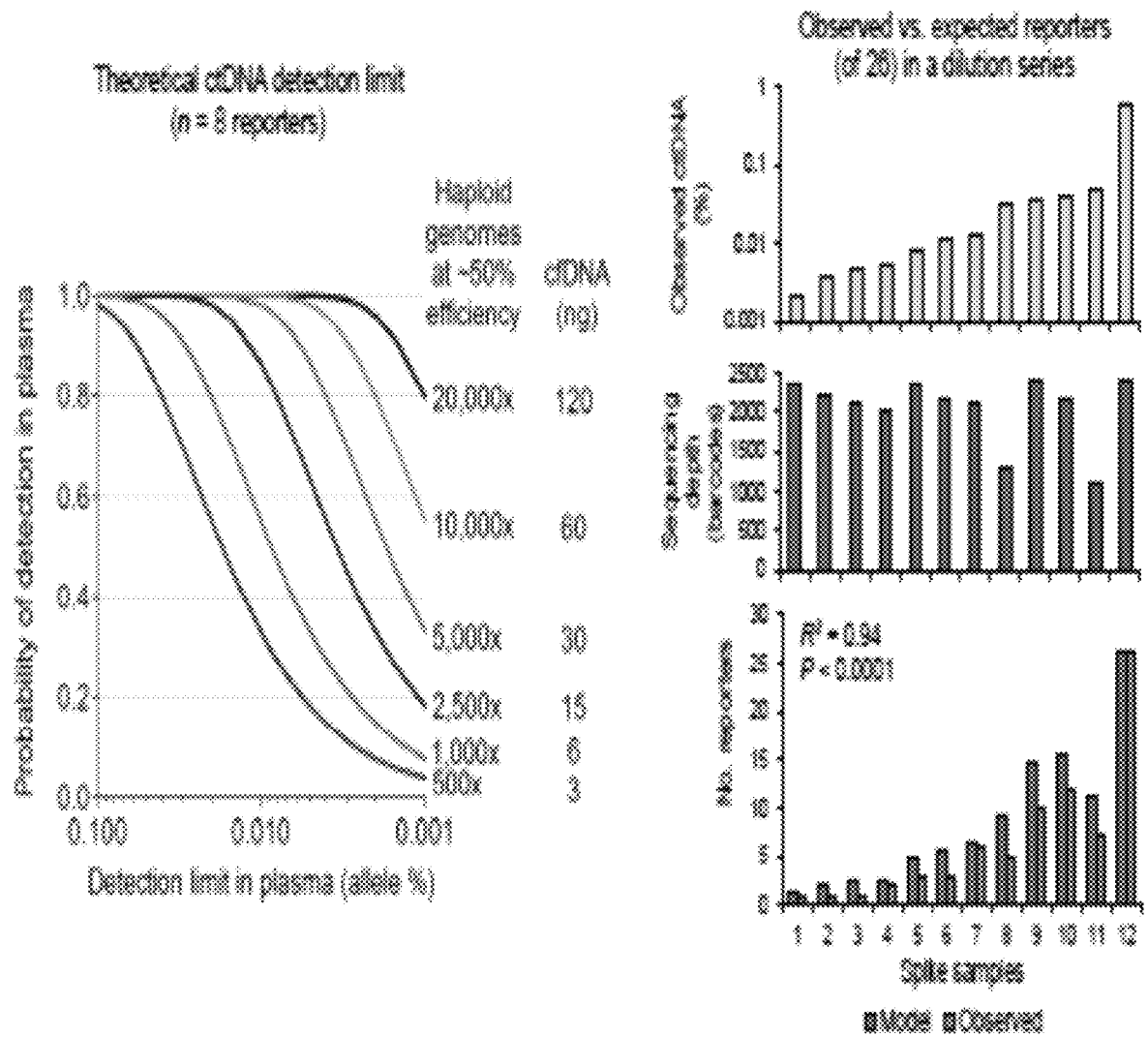
Figure 5C:
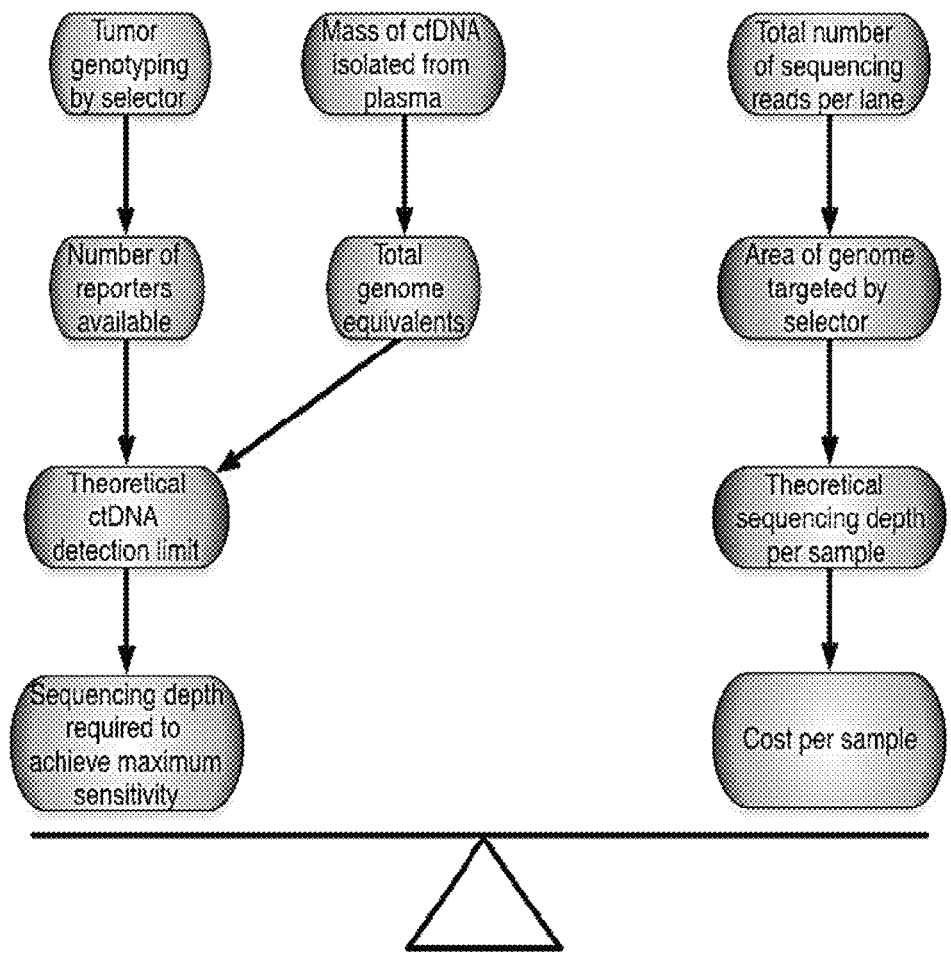
Figure 6A:
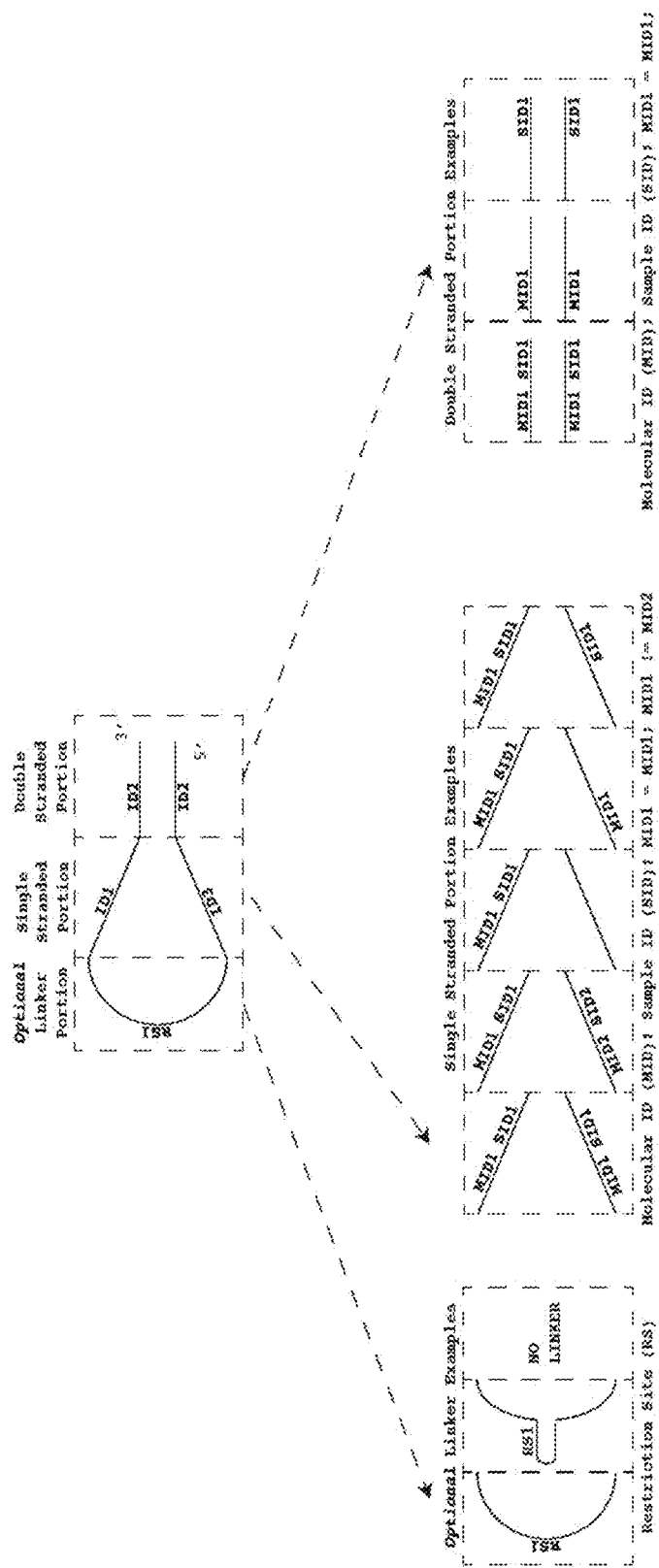
FIG. 6A-6E: Structure and performance of tandem barcode adaptors and tandem staggered barcode adaptors with and without linkers (Y-shaped and covalently closed ends).
Figure 6B:
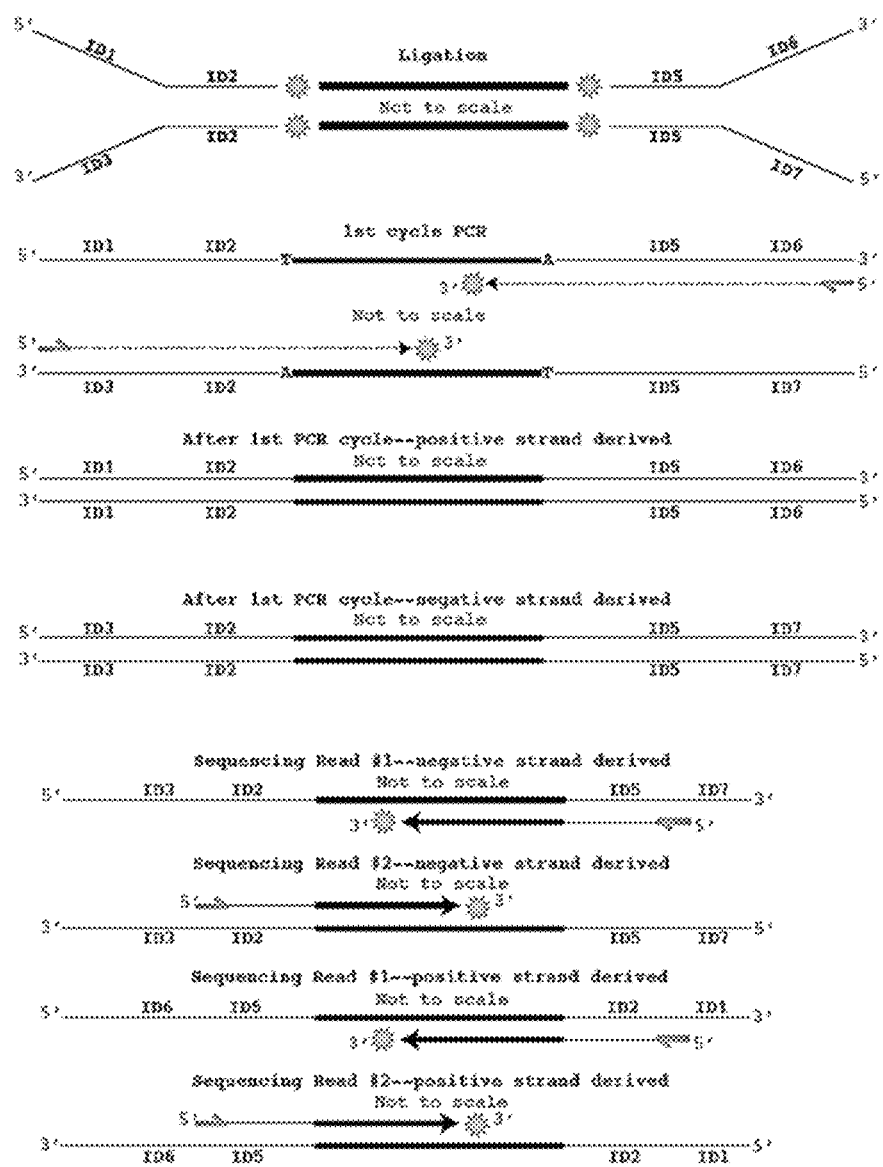
Figure 6C:
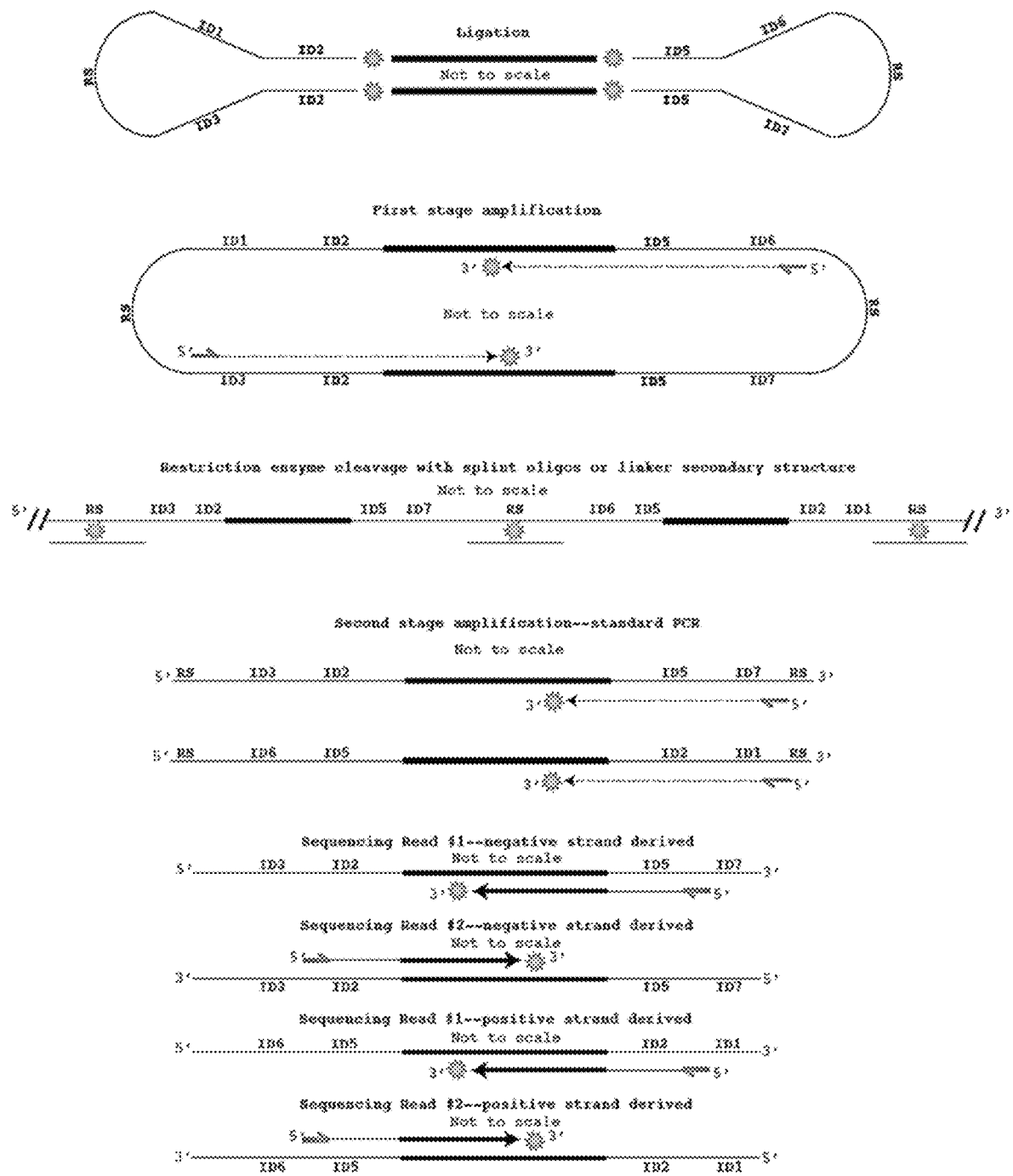
Figure 6D:
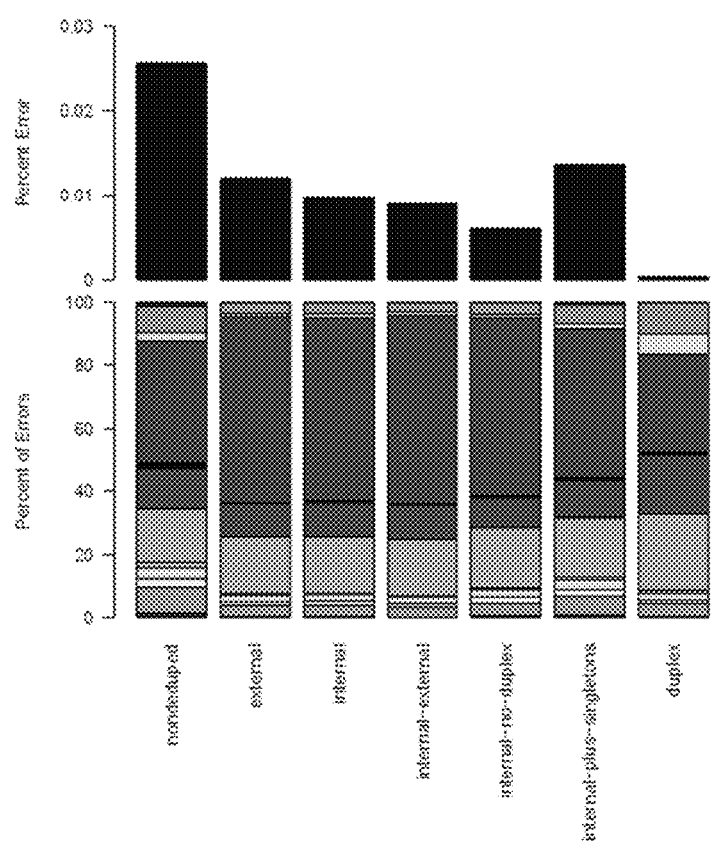
Figure 6E:
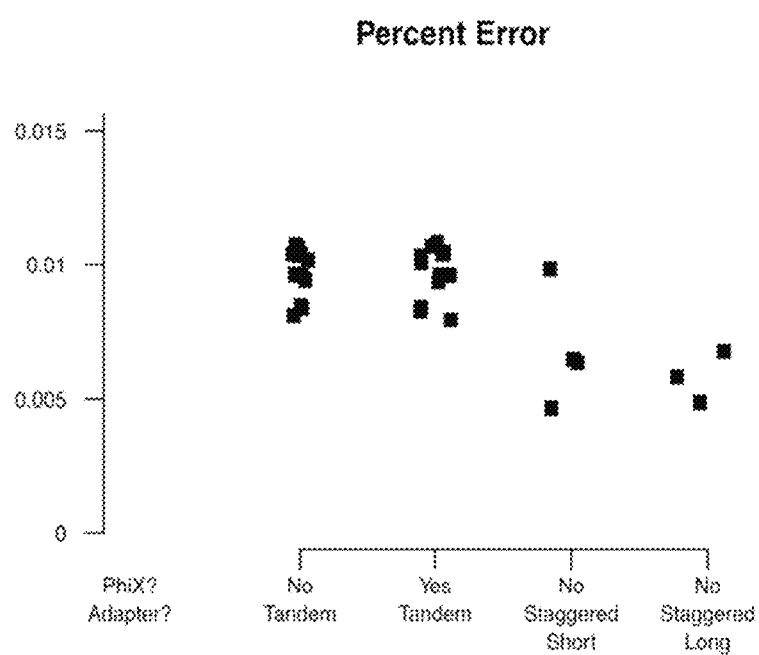

We developed an economical new method that combined ultra-deep sequencing and novel bioinformatics methods to achieve highly sensitive and specific noninvasive assessment of ctDNA in the vast majority of patients. We applied the method, called CAPP-Seq (FIG. 4), to three major solid cancer types, non-small cell lung cancer (NSCLC), esophageal adenocarcinoma (EAC)/esophageal squamous cell carcinoma (ESCC), and pancreatic adenocarcinoma (PAAD). By combining bioinformatic analysis of publicly available somatic mutation data (Table 1) with prior knowledge of clinically relevant genomic regions and breakpoint hotspots, we designed and validated CAPP-Seq selectors (~200 kb) for each of these malignancies (FIG. 5 (a)). We developed analytical models to rationally design selectors to achieve a desired ctDNA detection limit, and validated our modeling by empirical spiking experiments (FIG. 5 (b)). On this basis, we expected to achieve a ctDNA detection limit of at least 1 in 50,000 molecules for all three cancers, given an input of ~30 ng cfDNA at 50% capture efficiency (~3 mL plasma). Based on (i) the number of reporters identified in each tumor, (ii) the input plasma DNA mass, (iii) estimated DNA duplication rate and capture efficiency, and an empirically derived relationship between ctDNA levels and tumor volume (NSCLC only), we devised an algorithm ("Lane Balancing Algorithm") to maximize sensitivity while minimizing sequencing cost (FIG. 5 (c)). The CAPP-Seq selectors were validated by analyzing longitudinal plasma samples with paired tumor biopsies collected from a variety of NSCLC, EAC/ESCC, and PAAD patients spanning diverse stages, tumor volumes, and therapies (Table 2).

TABLE 1

Somatic mutation source data

| PMID | Author, Year | Method | No. Patients | Disease |
|---|---|---|---|---|
| — | TCGA | WES | 381 | LUAD |
| 22960745 | TCGA, 2012 | WES | 176 | LSCC |
| 22980975 | Imielinski et al., 2012 | WGS | 24 | LUAD |
| 22980975 | Imielinski et al., 2012 | WES | 148 | LUAD |
|  |  | Total | 553/176 | LUAD/LSCC |
| 23525077 | Dulak et al., 2013 | WES | 149 | EAC |
| 22877736 | Agrawal et al., 2012 | WES | 11-Dec | ESCC/EAC |
|  |  | Total | 161/11 | EAC/ESCC |
| Unpublished | TCGA | WES | 59 | PAAD |
|  |  | Total | 59 | PAAD |

TABLE 2

Patient details

| Patient ID | Primary site | Sex | Age at diag. | Histology | Stage | Tumor volume (cc) | No. of plasma samples | No. SNVs & indels | Smoking history | Treatment and last follow-up (if available) |
|---|---|---|---|---|---|---|---|---|---|---|
| LUP2 | Lung | M | 61 | Large Cell | III |  | 4 | 29 | Heavy | Surgery, ChemoRT; Complete response |
| LUP6 | Lung | M | 55 | Adeno | IV |  | 2 | 8 | Never | Cis/pem; Progressive disease |
| LUP18 | Lung | M | 56 | Adeno | IIA | 150.5 | 2 | 25 | Light | Radiation; Complete response |
| LUP19 | Lung | F | 81 | Small Cell | IB | 43.2 | 2 | 8 | Heavy | Radiation; Complete response |
| LUP20 | Lung | F | 80 | Adeno | IB | 33.5 | 4 | 9 | Never | Radiation; Progressive disease |
| LUP21 | Lung | F | 78 | NSC | IB | 24.9 | 4 | 6 | Smoker | Radiation; Complete response |
| LUP22 | Lung | F | 46 | Adeno | IV | 10.42 | 5 | 2 | Never | TKI CO-1686; Mildly progressive disease |
| LUP23 | Lung | M | 89 | Adeno | IA | 9.9 | 7 | 52 | Heavy | TBD |
| LUP24 | Lung | F | 68 | Adeno | IIB | 8.3 | 4 | 4 | Heavy | Radiation; Complete response |
| LUP25 | Lung | M | 45 | NSC | IIIB | 57.6 | 7 | 4 | Never | Erlotinib, Hydroxychloroquine, and CO-1686; Progressive disease |
| LUP26 | Lung | F | 57 | Adeno | IIIB | 86.4 | 4 | 33 | Heavy | ChemoRT, adjuvant chemo; Complete response |
| EP1 | Esophagus | M | 67 | Adeno |  | 20.4 | 5 | 8 |  | Intensity modulated radiation therapy |
| EP2 | Esophagus | F | 68 | Adeno |  | 45.9 | 4 | 16 |  | Intensity modulated radiation therapy |
| EP3 | Esophagus | M | 78 | Squam |  | 42.7 | 5 | 4 |  | Proton therapy |
| EP5 | Esophagus | M | 64 | Adeno |  | 96.7 | 5 | 5 |  | Induction chemotherapy; Proton therapy |
| EP7 | Esophagus | M | 55 | Adeno |  | 19.3 | 5 | 6 |  | Proton therapy |
| EP8 | Esophagus | M | 69 | Squam |  | 13.9 | 5 | 6 |  | Proton therapy |
| EP9 | Esophagus | M | 60 | Squam |  | 15.2 | 5 | 3 |  | Intensity modulated radiation therapy |

TABLE 2-continued

Patient details

| Patient ID | Primary site | Sex | Age at diag. | Histology | Stage | Tumor volume (cc) | No. of plasma samples | No. SNVs & indels | Smoking history | Treatment and last follow-up (if available) |
|---|---|---|---|---|---|---|---|---|---|---|
| EP10 | Esophagus | M | 57 | Adeno | | 23.1 | 4 | 15 | | Proton therapy |
| EP11 | Esophagus | M | 59 | Adeno | | 70.1 | 5 | 5 | | Induction chemo; Intensity modulated radiation therapy |
| EP12 | Esophagus | M | 54 | Adeno | | 208.3 | 5 | 12 | | Intensity modulated radiation therapy |
| PP1 | Pancreas | M | 66 | Adeno | IV | 64.7 | 3 | 45 | | ChemoRT; Progressive disease |
| PP2 | Pancreas | M | 65 | Adeno | IIB (vs III) | 112.8 | 2 | 32 | | ChemoRT |
| PP3 | Pancreas | M | 65 | Adeno | IIB | 250.8 | 2 | 0 | | Surgery, ChemoRT; Stable for 1.25 yrs; Progressed on chemo |
| PP4 | Pancreas | M | 58 | Adeno | IIB (vs IV) | 84.7 | 1 | 2 | | ChemoRT; Progressive disease |
| PP5 | Pancreas | F | 76 | Adeno | III | 335.8 | 2 | 2 | | ChemoRT; Progressive disease |
| PP6 | Pancreas | M | 56 | Adeno | IIB | 236.9 | 3 | 0 | | Surgery and chemo; Progressive disease |
| PP7 | Pancreas | M | 30 | Adeno | III | 62.6 | 1 | 7 | | ChemoRT; Progressive disease |
| PP8 | Pancreas | M | 68 | Adeno | IIB | 14.1 | 1 | 0 | | Surgery, chemoRT; Progressive disease |
| PP9 | Pancreas | M | 59 | Adeno | III | 152.3 | 5 | 2 | | Chemo; Progressive disease |
| PP10 | Pancreas | F | 64 | Adeno | IV | 25.7 | 4 | 13 | | Chemo; Progressive disease |
| PP11 | Pancreas | F | 74 | Adeno | IIA | 55.3 | 1 | 3 | | Surgery, chemoRT; No evidence of disease-> lost to followup |
| PP12 | Pancreas | M | 66 | Adeno | III | 150.2 | 4 | 12 | | ChemoRT; Progressive disease |

By integrating prior knowledge of driver genes, resistance mutations and breakpoint hotspots with bioinformatic selection (e.g., by calculating Recurrence Index) of recurrently mutated (non)coding regions, three solid tumor CAPP-Seq selectors were designed: i) NSCLC selector (203 kb) that covers nearly 100% of NSCLC tumors with a median of 8 mutations per patient; ii) EAC/ESCC selector (180 kb) that covers nearly 100% of EAC/ESCC tumors with a median of 7-8 mutations per patient; iii) PAAD selector (185 kb) that covers ~85% of pancreatic adenocarcinoma tumors with a median of 8-11 mutations per patient. An analytical model was devised and validated to predict the detection limit of ctDNA in plasma given the number of tumor reporters and genome equivalents sequenced. Using optimized lane loading, over-sequencing (e.g., cost) can be minimized while the ctDNA detection limit in plasma for a clinically-diverse set of NSCLC, EAC/ESCC, and PAAD patients can be maximized.

Example 5

Patients and Samples

Patient selection. All patient samples in this study were collected with informed consent for research use and were approved by the Stanford Institutional Review Board in accordance with the Declaration of Helsinki.

Blood collection and processing. Blood was drawn in BD Vacutainer purple top 10 mL K2 EDTA tubes (Becton Dickinson, Franklin Lakes, N.J. catalog #366643). Tubes were spun at 1800×g for 10 mins, then plasma was removed in 1-2 mL aliquots to 1.5 or 2 mL tubes, then frozen at −80° C. until cfDNA isolation. A small amount of plasma was mixed with the buffy coat and red cell pellet, then transferred to 1.5 mL tubes, which were frozen at −80° C. until germline DNA isolation.

DNA isolation. cfDNA was isolated from plasma samples using the QiaAmp Circulating Nucleic Acid Kit (Qiagen, Valencia, Calif.) according to manufacturer's instructions. Germline DNA was isolated from the cellular fraction of blood using the QiaAmp DNA Micro Kit (Qiagen) according to manufacturer's instructions. For DNA isolation from FFPE tumor samples, first, 4 sections of 10 um (surgical specimens) or 20 um (fine needle aspirates) were collected using a Leica RM 2155 rotary microtome with Leica low profile disposable blades. Following this, the Qiagen All-Prep DNA/RNA FFPE kit was used to isolate DNA from the sections according to manufacturer's instructions. After isolation, DNA was quantified using the Qubit dsDNA High Sensitivity kit (Life Technologies, Grand Island, N.Y.) according to manufacturer's instructions.

Shearing of genomic DNA. Germline DNA and DNA from FFPE was sheared prior to library preparation to achieve a median size of ~170-250 base pairs. When possible, 100-2000 ng of DNA was used as input for shearing, but CAPP-Seq was performed successfully on smaller amounts of DNA. Input DNA was diluted to 120 uL using water or Tris EDTA buffer pH 8.0. Shearing was performed with the Covaris S2 sonicator and Covaris Micro tubes (Covaris, Woburn, Mass. catalog #520045) with the following conditions: 10% duty cycle, intensity level 5, 200 cycles per burst, 120 second duration. After shearing, DNA was purified using a QiaQuick PCR purification kit (Qiagen), and eluted in 50 uL Buffer EB. Post-sonication, DNA was quantified using the Qubit dsDNA High Sensitivity kit, and the size distribution of some samples were validated using the Agilent Bioanalyzer High Sensitivity DNA kit (Agilent, Santa Clara, Calif., catalog #5067-4626).

Preparation of pre-capture sequencing libraries. The amount of DNA used as input for the sequencing libraries varied depending on the type of DNA input (cfDNA, germline, or FFPE tumor DNA), how many samples would be multiplexed in one sequencing lane, and the amount of DNA isolated. Typically, a maximum of 32 ng cfDNA were input for a cfDNA sample that was 12-plexed in an Illumina HiSeq 2000 High Output lane, while up to 100 ng germline or tumor DNA was used as input for a 24-plexed Illumina HiSeq 2000 High Output lane. Sequencing library preparation was performed using the KAPA LTP Library Prep Kit (Kapa BioSciences, Wilmington, Mass.), with some modification to manufacturer's protocol. DNA was diluted to 50 uL in water or EB, then end repair and the first Agencourt Ampure XP (Beckman Coulter, Pasadena, Calif.) bead cleanup were performed according to manufacturer's instructions. A-tailing and the second Ampure bead cleanup were performed mostly according to manufacturer's instructions, but a 5 minute incubation at 70° C. was added after the 30° C. incubation to inactivate the A-tailing enzyme. Ligation was performed using 100-fold molar excess of adaptors relative to the input DNA samples, with a 16° C. incubation overnight. After ligation, DNA was isolated with a stringent Ampure bead cleanup, and eluted into 24 uL of water or EB. PCR was performed with KAPA HiFi and Illumina Universal Primers (2 uM final concentration of each primer) with an annealing step of 30 seconds at 60° C. and an extension step of 30 seconds at 72° C. The number of PCR cycles was optimized to perform the minimum number of cycles expected to give 3000 ng of DNA for an entire lane (so, if a sample was to be used for 1/12 of a lane, the minimum expected number of PCR cycles to obtain 250 ng were performed). PCRs were purified by one or two rounds of Ampure bead purification and then eluted into 60 uL water. Libraries were quantified by Qubit and the size distribution of libraries was determined using the Agilent Bioanalyzer High Sensitivity DNA kit. If adaptor dimers were present at a molar ratio of greater than 5%, another stringent Ampure cleanup was performed to remove them. If less DNA than necessary was present, more PCR cycles were performed, followed by one or two stringent Ampure cleanups.

Hybridization-based enrichment of specific sequences from the sequencing libraries. For the hybridization-based enrichment of specific sequences, a custom designed pool of biotinylated DNA oligos was used. The pool was supplied by NimbleGen as a custom SeqCap reagent, then diluted 10-fold in water, and aliquotted into 4.6 ul aliquots, which were stored at −20° C. until use. Sequencing libraries were combined to a total mass of 1500 ng, then 500 ng was removed to be used for QC later. To the other 1000 ng, 5 uL 1 mg/mL Human Cot1 DNA (Invitrogen, San Diego, Calif.) and 1 uL each of 1 mM xGen Universal Blocking Oligo-TS-p5 and xGen Universal Blocking Oligo-TS-p7(8 nt) (IDT) were added. For each 1000 ng sample, a 4.6 uL selector aliquot was thawed and pre-heated to 47° C. Hybridization and cleanup were performed using a Nimblegen SeqCap EZ Hybridization and Wash kit (NimbleGen, Madison, Wis.), according to manufacturer's instructions. After washes, the beads were suspended in 96 uL water, and split into 4 50 ul PCR reactions using KAPA HiFi polymerase and Illumina universal primers (2 uM final concentration). 15 cycles of PCR were performed, the 4 reactions were combined, and DNA was isolated using a Qiaquick PCR purification kit.

Assessment of library quality and enrichment following hybridization. The sequencing libraries were quantified using the Qubit dsDNA High Sensitivity kit. Then the size distribution and molarity of the libraries were determined using the Agilent Bioanalyzer High Sensitivity DNA kit. To assess enrichment, qPCR was performed in triplicate on a 20× dilution of the final sample, and a 20× dilution of the pre-capture combined libraries using 7 amplicons: Nimblegen internal control sequences NSC1-4, ALK1 intron 19, KRAS exon 2, EIF2C1 negative control. In order to assess enrichment for each primer pair, the delta CT=(pre-capture Ct)−(post-capture Ct) was calculated, then the following efficiency values were used to calculate unadjusted fold enrichment: NSC1, 1.84; NSC2, 1.8; NSC3, 1.78; NSC4, 1.93; ALK, 1.7; KRAS, 1.7. The Qubit readings from before and after capture were used to adjust the enrichment values to account for the mass of DNA used in qPCR. Generally, enrichment values for NSC1-4 were over 70, and enrichment values for KRAS and ALK were over 800. If poor enrichment was seen (under ~50 for NSC1-4), the pre-capture sample was captured and PCR was performed again.

Example 6

Preparing Adaptors

To make the index adaptors, standard 8-base barcode Illumina adaptors were used, replacing the 8-base indexes with 4 random bases followed by a 4-base multiplexing barcode. 24 different adaptor sequences were designed such that all pairs of multiplexing barcodes had edit distances of at least 2.

Tandem adaptors were designed with index adaptors as a starting point. 12 index adaptors with pairwise edit distances of at least 3 were used. To each adaptor, 2 bases were added to the internal end of each adaptor oligonucleotide, followed by a GT on the 3' end of one oligonucleotide, and a C on the 5' end of the other. For the GT, the T was required to allow ligation, and the G was chosen to allow a consistent GC clamp base pair at the end of the adaptor. For each of the 12 multiplexing barcodes, 16 pairs of oligonucleotides were ordered, one for each dinucleotide. Before using the adaptors, they were annealed as described below.

Staggered tandem adaptors were designed with tandem adaptors as a starting point—6 of the tandem adaptors had 2 bases added immediately distal to the GT at the internal end of the adaptor. The sequence of these 2 bases was determined by the other internal barcode bases, keeping only 16 possible 4-base barcodes. For 8 of these barcodes, the GT at the end of the adaptor was replaced with a CT.

To anneal adaptors, 20 uL of each of 2 100 uM adaptor oligos were combined in a 50 uL reaction volume with a final concentration of 10 mM Tris/10 mM NaCl pH 7. The adaptors were annealed using an Eppendorf VapoProtect Thermocycler (Eppendorf, Hamburg, Germany) according to the manufacturer's instructions. After annealing, the adaptors were diluted to 15 uM using 10 mM Tris/10 mM NaCl pH 7.5. For index adaptors, the Illumina universal adaptor oligo was ligated with each of 24 index adaptor oligos. For each of the 12 tandem adaptors, 16 annealing reactions were performed: one for each dinucleotide barcode at the end of the adaptor. These 16 annealing reactions were combined at equal concentrations after annealing, before dilution to 15 uM.

Example 7

Processing of Molecular Barcodes

Read sequences were processed to extract 4-bp index and/or insert barcode sequences. The latter were originally split across each end of a given read pair (FIG. 6 (a)), and were concatenated prior to analysis. To recover duplex sequences with insert barcodes, we used the following criteria, illustrated by way of example: Suppose AT and CG insert barcodes are observed in read 1 and 2, respectively, and their corresponding DNA fragment $F_1$ aligns to the positive strand of the reference genome. If AT and CG barcodes are then respectively observed in read 2 and read 1 from another fragment $F_2$ aligned to the minus strand, and if the two fragments share genomic coordinates, then $F_1$ and $F_2$ likely represent reciprocal strands of a duplex molecule. All insert barcodes were analyzed accordingly. Otherwise, both barcode types were treated in an identical fashion. Prior to barcode deduping, all reads were mapped to the reference genome and all single base variants (i.e., bases different from the reference) were subjected to Phred quality filtering using a threshold Q of 30, which eliminates 99.9% of errors arising from sequencing artifacts. After base quality filtering, each barcode family with ≥2 members was analyzed separately to identify and eliminate additional errors as follows:

1) For every genomic position i in a given barcode family, count the number of distinct non-reference variants $v_i$, considering only variants that pass base quality filtering. If there is >1 distinct non-reference variant with Q≥30 at a given position i, set $v_i$ equal to the most abundant high quality variant, or in the event of a tie, arbitrarily choose one of the variants.

2) For each position harboring a candidate variant from step 1 (i.e., $v_i$>0), adjust the number of barcode family members $n_i$ by subtracting the number of non-reference variants $q_i$ that fail the Phred quality filter. Therefore, $n_i^* = n_i - q_i$.

3) Eliminate all non-reference variants from step 2 where $v_i < (f \times n_i^*)$, where f=1, by default.

4) Consolidate all members of the barcode family into a single sequence, only keeping variants that pass step 3 with ≥2 members.

As a final error suppression step, all non-reference variants in singleton barcode families (i.e., families with one sequence) were eliminated unless supported by evidence from at least one other DNA molecule with ≥2 family members supporting that variant. We termed this deduping strategy "2×+singletons" (FIG. 9 (f)).

Example 8

Statistical Analysis

We modeled the probability of detecting ctDNA as follows. Let n=number of sequenced genome equivalents, d=detection limit (fraction of ctDNA molecules), and k=number of tumor reporters. The probability of observing a single tumor reporter in cfDNA is Poisson with mean $\lambda = n \times d$, where $\lambda$ denotes the expected number of mutant allele copies. Therefore, given 1 reporter, the probability x of detecting ≥1 ctDNA molecule is equal to 1—Poisson($\lambda$), which simplifies to: (1) $x = 1 - e^{-nd}$ Generalizing to k independent tumor reporters (FIG. 16), the cumulative distribution function of a geometric distribution can be used to model the probability of observing a success (i.e., detection of ≥1 ctDNA molecule). Thus, the probability p of detecting ≥1 ctDNA molecule given k reporters is $1-(1-x)^k$. Plugging in (1) for x yields:

(2) $p = 1 - e^{-ndk}$

This equation can be used to solve for any parameter if the other three are specified. For example, given 1 reporter (k), 2,000 GEs (n), and 90% confidence (p), the detection limit d is equal to 0.12% (i.e., $d = \ln(1-p)/(-nk)$). Finally, the number of tumor reporters needed to observe one reporter in cfDNA is equal to 1/x (mean of a geometric distribution) and the number of expected reporters in plasma is equal to $k \times x$.

Example 9

Background Polishing

Figure 14A:
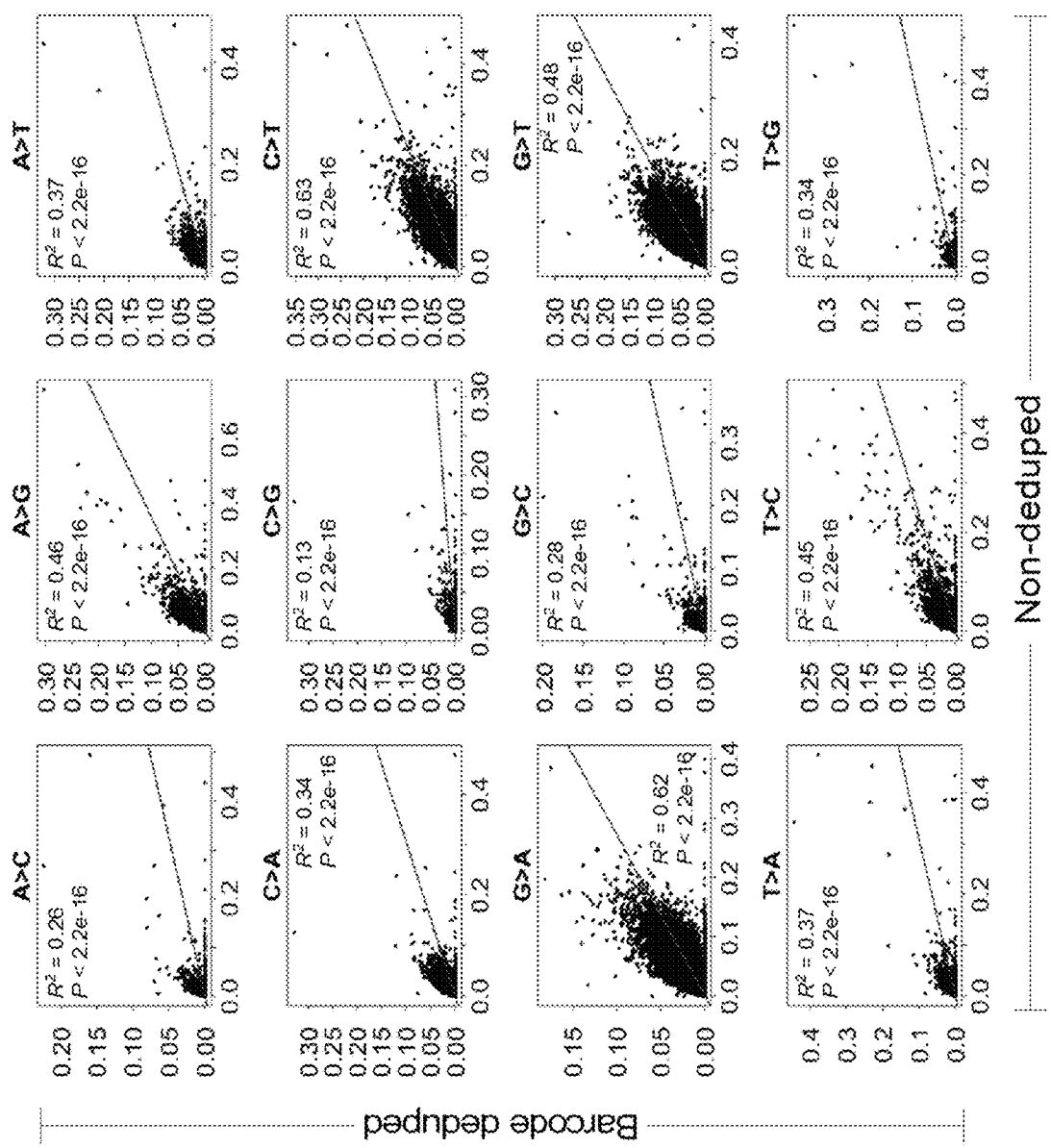
FIG. 14-14B: Probability distribution model for each type of base substitution
Figure 14B:
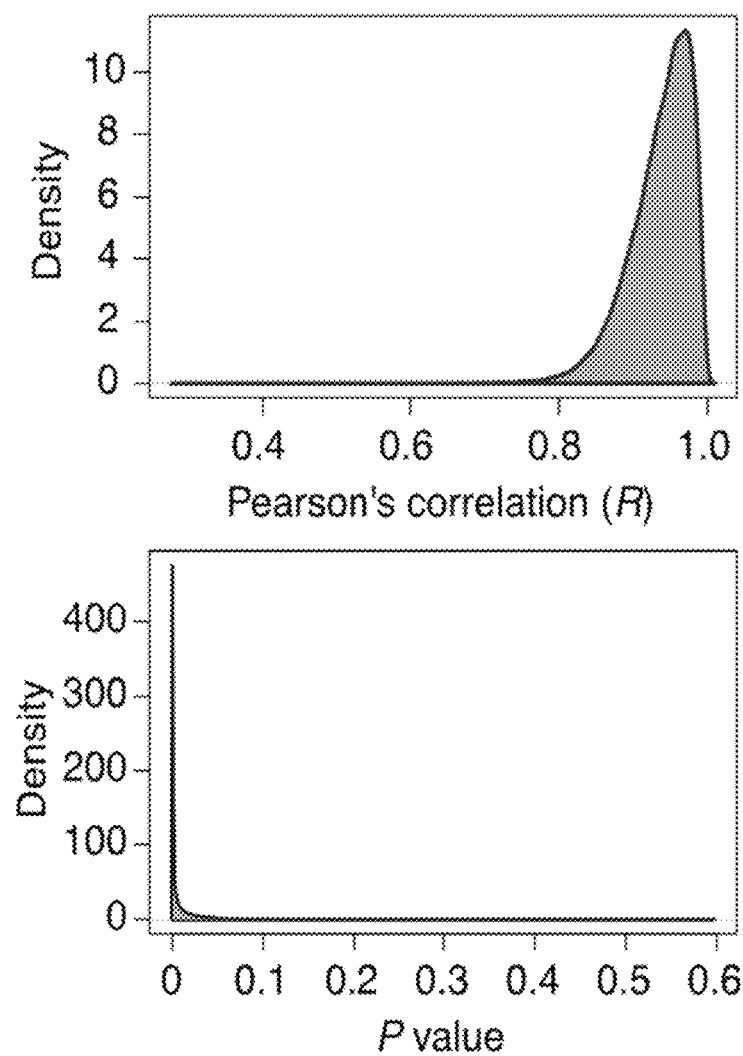
Figure 15A:
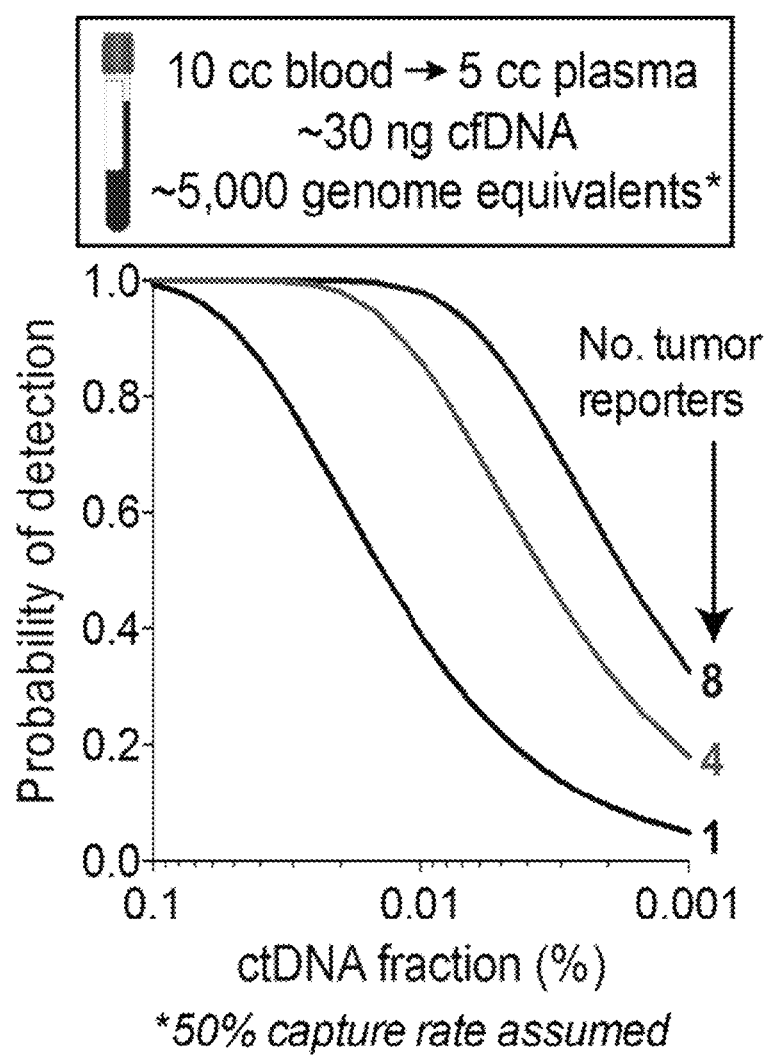
Figure 15B:
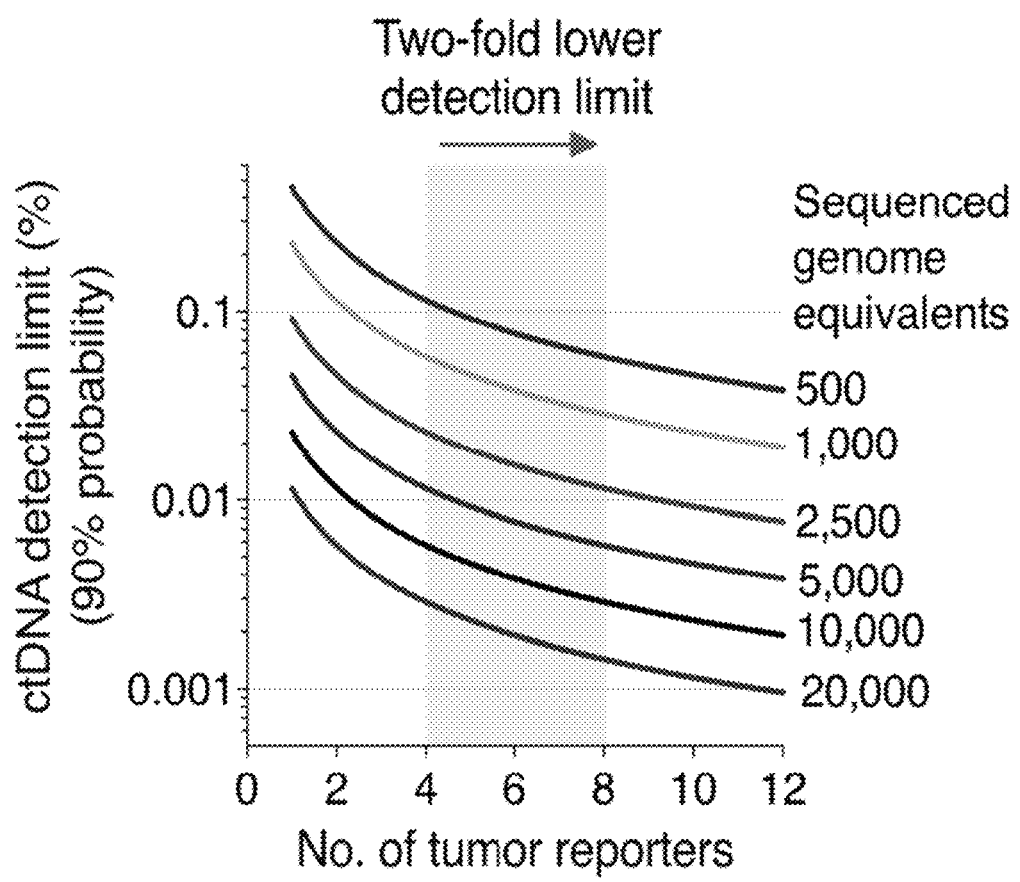
Figure 15F:
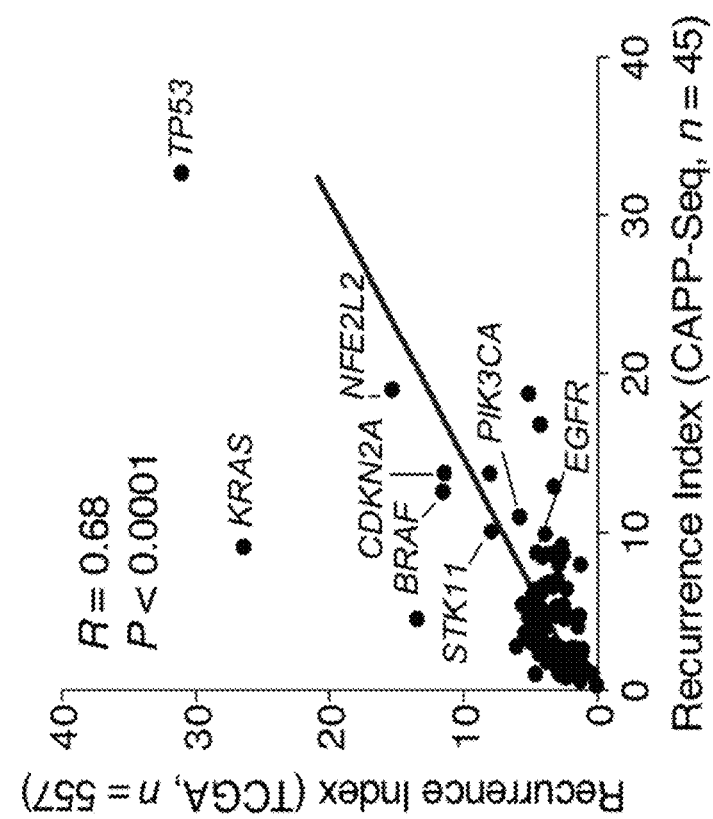
Figure 15E:
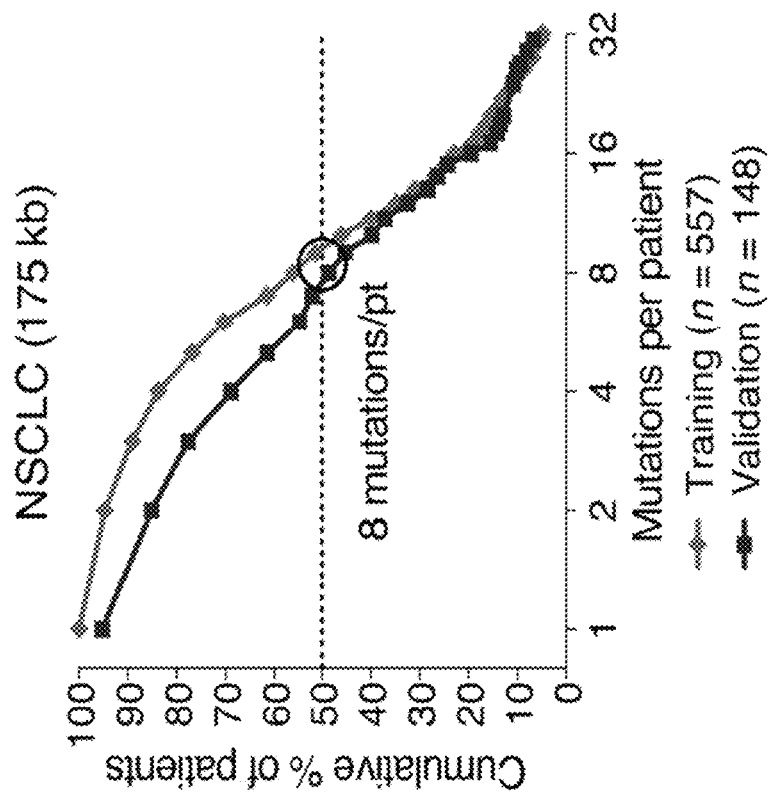

To explicitly model position-specific background distributions in cfDNA, we employed a novel approach alternately employing two statistical models depending on available information content. First, we compiled a training cohort of 12 normal control cfDNA samples with high background (FIG. 9 (c)). We then iterated through every possible SNV in the NSCLC clinical selector (~1.2M; excluding germline SNPs), and for each, we populated a position- and base substitution-specific one-dimensional vector v with all allele fractions (AFs) observed in the set of 12 normal cfDNA controls. To mitigate the impact of outliers, we removed the maximum AF from v, leaving 11 remaining elements. If the total number of non-zero AFs in v was less than 4, we used a Gaussian distribution to model the entire vector, and calculated the mean μ and standard deviation σ using all 11 AFs. Otherwise, we fit a Weibull distribution to the set of non-zero AFs in v using fitdist from the fitdistrplus package in R, and the resulting shape and scale parameters were saved to disk. Since v is often zero-inflated, we also saved the fraction of non-zero AFs in v in order to incorporate the frequency of zero-valued observations into the final model. We selected the Weibull distribution owing to its superior observed performance in fitting position-specific non-zero background errors compared to other probability distributions (FIG. 14). To determine whether to learn background patterns in non-deduped or barcode-deduped data, we compared recurrence rates for position-specific errors. We observed high concordance between them suggesting that stereotypical background is not reliably suppressed by barcode deduping (e.g., 2×+singletons in FIG. 9(f)). We therefore used non-deduped data to model baseline distributions, yielding a background database φ.

To eliminate (i.e., "polish") stereotypical errors in an independent cfDNA sample s, we assessed the fractional abundance f of each candidate SNV in s using its corresponding background model in φ. If the model was Gaussian, we evaluated f with a one-sided z-test, yielding a p-value. Otherwise, shape and scale parameters from the Weibull distribution were used to calculate the cumulative probability p* that a given AF generated by the model was below f (using the pweibull function in R). To account for zero-inflated training data, we then adjusted p* using the fraction δ of non-zero AFs from the training set. Specifically, we used the following formula, p-value=1−((1−δ)+(δ×p*)), which is analogous in structure to the two-component zero-inflated Poisson model. Candidate SNV p-values, calculated by the z-test or zero-inflated Weibull distribution, were then adjusted for multiple hypothesis testing using stringent Bonferroni correction (where n=all base substitutions in the background database). Among candidate SNVs occurring in at least 2 normal controls and in at least 20% of normal controls in the training cohort, we eliminated a given candidate if and only if (i) it was statistically indistinguishable from background (adjusted P≥0.05), (ii) it was not present with duplex support, and (iii) f was less than 5% or the number of supporting molecules was ≤10.

Example 10

Estimating the Lowest Limit of Detection (LLOD) with an Improved Selector Design In this example, a lowest limit of detection (LLOD) of the method of the invention was estimated. First, an improved selector was designed. We obtained mutation annotation format (MAF) files from TCGA whole exome sequencing studies of 178 lung squamous cell carcinoma (SCC) tumors (v2.3) and 606 lung adenocarcinoma (LUAD) tumors (v2.4). MAF files were pre-filtered using UCSC genome browser feature tracks to eliminate variants in (i) repeat-rich genomic regions and (ii) intervals with low mapping rates. To prioritize inclusion of genomic regions, we used a heuristic approach that leverages a "recurrence index" (RI) as defined herein. A similar strategy was used previously, with exons as the primary genomic unit and without considering indels. Since only a subset of an exon may contain known somatic mutations, we restricted targeted regions to subsequences containing known lesions flanked by a user-defined buffer (by default, 1 bp), with a minimum tile size of 100 bp. Regions were subsequently ranked by decreasing RI, and those in the top 10 percent of both RI and the number of patients per exon were included that maximized additional patient coverage with minimal space. This process was then repeated, but percentile filters were relaxed (e.g., to permit the top ⅓ regions) and regions that maximally increased the median number of mutations per patient were added. Selector growth terminated when the desired size was reached (e.g., 175 kb for the NSCLC cfDNA selector), or when all genomic regions satisfying filters were exhausted. Fusions and seed regions were also included in the cfDNA selector. We also designed a larger clinical selector, which contained the entire cfDNA selector with the addition of copy number variations and histology classification regions. Probes for both libraries were automatically selected through the NimbleDesign portal (Roche NimbleGen, Madison, Wis.) using genome build hg19 NCBI Build 37.1/GRCh37 and with Preferred Close Matches set to 1 and Maximum Close Matches set to 2.

Figure 16:
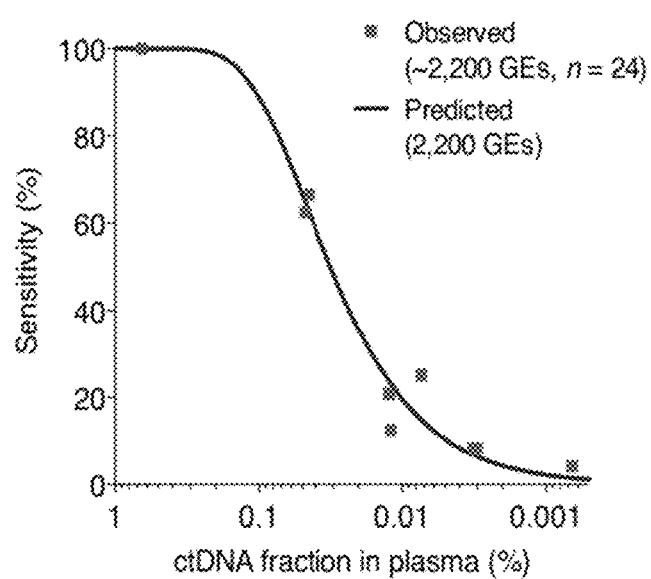
FIG. 16: Modeling the probability of detecting tumor DNA at various concentrations
Figure 16:
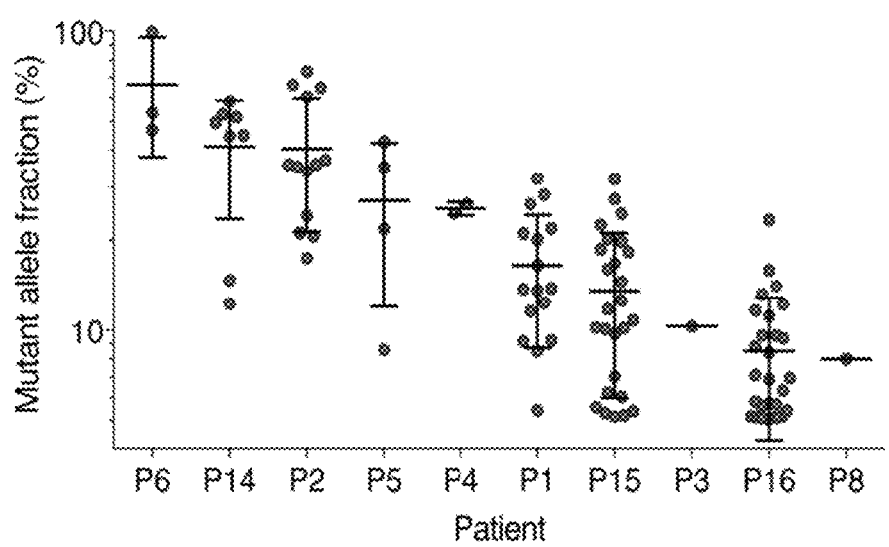
Figure 17A:
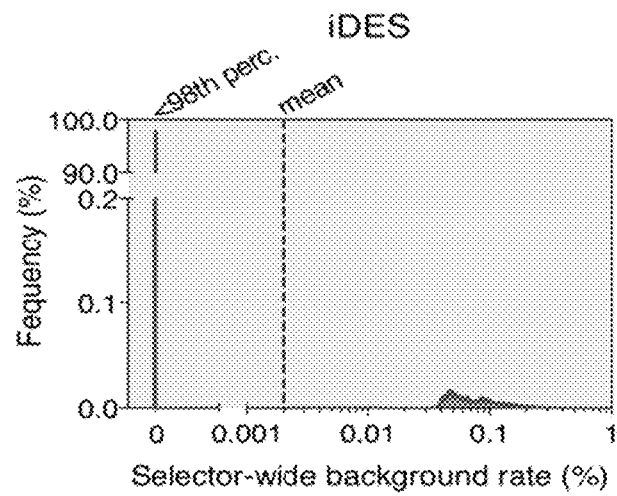
FIG. 17A-17B: Reducing selector-wide background rate by various methods
Figure 17A:
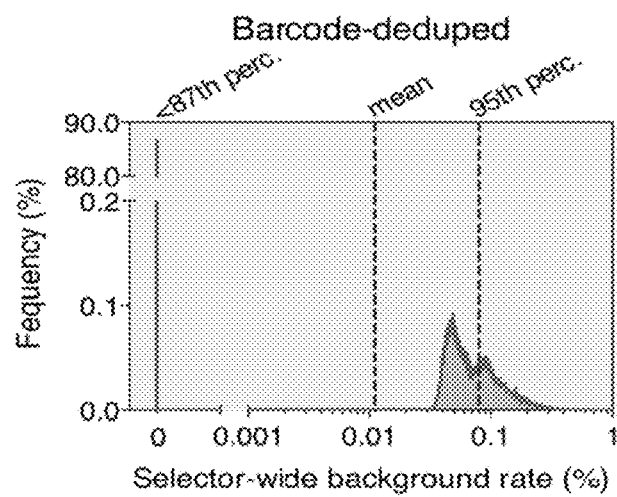
Figure 17A:
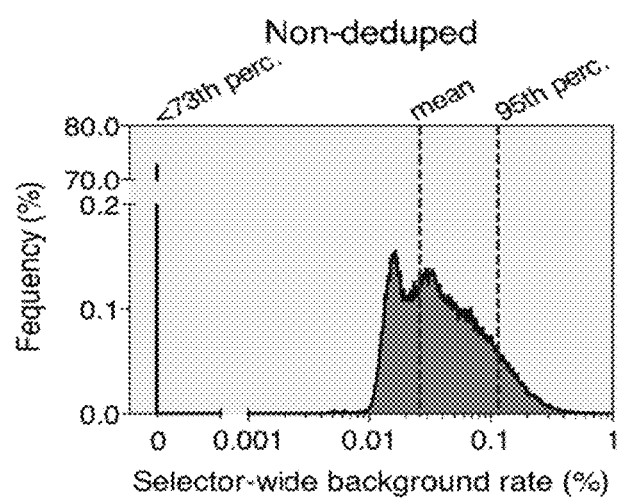
Figure 17B:
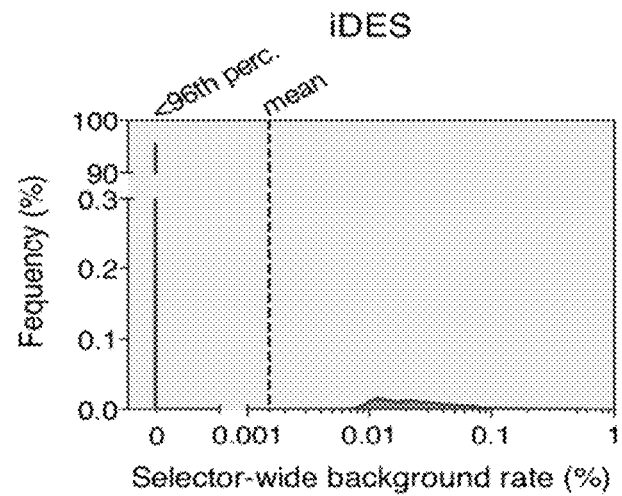
Figure 17B:
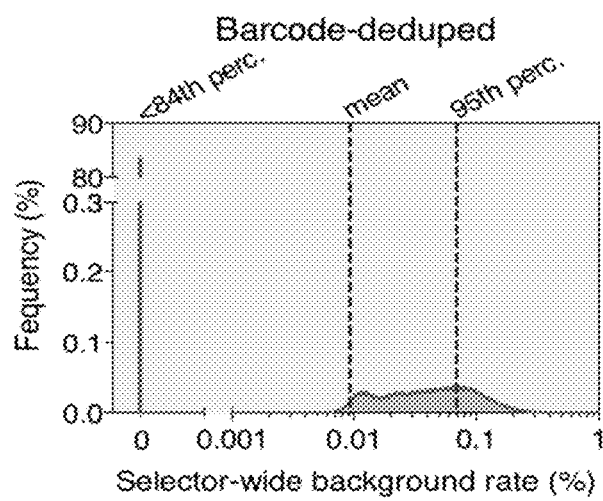
Figure 17B:
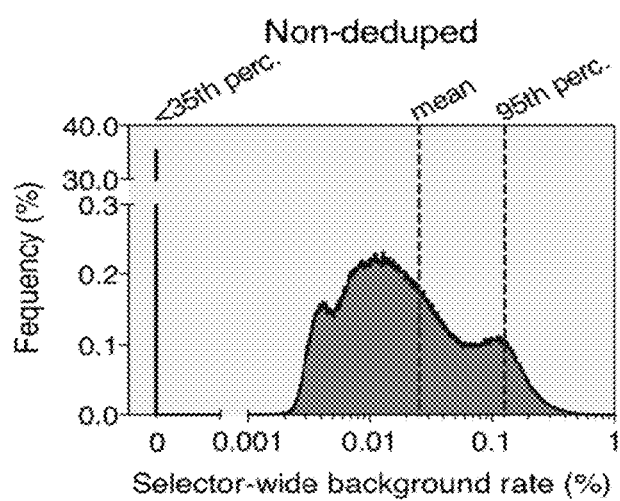

A robust model for predicting ctDNA detection thresholds would set performance expectations in clinical assays and facilitate improved design targets. We therefore developed an assay-independent model for estimating ctDNA sensitivity given knowledge of available tumor genome equivalents (GEs) and tumor-specific reporters (i.e., somatic variants). We found that ctDNA detection limits scale linearly with both quantities such that going from 1 reporter (e.g., dPCR) to 8 reporters (e.g., CAPP-Seq) yields an eight-fold reduction in the LLOD when DNA input is fixed (FIG. 15 (b)). This result holds if reporters behave independently, which is generally true for NSCLC (FIG. 15 (c)) and other cancers, and allows for the LLOD to drop below available tumor GEs (FIG. 15 (b)). By analyzing samples from our previous study, we found excellent concordance between observed and predicted numbers of distinct tumor-derived reporters in plasma ($R^2$=0.98; FIG. 15 (d); FIG. 16), thereby validating our model. Moreover, predictive performance was not significantly altered by fractional heterogeneity among tumor variants, consistent with reports that recurrent mutations tend to arise early in NSCLC tumorigenesis.

Example 11

Genotyping ctDNA of Multiple Tumor Types with a Lower LLOD

Using the method described in Example 1, we evaluated genotyping performance using a selector design targeting a two-fold improvement in LLOD and better addressing never-smokers (FIG. 15 (e)). In profiling 95 tumors from 87 NSCLC patients, including fine needle biopsies and formalin-fixed specimens, with matched peripheral blood leukocytes, we confirmed all clinically defined variants, and observed strong concordance between recurrently mutated regions in our cohort and training data (FIG. 15 (f)), including the median number of mutations per patient (FIG. 15 e). The method of Example 1 was then applied to samples from other carcinomas demonstrating a single selector for diverse human malignancies (e.g., FIG. 8 b-e).

Example 12

Comparing Error Suppression Using Adaptors with Internal and External UIDs

To benchmark error-suppression from molecular barcoding, we profiled cfDNA samples from 12 healthy adults. For each subject, we used uniform DNA inputs (median 32 ng) sequenced to a median depth of nearly 6,000× (prior to removing duplications). Given the typically low cfDNA yields in clinical plasma samples, we assessed barcoding performance using all recovered molecules (i.e., regardless of UID copy number or strandedness). When compared to "non-deduped" data, internal/insert molecular barcodes reduced selector-wide background by 60% (from ~0.025% to ~0.01%) and improved the fraction of error-free genomic positions by 50% (from ~60% to ~90%; FIG. 9 (b); FIG. 6 (b), FIG. 17). Since this approach generally outperformed external index UIDs, we used internal, insert UIDs as our main cfDNA error-suppression or barcode-deduping strategy (FIGS. 6 (b, c).

The data in this example demonstrates that in healthy blood donors, error-prone positions were strikingly stereotyped in their genomic locations and base-substitution spectrum (FIG. 9 (b) and FIG. 10). Even after error suppression using barcode-deduping, most remaining errors consisted of these stereotyped low frequency alleles (<0.1%), with the majority due to G>T transversions and, to a lesser extent, C>T or G>A transitions (FIG. 9 (b)). Without becoming bound by a particular theory, we hypothesized that oxidative damage during library preparation may be occurring leading to formation of 8-oxoguanine and cytosine deamination. Interestingly, when mapped to the opposite (plus) strand of the reference human genome, G>T changes were highly skewed compared to reciprocal C>A events (FIG. 9 (b)), and this imbalance was not attributable to sequencing strand bias (FIG. 11 (b)). We therefore examined the enrichment step, and identified a graded increase in the ratio of G>T errors to C>A errors reproducibly increasing by 2.5-fold between 0.1-long and 3 days-long duration of targeted capture (FIG. 11 c). A similar trend was observed for errors exclusively seen in both DNA strands (duplex-only data, FIG. 11 d). We therefore suspect that overrepresentation of G>T transversions is largely driven by reactive oxygen species coupled with a capture reagent that exclusively targets the positive strand (FIG. 11 e).

Enzymatic removal of damaged DNA bases was also tested using the following products: (i) uracil DNA-glycosylase (UDG; NEB catalog number M0372S), which leaves an abasic site in place of uracil (a cytosine oxidation product), preventing PCR from continuing through the site of oxidation, eliminating C>T errors due to cytosine oxidation; (ii) 8-oxoguanine DNA glycosylate (FPG; NEB catalog number M0240S), which removes damaged purines and cleaves at the site of the damaged bases, eliminating G>T errors due to guanine oxidation, and (iii) PreCR repair mix (NEB catalog number M0309S), which is designed to remove a variety of damaged bases, including oxidized guanines and cytosines. Before library preparation, cfDNA samples from healthy controls were treated with UDG (1 unit), FPG (8 units), UDG and FPG together, PreCR repair mix (1 uL), or the PreCR repair mix supplemented with 1 mg/mL BSA. Samples were treated for 30 minutes at 37° C., then UDG and FPG were inactivated by heating at 60° C. for 10 minutes. Samples were cleaned up using Ampure beads and eluted into 50 uL water for library preparation. (FIG. 11 (a)).

Example 13

Suppression of Position Specific Sequencing Errors (iDES)

We performed a serial application of molecular barcoding and in silico polishing, "integrated digital error suppression" (iDES). Using a set of healthy donor cfDNA samples to learn baseline distributions (FIG. 9 c), we performed "in silico polishing" of barcode-deduped data, eliminating variants with allele fractions below position-specific thresholds (FIG. 9 b) as described in Example. Consequently, selector-wide error rates dropped to $1.5 \times 10^{-5}$ and error-free positions increased to ~98%. Surprisingly, the inventors observed that application of background polishing to non-deduped cfDNA samples yielded similar error rates to barcode deduping alone (FIG. 9 c). Moreover, the two approaches synergized when combined (FIG. 9 c).

This example further investigated the landscape of stereotypical background errors and compares performance of error suppression techniques. FIG. 10 (top) shows a heat map depicting selector-wide background error patterns in 173 cfDNA samples including 30 normal controls, 12 of which were used as a training cohort to learn stereotypical background errors, and 143 cfDNA samples collected from NSCLC patients. The impact of barcoding, polishing and the combination thereof is shown. FIG. 10 (bottom) shows base substitution distributions and selector-wide error rates corresponding to samples in the heat map above.

Using iDES, we characterized allele-specific detection limits across large regions of the human genome that are recurrently mutated in cancer genomes. Of the 12 nucleotide-substitution classes, most were largely unaffected by background (FIG. 9 d), and nearly 80% of all possible SNVs were error-free (FIG. 9 e). Among residual errors, G>T detection was most notable, yet maintained a reasonably low median LLOD of ~0.3% across the selector (FIG. 9 d).

Moreover, G>T changes, which encompassed the majority of alleles with detection limits >0, comprised only 5% of mutational hotspots annotated by the Catalogue of Somatic Mutations in Cancer (COSMIC) overlapping our NSCLC selector, suggesting minimal impact on genotyping performance (FIG. 9 e).

Example 14

Comparing iDES to Prior Art Error-Suppression Barcoding Strategies

We next compared iDES to several error-suppression barcoding strategies. See FIG. 9 f, FIG. 10. Unlike iDES, which maximized usable genome equivalents (GEs) and balanced the distribution of base substitutions, barcode-deduping alone required >5 family members per UID to achieve a comparable error profile. This resulted in substantial loss of GEs even at our relatively high sequencing depths, and yielded only a modest improvement in G>T overrepresentation. Duplex molecules, by contrast, achieved an exceptionally low error rate of $2 \times 10^{-6}$ in healthy control cfDNA. The error rates (x-axis) and molecule recovery rates (y-axis; number of consensus reads per sequencing read) for methods reported in this work (i.e., iDES, barcoding or polishing only, duplex only) compared with error suppression methods from several other studies (Lou, D. I., et al. *High-throughput DNA sequencing errors are reduced by orders of magnitude using circle sequencing. Proc Natl Acad Sci USA* 110, 19872-19877 (2013), ("Lou"); Kennedy, S. R. et al. *Detecting ultralow-frequency mutations by Duplex Sequencing. Nat Protoc* 9, 2586-2606 (2014), ("Kennedy"); and Schmitt, M. W., et al. *Detection of ultra-rare mutations by next-generation sequencing. Proc Natl Acad Sci USA* 109, 14508-14513 (2012), ("Schmitt"). Of note, the theoretical error rate of duplex sequencing is approximately equivalent to the error rate of single strand barcode sequencing multiplied by itself and divided by 3 (to account for all possible base substitutions). However, the corresponding loss of single stranded molecules would likely hinder sensitivity for detecting rare variants from limited inputs of nucleic acids (FIG. 7). We therefore devised genotyping methods that leverage duplex molecules when available, but otherwise rely on background-polished single stranded molecules to augment the number of usable genome equivalents and maximize sensitivity.

Example 15

Evaluating Genotyping with iDES in Healthy Subjects

To evaluate biopsy-free genotyping with iDES, we first assessed its performance on ~300 somatic alterations (SNVs and indels) that are highly recurrent and clinically relevant in cancer within a predefined "whitelist". (See Example 20).

FIG. 12 illustrates biopsy-free tumor genotyping and ultrasensitive monitoring of NSCLC with iDES. Four replicates of 5% HD500 were queried for the presence of 29 known HD500 variants along with nearly 300 additional hotspot and/or clinically relevant mutations to assess specificity. FIG. 12 (a) (left) shows differential impact of barcoding, polishing and iDES on genotyping results for a single representative replicate. Only variant calls with at least 2 supporting reads are shown. FIG. 12 (a) (center) shows performance metrics across all four replicates. FIG. 12 (a) (right) shows comparison of error suppression methods for the mean number of variants detected per samples in 30 normal cfDNA controls and 25 pre-treatment NSCLC cfDNA samples. All variants analyzed in panel on the left were assessed excluding those specific to HD500. Group comparisons were performed using a two-sided Wilcoxon rank sum test. (NS—not significant) Data are expressed as means with 95% confidence intervals. FIG. 12 (b) shows HD500 allele fractions (AFs) for 13 variants across four replicates compared between CAPP-Seq (observed) and ground truth fractions (expected), as calibrated using droplet digital PCR (ddPCR). Data are expressed as means±s.e.m. FIG. 12 (c) shows that SNVs were detected in a 5% HD500 sample using selector-wide genotyping and were tracked across replicates and a ten-fold lower HD500 spike. Results are rendered as a heat map, with corresponding allele fractions shown below. Horizontal lines denote mean allele fractions (MAF). FIG. 12 (d) shows whitelist variants called in serial cfDNA samples from stage I-IV NSCLC patients using biopsy-free genotyping with iDES. Samples are ranked from left to right by decreasing MAF, and only those with ≥1 variant call and with a paired tumor biopsy are shown. Error bars denote range. FIG. 12 (e) shows Receiver Operating Characteristic (ROC) analysis of variants in d, along with additional EGFR calls with known clinical status. AUC, area under the curve. FIG. 12 (f) shows recovery rates of actionable EGFR mutations from the pretreatment plasma of advanced NSCLC tumors using biopsy-free tumor genotyping with iDES. FIG. 12 (g) shows comparison of post-processing methods for the detection of ctDNA in pretreatment plasma from 33 NSCLC patients. Patient-derived tumor reporters (columns; n=33 sets) were assessed in every plasma sample (rows; n=63), including 30 normal controls to evaluate specificity. The same samples were analyzed for each post-processing method (e.g., iDES) and are identically ordered in the heat map. Red squares, true positives; blue squares, false positives, white squares, undetected. FIG. 12. (h) shows monitoring of tumor burden in a patient with stage IIA NSCLC who underwent EGFR-targeted therapy. Pre, pretreatment; Carbo, carboplatin; Pem, pemetrexed; Cetux, cetuximab; DOD, deceased of disease. 'Monitoring' denotes the use of all tumor reporters to calculate a ctDNA detection index. The asterisk '*' denotes a time point in which EGFR T790M and del19 were undetectable. However ctDNA was significantly detectable using a monitoring framework. FIG. 12 (i) shows exploratory spike analysis to evaluate the detection limit of duplex sequencing. MAF, mutant allele fraction. Sn, sensitivity; Sp, specificity; PPV, positive predictive value; NPV, negative predictive value. Tick marks in the x-axes of a and d denote individual cfDNA samples.

When the selector was applied to cfDNA from 30 healthy subjects, iDES yielded only 8 calls 5 of which had duplex support, suggesting bona fide variant alleles arising in vivo. In contrast, barcode- and non-deduped data yielded 10- and 50-fold more calls in the same healthy subjects, respectively, indicating high false positive rates (FIG. 12 a, left). To benchmark performance, we simulated ctDNA using defined inputs of a commercial reference standard mutant DNA (HD500 Horizon Discovery, Cambridge, UK) spiked into control cfDNA. All validated HD500 variants were assessed in addition to our whitelist. Compared to barcode-deduping alone, iDES exhibited comparable sensitivity (96%) but achieved a higher specificity (99.9%), positive predictive value (PPV=99.1%) and negative predictive value (NPV=99.5%) for detecting variants down to 1-3 mutant molecules (in this case the LLOD for a single variant was ~0.04% given sequenced GEs; FIG. 12 a, right). Moreover, the fractional abundance of HD500 alleles was consistent across replicates and concordant with input concentrations (FIG. 12 b). These data suggest that iDES is a robust framework for biopsy-free genotyping of cfDNA. Unlike dPCR, iDES can interrogate numerous variants simultaneously without loss of sensitivity.

To expand the scope of variant detection beyond a predefined whitelist, we tested the performance of comprehensive selector-wide genotyping with iDES. Using a novel SNV detection method, we identified 324 SNVs in a cfDNA sample containing 5% mutant DNA HD500, recovering 21 (of 27) ground truth alleles. From our analysis, we calculated a 0.6% false positive rate (FIG. 12), indicating utility for biopsy free monitoring applications.

Example 16

Tumor Genotyping with iDES in NSCLC Patients

Figure 18C:
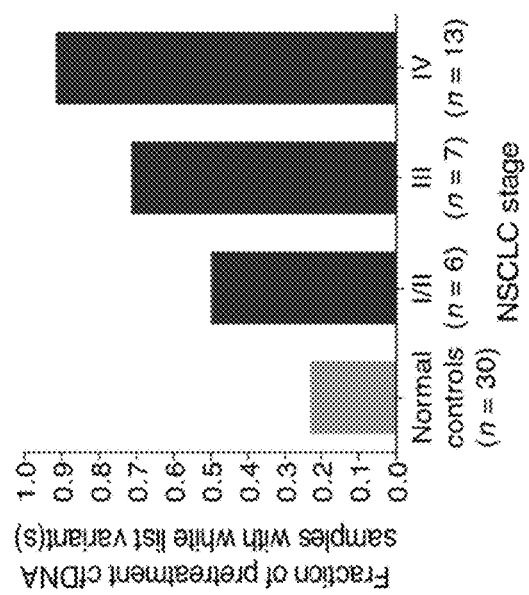
FIG. 18A-18C: Correlating mutations in cfDNA with tumor
Figure 18B:
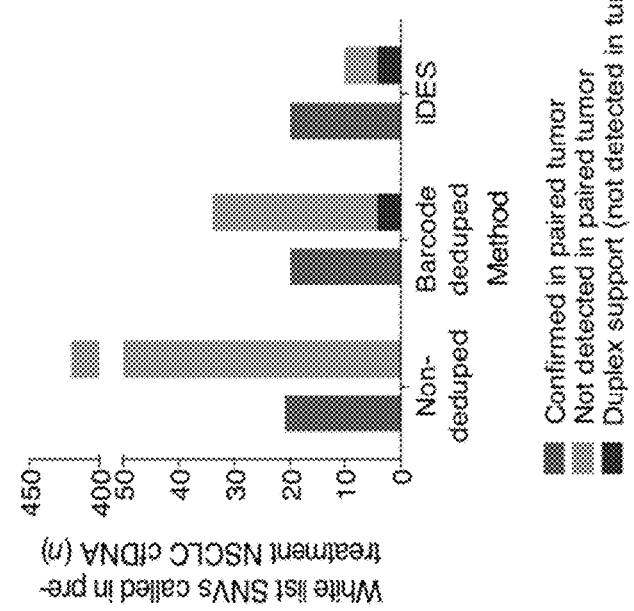
Figure 18A:
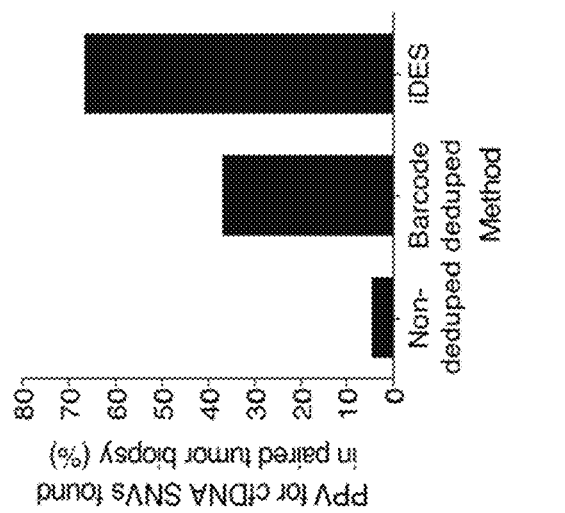
Figure 19A:
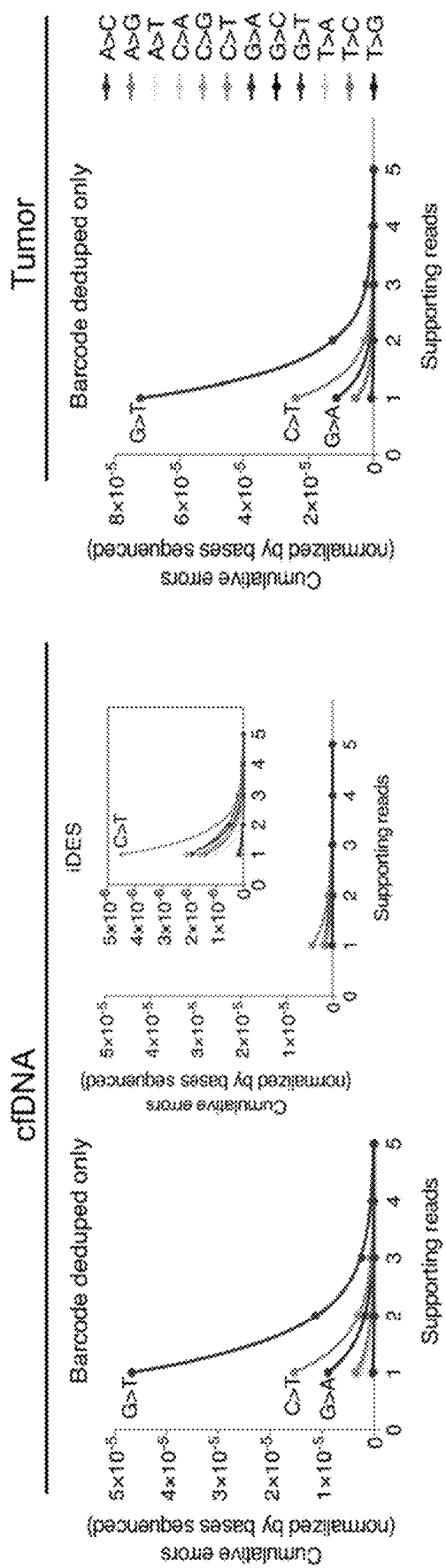
FIG. 19A-19C: Analysis of allele-specific detection limits following iDES
Figure 19C:
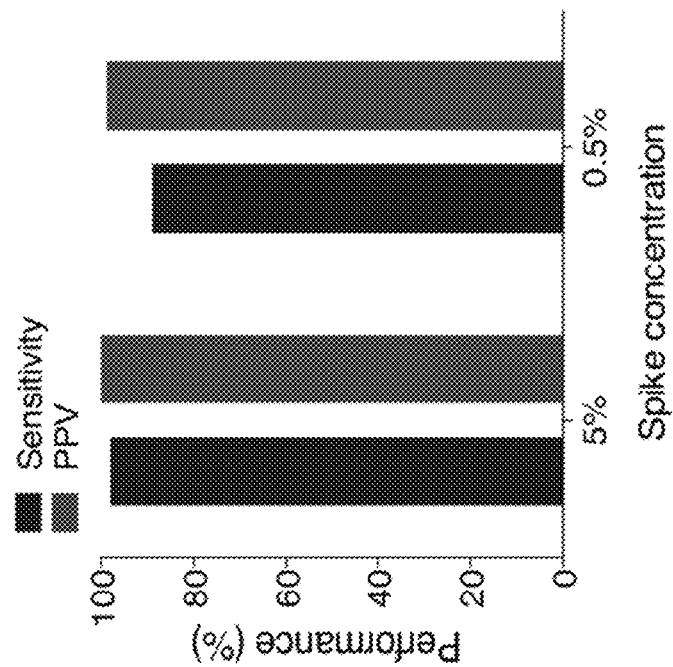
Figure 19B:
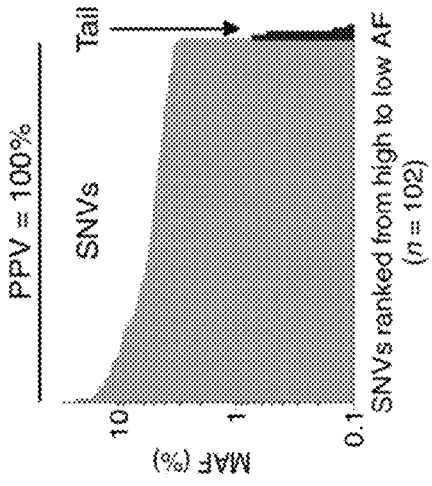
Figure 19B:
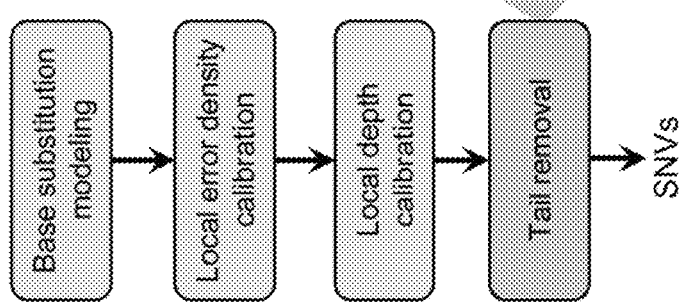

We next examined the clinical potential of iDES for biopsy-free genotyping of NSCLC patients from blood plasma. Nearly 72% of 71 serial plasma samples were found to harbor whitelist variants (FIG. 12 d), including 50% of early stage samples and 92% of advanced stage pre-treatment samples. Nearly two-thirds of detected variants were confirmed as somatic in a matched tumor biopsy. Most of the remaining variants were consistent with tumor-associated mutations that were subclonal, since two-thirds were independently found in serial time points or had duplex support. Indeed, such variants were more prevalent in patients with more advanced NSCLC stage, and were significantly more prevalent in NSCLC patients who had never smoked than in healthy adults (FIG. 18).

Example 17

Detecting EGFR Mutations in Plasma of NSCLC Patients Using iDES

We next focused on EGFR mutations given their importance for existing and emerging targeted therapies. In profiling NSCLC patients with stage IB-IV tumors, we confirmed 100% of 145 variants detected in plasma samples (FIG. 12 e). In pre-treatment cfDNA from advanced stage patients, the detection rates for actionable EGFR variants were high, with an average of 100% specificity and 95% sensitivity for activating mutations, and 83% sensitivity for subclonal T790M resistance mutations (FIG. 12 f). Since iDES outperformed other methods, these data demonstrate its promise for identifying clinically relevant mutations in cfDNA without prior knowledge of tumor genotypes.

Example 18

Detecting Known Tumor Genotypes in Plasma of NSCLC Patients Using iDES

We next asked whether iDES could yield similar improvements for ctDNA monitoring with prior knowledge of tumor genotypes. By empirically tuning the performance of a previously described ctDNA detection index, 94% of cases were detectable in pre-treatment plasma samples, including 100% of stage IB tumors, allowing 100% specificity when considering healthy adult controls (FIG. 12 g). Compared to iDES, duplex sequencing alone allowed comparable specificity, but suffered from lower sensitivity and significantly lower recovery of individual variants. Conversely, other approaches achieved comparable sensitivity, but lower specificity (FIG. 12 (g)). Similar performance was observed for post-treatment samples.

Separately, in a patient with stage IIA NSCLC who underwent EGFR-targeted therapy initially for del19 and later for T790M (FIG. 12 h), direct plasma genotyping revealed subclonal dynamics consistent with the dominant resistance mechanism following erlotinib. Following clinical response to chemotherapy, neither mutation was individually detectable. However, by integrating multiple reporters in a monitoring context, iDES, but not duplex sequencing, detected emergent molecular residual disease at this time point, and heralding clinical progression in this patient who ultimately succumbed to NSCLC (FIG. 12 h). In another patient with stage IIIB NSCLC, iDES detected 0.004% ctDNA preceding clinical progression, a five-fold improvement in the observed LLOD of our previous implementation. These data highlight the potential utility of iDES for discovering rare ctDNA molecules, with applications for the monitoring of minimal residual disease and noninvasive detection of resistance mutations.

Example 19

Detecting Tumor Mutation Load in Plasma Using Duplex Sequencing

Given the superior error rate of duplex sequencing, we sought to determine its LLOD for quantitating circulating tumor burden. To overcome the loss of single stranded molecules, (FIG. 9 f), we designed a "personalized" selector to cover >1,500 non-synonymous mutations identified by exome sequencing of a recurrent human glioblastoma. We then spiked defined quantities of tumor genomic DNA into control cfDNA based on considerations of reporter number and input mass. We obtained a DNA reference standard containing variants with known frequencies (HD500, Horizon Discovery) and spiked it into healthy donor cfDNA at 5% and 0.5% concentrations. Four CAPP-Seq libraries at each spike concentration were prepared and sequenced. Variants encoding EGFR L858R, KRAS G13D, and BRAF V600E were analyzed by ddPCR to calibrate expected spike concentrations. For FIG. 12 (a), we interrogated all HD500 variants that were (i) targeted by our NSCLC clinical selector and (ii) present in a ground truth mutation list provided by Horizon Diagnostics (i.e., 'Multiplex Complete Mutation List'). For FIG. 12 (b), we analyzed the subset of HD500 variants that were both internally validated by Horizon Diagnostics and targeted by our NSCLC clinical selector. Despite recovering <1,000 GEs with duplex support, the method accurately detected defined inputs from 0.025% to 0.00025% with high linearity (FIG. 12 i), further validating our analytical model and demonstrating a detection limit of 2.5 molecules in the background of 1,000,000, molecules, nearly 100× below the LLOD of single allele dPCR.

Example 20

"Whitelist" Genotyping

In this example, the script performs mutation recovery (SNVs and indels) from cfDNA and tumor samples without the need for paired germline samples by using a "whitelist" of user-defined variants to reduce the hypothesis space and increase sensitivity. A "whitelist" is a Supporting evidence takes the following order of precedence: duplex support (1×)>>strand support (2×)>>no strand support (3×). The minimum AF f required for calling SNVs is set using the following formula:

$f=\ln(1-p)/-n$, where $p$=probability of detection (0.95 by default) and $n$=the total GEs at a given genomic position.

Example 21

Performance of the Method at Various Concentrations of cfDNA

For the analyses in this work, we required a minimum position-specific depth of 20 GEs for tumors and 1,000 GEs for cfDNA. To incorporate paired germline samples, we eliminated candidate variant calls if present in paired germline with ≥1% AF, ≥4 supporting reads, and in a position with ≥10 total GEs.

We next evaluated the technical performance of our approach. First, we created an in silico dilution series in which a control cfDNA sample with median depth of 3,861 GEs was manipulated to introduce 100 uniformly distributed homozygous SNVs. Each synthetic numerator was then added to the original cfDNA sample in 5% and 0.5% proportions. To emulate the median length of cfDNA, thereby maintaining its distribution in sequencing data, genomic regions were randomly spiked in 170 bp contiguous segments. Robust performance was observed (FIG. 9(c)). Separately, in comparison to the approach we previously employed for tumor genotyping, we found the adaptive method to exhibit higher sensitivity and specificity for somatic genotyping of tumors, whose variant calls were assessed within a ctDNA monitoring framework (same analysis as in FIG. 9(g).

While the invention has been described in detail with reference to specific examples, it will be apparent to one skilled in the art that various modifications can be made within the scope of this invention. Thus the scope of the invention should not be limited by the examples described herein, but by the claims presented below.

We claim:

1. A method of reduced-error analysis of nucleic acid comprising:
   A) attaching to each end of nucleic acids isolated from blood or plasma, an adaptor from a pool of unique adaptors each adaptor comprising a double stranded portion at a proximal end and two single stranded portions at a distal end, wherein the double stranded portion comprises a double-stranded barcode of at least two base pairs specific to the adaptor, and wherein the single stranded portion containing a 5'-terminal nucleotide comprises: i) a pre-defined single-stranded barcode of one or two nucleotides specific to the sample; and ii) a random single-stranded barcode of one or two nucleotides specific to one strand of the adaptor on the same strand, wherein
   a) the double-stranded portion further comprises one or more G/C base pairs between the double-stranded barcode of at least two base pairs and the proximal end of the adaptor and wherein the number of G/C base pairs varies among the adaptors in the pool;
   b) the double-stranded barcode comprises 2-20 base pairs;
   B) sequencing the nucleic acids with attached adaptors to determine sequence and if present, sequence variations of the nucleic acids;

C) grouping the sequences of nucleic acids sharing the same random single-stranded barcode specific to one strand of the adaptor, to form barcode groups;
D) eliminating sequence variations that are present in fewer than all members of the barcode group;
E) eliminating sequence variations that are present at a frequency below a predetermined threshold among the barcode groups wherein the threshold is predetermined according to a method comprising the steps of:
  i. performing single molecule sequencing of multiple samples to determine the target nucleic acid sequence;
  ii. for each of the possible classes of nucleotide substitutions, determining a total number of substitutions (y) in all positions; and a number of supporting reads (t) for each position having a substitution;
  iii. defining a function relating y to t;
  iv. solving the function for the desired value of y by determining t, wherein t is the threshold number of reads above which the substitution may be called a sequence variation at the base position in the nucleic acid.

* * * * *

UNITED STATES PATENT AND TRADEMARK OFFICE
CERTIFICATE OF CORRECTION

| | | |
|---|---|---|
| PATENT NO. | : 11,085,084 B2 | Page 1 of 1 |
| APPLICATION NO. | : 15/509709 | |
| DATED | : August 10, 2021 | |
| INVENTOR(S) | : Diehn et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 728 days.

Signed and Sealed this
Twenty-fourth Day of January, 2023

Katherine Kelly Vidal
*Director of the United States Patent and Trademark Office*